(12) United States Patent
Inada et al.

(10) Patent No.: US 11,920,131 B2
(45) Date of Patent: Mar. 5, 2024

(54) METHOD OF PRODUCING HAIRPIN SINGLE-STRANDED RNA MOLECULE

(71) Applicant: Toray Industries, Inc., Tokyo (JP)

(72) Inventors: Hideaki Inada, Kamakura (JP); Katsuhiko Iseki, Otsu (JP); Keiichi Okimura, Kamakura (JP); Masato Sanosaka, Ibaraki (JP); Ayumi Takashina, Ibaraki (JP)

(73) Assignee: Toray Industries, Inc., Tokyo (JP)

( * ) Notice: Subject to any disclaimer, the term of this patent is extended or adjusted under 35 U.S.C. 154(b) by 486 days.

(21) Appl. No.: 16/981,329

(22) PCT Filed: Mar. 29, 2019

(86) PCT No.: PCT/JP2019/013923
§ 371 (c)(1),
(2) Date: Sep. 16, 2020

(87) PCT Pub. No.: WO2019/189722
PCT Pub. Date: Oct. 3, 2019

(65) Prior Publication Data
US 2021/0024930 A1 Jan. 28, 2021

(30) Foreign Application Priority Data
Mar. 30, 2018 (JP) ................................. 2018-070423

(51) Int. Cl.
*C12N 15/113* (2010.01)
(52) U.S. Cl.
CPC ...... *C12N 15/113* (2013.01); *C12N 2310/531* (2013.01)
(58) Field of Classification Search
CPC .................. C12N 15/113; C12N 2310/531
See application file for complete search history.

(56) References Cited

U.S. PATENT DOCUMENTS

| | | |
|---|---|---|
| 2003/0108902 A1 | 6/2003 | Abarzua |
| 2004/0058886 A1 | 3/2004 | Scaringe |
| 2010/0137407 A1 | 6/2010 | Abe et al. |
| 2014/0193860 A1 | 7/2014 | Bevilacqua et al. |
| 2014/0206856 A1 | 7/2014 | Aoki et al. |
| 2018/0023122 A1 | 1/2018 | Crameri et al. |
| 2018/0079768 A1 | 3/2018 | Aoki et al. |
| 2018/0339064 A1 | 11/2018 | Yamada et al. |
| 2020/0038427 A1 | 2/2020 | Ohgi et al. |

FOREIGN PATENT DOCUMENTS

| | | |
|---|---|---|
| EP | 2 256 191 A1 | 12/2010 |
| EP | 2 431 466 A1 | 3/2012 |
| EP | 2 436 767 A1 | 4/2012 |
| EP | 2 801 617 A1 | 11/2014 |
| EP | 3 778 914 A1 | 2/2021 |
| JP | 2003-532380 A | 11/2003 |
| JP | 2008-278784 A | 11/2008 |
| RU | 2628311 | 8/2017 |
| WO | 2011/052013 A1 | 5/2011 |
| WO | 2013/027843 A1 | 2/2013 |
| WO | 2013/077446 A1 | 5/2013 |
| WO | 2016/159374 A1 | 10/2016 |
| WO | 2017/035090 A1 | 3/2017 |
| WO | 2017/073767 A1 | 5/2017 |
| WO | 2018/182008 A1 | 10/2018 |
| WO | 2019/156020 A1 | 8/2019 |

OTHER PUBLICATIONS

Russian Office Action dated Jun. 9, 2022, of counterpart Russian Patent Application No. 2020130258, along with an English translation.
Kiong Ho, C. et al., "Structure and Mechanism of RNA Ligase", *Structure*, 12: pp. 327-339, Feb. 2004.
Song, Yunke et al., "Efficient Synthesis of Stably Adenylated DNA and RNA Adapters for Micro RNA Capture Using T4 RNA Ligase 1", *Scientific Reports*, 5(15620): pp. 1-6, Oct. 26, 2015.
Partial Supplementary European Search Report dated Jun. 27, 2022, of counterpart European Patent Application No. 19777814.5.
S. Honda et al., "Four-leaf clover qRT-PCR: A convenient method for selective quantification of mature tRNA," RNA Biology, vol. 12, No. 5, pp. 501-508, May 6, 2015.
S. Petkovic et al., "RNA circularization strategies in vivo and in vitro," Nucleic Acids Research, vol. 43, No. 4, pp. 2454-2465, Feb. 6, 2015.
G. Jibin et al., "Hypoxia-induced tumor cell resistance is overcome by synergistic GAPDH-siRNA and chemotherapy co-delivered by long-circulating and cationic-interior liposomes," Nanoscale, vol. 9, No. 7, pp. 9190-9201, Jun. 7, 2017.
R.D. Gonzalez-Cruz et al., "Nuclear Lamin Protein C is Linked to Lineage-Specific, Whole-Cell Mechanical Properties," Cellular and Molecular Bioengineering, Springer International Publishing, CHAM, vol. 11, No. 2, pp. 131-142, Jan. 16, 2018.
P.A. Antinozzi et al., "Functional mapping of disease susceptibility loci using cell biology," Proceedings of the National Academy of Sciences, vol. 103, No. 10, pp. 3698-3703, Mar. 7, 2006.
P.A. Antinozzi et al., "Supporting Information: Functional mapping of disease susceptibility loci using cell biology," Proceedings of the National Academy of Sciences, Table 1, Mar. 7, 2006.

(Continued)

*Primary Examiner* — J. E. Angell
(74) *Attorney, Agent, or Firm* — DLA Piper LLP (US)

(57) ABSTRACT

A method produces a hairpin single-stranded RNA molecule capable of inhibiting expression of a target gene, the method including: (i) an annealing step of annealing a first single-stranded oligoRNA molecule and a second single-stranded oligoRNA molecule; and (ii) a ligation step of ligating 3' end of the first single-stranded oligoRNA molecule and 5' end of the second single-stranded oligoRNA molecule by an Rnl2 family ligase, wherein a sequence produced by ligating the first single-stranded oligoRNA molecule and the second single-stranded oligoRNA molecule includes a gene expression-inhibiting sequence for the target gene.

14 Claims, 19 Drawing Sheets
Specification includes a Sequence Listing.

(56) References Cited

OTHER PUBLICATIONS

Office Action and Search Report dated Jan. 10, 2022, of counterpart Taiwanese Patent Application No. 108111164, along with an English translation.
Naoko Abe et al., "Synthesis, Structure and Biological Activity of Dumbbell-Shaped Nanocircular RNAs for RNA Interference," Bioconjugate Chemistry, 22(10), Sep. 23, 2011, pp. 2082-2092.
Notice of Reasons for Refusal dated Mar. 22, 2023, of counterpart Japanese Patent Application No. 2019-181613, along with an English translation.
Andrew Fire et al., "Potent and specific genetic interference by double-stranded RNA in Caenorhabditis elegans," Nature, Feb. 19, 1998, vol. 391 (6669), pp. 806-811.
Jayakrishnan Nandakumar et al., "RNA Ligase Structures Reveal the Basis for RNA Specificity and Conformational Changes that Drive Ligation Forward," Cell, Oct. 6, 2006, vol. 127, pp. 71-84.
Shozo Honda et al., "Dumbbell—PCR: a method to quantify specific small RNA variants with a single nucleotide resolution at terminal sequences," Nucleic Acids Research, 2015, vol. 43, No. 12 e77.
Naoko Abe, "RNA Interfering Effects and Translational Template Properties of Circularized RNA," Hokkaido University, 2015 w/partial translation.
Yuko Nakashima et al., "Nanostructured RNAs for RNA Interference," Methods in Molecular Biology, 2015, vol. 2018, pp. 17-36.
"Development of RNA medicine based on nano-structured design and templated reaction," Scientific Research Grant Project—Research Outcome Report, Jun. 28, 2016 w/translation.
Kai Cheng et al., "RNA ligation of very small pseudo nick structures by T4 RNA ligase 2, leading to efficient production of versatile RNA rings," RSC Advances, Mar. 14, 2019, vol. 9, pp. 8620-8627.
Jayakrishnan Nandakumar et al., "RNA Substrate Specificity and Structure-guided Mutational Analysis of Bacteriophage T4 RNA Ligase 2*," The Journal of Biological Chemistry, vol. 279, No. 30, Issue of Jul. 23, 2004, pp. 31337-31347.
Jayakrishnan Nandakumar et al., "How an RNA Ligase Discriminates RNA versus DNA Damage," Moleculrar Cell, vol. 16, Oct. 22, 2004, pp. 211-221.
Jayakrishnan Nandakumar et al., "Dual Mechanisms whereby a Broken RNA End Assists the Catalysis of Its Repair by T4 RNA Ligase 2*," The Journal of Biological Chemistry, vol. 280, No. 25, Issue of Jun. 24, 2005, pp. 23484-23489.
First Office Action dated Jul. 1, 2023, of counterpart Chinese Patent Application No. 201980019534.X, along with an English machine translation.

(SEQ ID NO: 1)

A

B

METHOD OF PRODUCING HAIRPIN SINGLE-STRANDED RNA MOLECULE

TECHNICAL FIELD

This disclosure relates to a method of producing a hairpin single-stranded RNA molecule.

BACKGROUND

As a gene expression-inhibiting technology, RNA interference (RNAi), for instance, has been known (Fire et al., Nature, Feb. 19, 1998; 391 (6669): 806-811). For RNA interference-mediated gene expression inhibition, widely used is a protocol using a short double-stranded RNA molecule called siRNA (small interfering RNA). In addition, a technique for inhibiting gene expression by using a circular RNA molecule in which a double strand is partially formed by intramolecular annealing has been reported (US Patent Application Publication No. 2004/058886).

However, siRNA has low stability in vivo, and siRNA is easily dissociated into single-stranded RNAs. Thus, it is difficult to stably inhibit gene expression. International Publication WO 2013/027843 reports that a hairpin single-stranded long-chain RNA molecule prepared by connecting a sense strand and an antisense strand of siRNA into a single strand using one or two linkers formed using a cyclic amine derivative can stabilize the siRNA. That hairpin single-stranded long-chain RNA molecule, however, cannot be efficiently synthesized by a phosphoramidite method using universal amidites such as TBDMS amidites. Accordingly, it is necessary to use special RNA amidites (e.g., WO '843 and International Publication WO 2016/159374) for the synthesis.

International Publication WO 2011/052013 discloses a method of ligating a first nucleic acid strand and a second nucleic acid strand by using an auxiliary nucleic acid as a third nucleic acid strand and T4 RNA ligase 2. However, WO '013 shows that as the auxiliary nucleic acid becomes longer, the reaction proceeds slower, indicating that only limited auxiliary nucleic acids provide favorable ligation efficiency in the above method.

It could therefore be helpful to provide an efficient method of producing a hairpin single-stranded RNA molecule capable of inhibiting expression of a target gene.

SUMMARY

We found that a hairpin single-stranded RNA molecule containing a target gene expression-inhibiting sequence can be efficiently produced, without any special RNA amidite or auxiliary nucleic acid, by segmenting the hairpin single-stranded RNA molecule into two single-stranded oligoRNA molecules each having a linker such as a non-nucleotide linker or a nucleotide linker and synthesizing them, and then annealing and ligating the molecules; and the ligation conditions can be modulated to further increase efficiency of production of the hairpin single-stranded RNA molecule relative to the amount of enzyme used.

We thus provide:

[1] A method of producing a hairpin single-stranded RNA molecule capable of inhibiting expression of a target gene, the method comprising:

an annealing step of annealing a first single-stranded oligoRNA molecule and a second single-stranded oligoRNA molecule; and a ligation step of ligating 3' end of the first single-stranded oligoRNA molecule and 5' end of the second single-stranded oligoRNA molecule by an Rnl2 family ligase, wherein the first single-stranded oligoRNA molecule comprises a first RNA region and a second RNA region that are connected via a first linker, and one of the first RNA region and the second RNA region is capable of complementarily binding to the other, the second single-stranded oligoRNA molecule comprises a third RNA region and a fourth RNA region that are connected via a second linker, and one of the third RNA region and the fourth RNA region is capable of complementarily binding to the other, the first single-stranded oligoRNA molecule and the second single-stranded oligoRNA molecule are capable of forming an intermolecular double strand between complementary sequences at 5'-end or 3'-end thereof, when the double strand is formed between the first single-stranded oligoRNA molecule and the second single-stranded oligoRNA molecule during the annealing step, a nick occurs between the 3'-end ribonucleotide residue of the first single-stranded oligoRNA molecule and the 5'-end ribonucleotide residue of the second single-stranded oligoRNA molecule, and a gap of at least one ribonucleotide residue is present between the 5'-end ribonucleotide residue of the first single-stranded oligoRNA molecule and the 3'-end ribonucleotide residue of the second single-stranded oligoRNA molecule, and a sequence produced by ligating the first single-stranded oligoRNA molecule and the second single-stranded oligoRNA molecule comprises a gene expression-inhibiting sequence for the target gene.

[2] The method according to [1] above, wherein the first single-stranded oligoRNA molecule is represented by formula (I) and the second single-stranded oligoRNA molecule is represented by formula (II):

5'-Xs-Lx$_1$-Xa-3'  (I)

5'-Ya$_1$-Ya$_2$-Ya$_3$-Lx$_2$-Ys-3'  (II)

wherein Xs, Xa, Ya$_1$, Ya$_2$, Ya$_3$, and Ys each represent one or more ribonucleotide residues, Lx$_1$ and Lx$_2$ represent the first linker and the second linker, respectively, Ya$_3$ is complementary to Ys, Xa-Ya$_1$, which is generated by the ligation step, is complementary to Xs, and Xa-Ya$_1$-Ya$_2$-Ya$_3$, which is generated by the ligation step, comprises a gene expression-inhibiting sequence for the target gene.

[3] The method according to [1] or [2] above, wherein the first single-stranded oligoRNA molecule has an uracil (U) or adenine (A) at the 3' end, and the second single-stranded oligoRNA molecule has an uracil (U) or adenine (A) at the 5' end.

[4] The method according to any one of [1] to [3] above, wherein the first linker and the second linker are each independently (i) a non-nucleotide linker comprising at least one selected from a pyrrolidine backbone and a piperidine backbone or (ii) a nucleotide linker.

[5] The method according to any one of [1] to [4] above, wherein the Rnl2 family ligase is T4 RNA ligase 2.

[6] The method according to any one of [1] to [5] above, wherein the ligating is carried out in a reaction solution at pH 7.4 to 8.6.
[7] The method according to any one of [1] to [6] above, wherein the ligating is carried out in a reaction solution comprising 2 to 10 mM divalent metal ion.
[8] The method according to any one of [1] to [7] above, wherein the first linker and the second linker are each independently a non-nucleotide linker represented by formula (VI):

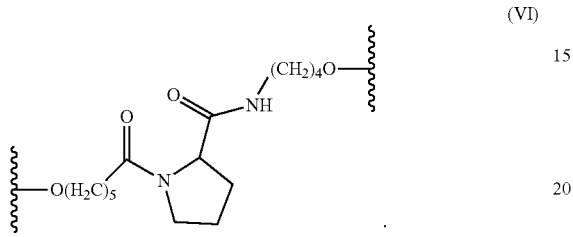

[9] The method according to any one of [1] to [8] above, wherein the target gene is TGF-β1 gene, GAPDH gene, LAMA1 gene, or LMNA gene.
[10] The method according to any one of [1] to [9] above, wherein the hairpin single-stranded RNA molecule consists of the nucleotide sequence set forth in SEQ ID NO: 1, and ribonucleotide residues at positions 24 and 25 are connected via the first linker and ribonucleotide residues at positions 50 and 51 are connected via the second linker.
[11] The method according to any one of [1] to [10] above, wherein the first single-stranded oligoRNA molecule and the second single-stranded oligoRNA molecule are any of (1) to (6):
  (1) a combination of the first single-stranded oligoRNA molecule consisting of the nucleotide sequence set forth in SEQ ID NO: 7 in which ribonucleotide residues at positions 24 and 25 are connected via the first linker and the second single-stranded oligoRNA molecule consisting of the nucleotide sequence set forth in SEQ ID NO: 6 in which ribonucleotide residues at positions 10 and 11 are connected via the second linker;
  (2) a combination of the first single-stranded oligoRNA molecule consisting of the nucleotide sequence set forth in SEQ ID NO: 19 in which ribonucleotide residues at positions 24 and 25 are connected via the first linker and the second single-stranded oligoRNA molecule consisting of the nucleotide sequence set forth in SEQ ID NO: 18 in which ribonucleotide residues at positions 16 and 17 are connected via the second linker;
  (3) a combination of the first single-stranded oligoRNA molecule consisting of the nucleotide sequence set forth in SEQ ID NO: 27 in which ribonucleotide residues at positions 24 and 25 are connected via the first linker and the second single-stranded oligoRNA molecule consisting of the nucleotide sequence set forth in SEQ ID NO: 26 in which ribonucleotide residues at positions 20 and 21 are connected via the second linker;
  (4) a combination of the first single-stranded oligoRNA molecule consisting of the nucleotide sequence set forth in SEQ ID NO: 29 in which ribonucleotide residues at positions 24 and 25 are connected via the first linker and the second single-stranded oligoRNA molecule consisting of the nucleotide sequence set forth in SEQ ID NO: 28 in which ribonucleotide residues at positions 21 and 22 are connected via the second linker;
  (5) a combination of the first single-stranded oligoRNA molecule consisting of the nucleotide sequence set forth in SEQ ID NO: 31 in which ribonucleotide residues at positions 24 and 25 are connected via the first linker and the second single-stranded oligoRNA molecule consisting of the nucleotide sequence set forth in SEQ ID NO: 30 in which ribonucleotide residues at positions 22 and 23 are connected via the second linker;
  (6) a combination of the first single-stranded oligoRNA molecule consisting of the nucleotide sequence set forth in SEQ ID NO: 33 in which ribonucleotide residues at positions 24 and 25 are connected via the first linker and the second single-stranded oligoRNA molecule consisting of the nucleotide sequence set forth in SEQ ID NO: 32 in which ribonucleotide residues at positions 23 and 24 are connected via the second linker.
[12] A single-stranded oligoRNA molecule, which is any one of (a) to (l):
  (a) a single-stranded oligoRNA molecule consisting of the nucleotide sequence set forth in SEQ ID NO: 7 in which ribonucleotide residues at positions 24 and 25 are connected via a linker;
  (b) a single-stranded oligoRNA molecule consisting of the nucleotide sequence set forth in SEQ ID NO: 6 in which ribonucleotide residues at positions 10 and 11 are connected via a linker;
  (c) a single-stranded oligoRNA molecule consisting of the nucleotide sequence set forth in SEQ ID NO: 19 in which ribonucleotide residues at positions 24 and 25 are connected via a linker;
  (d) a single-stranded oligoRNA molecule consisting of the nucleotide sequence set forth in SEQ ID NO: 18 in which ribonucleotide residues at positions 16 and 17 are connected via a linker;
  (e) a single-stranded oligoRNA molecule consisting of the nucleotide sequence set forth in SEQ ID NO: 27 in which ribonucleotide residues at positions 24 and 25 are connected via a linker;
  (f) a single-stranded oligoRNA molecule consisting of the nucleotide sequence set forth in SEQ ID NO: 26 in which ribonucleotide residues at positions 20 and 21 are connected via a linker;
  (g) a single-stranded oligoRNA molecule consisting of the nucleotide sequence set forth in SEQ ID NO: 29 in which ribonucleotide residues at positions 24 and 25 are connected via a linker;
  (h) a single-stranded oligoRNA molecule consisting of the nucleotide sequence set forth in SEQ ID NO: 28 in which ribonucleotide residues at positions 21 and 22 are connected via a linker;
  (i) a single-stranded oligoRNA molecule consisting of the nucleotide sequence set forth in SEQ ID NO: 31 in which ribonucleotide residues at positions 24 and 25 are connected via a linker;
  (j) a single-stranded oligoRNA molecule consisting of the nucleotide sequence set forth in SEQ ID NO: 30 in which ribonucleotide residues at positions 22 and 23 are connected via a linker;

(k) a single-stranded oligoRNA molecule consisting of the nucleotide sequence set forth in SEQ ID NO: 33 in which ribonucleotide residues at positions 24 and 25 are connected via a linker; and (l) a single-stranded oligoRNA molecule consisting of the nucleotide sequence set forth in SEQ ID NO: 32 in which ribonucleotide residues at positions 23 and 24 are connected via a linker.

[13] A kit that produces a hairpin single-stranded RNA molecule for inhibiting expression of TGF-β1 gene, comprising a combination of single-stranded oligoRNA molecules of any of (1) to (6):

(1) a combination of a first single-stranded oligoRNA molecule consisting of the nucleotide sequence set forth in SEQ ID NO: 7 in which ribonucleotide residues at positions 24 and 25 are connected via a first linker and a second single-stranded oligoRNA molecule consisting of the nucleotide sequence set forth in SEQ ID NO: 6 in which ribonucleotide residues at positions 10 and 11 are connected via a second linker;

(2) a combination of a first single-stranded oligoRNA molecule consisting of the nucleotide sequence set forth in SEQ ID NO: 19 in which ribonucleotide residues at positions 24 and 25 are connected via a first linker and a second single-stranded oligoRNA molecule consisting of the nucleotide sequence set forth in SEQ ID NO: 18 in which ribonucleotide residues at positions 16 and 17 are connected via a second linker;

(3) a combination of a first single-stranded oligoRNA molecule consisting of the nucleotide sequence set forth in SEQ ID NO: 27 in which ribonucleotide residues at positions 24 and 25 are connected via a first linker and a second single-stranded oligoRNA molecule consisting of the nucleotide sequence set forth in SEQ ID NO: 26 in which ribonucleotide residues at positions 20 and 21 are connected via a second linker;

(4) a combination of a first single-stranded oligoRNA molecule consisting of the nucleotide sequence set forth in SEQ ID NO: 29 in which ribonucleotide residues at positions 24 and 25 are connected via a first linker and a second single-stranded oligoRNA molecule consisting of the nucleotide sequence set forth in SEQ ID NO: 28 in which ribonucleotide residues at positions 21 and 22 are connected via a second linker;

(5) a combination of a first single-stranded oligoRNA molecule consisting of the nucleotide sequence set forth in SEQ ID NO: 31 in which ribonucleotide residues at positions 24 and 25 are connected via a first linker and a second single-stranded oligoRNA molecule consisting of the nucleotide sequence set forth in SEQ ID NO: 30 in which ribonucleotide residues at positions 22 and 23 are connected via a second linker; and (6) a combination of a first single-stranded oligoRNA molecule consisting of a nucleotide sequence set forth in SEQ ID NO: 33 in which ribonucleotide residues at positions 24 and 25 are connected via a first linker and a second single-stranded oligoRNA molecule consisting of the nucleotide sequence set forth in SEQ ID NO: 32 in which ribonucleotide residues at positions 23 and 24 are connected via a second linker.

This disclosure includes the contents disclosed in Japanese Patent Application No. 2018-070423 from which this application claims priority.

A hairpin single-stranded RNA molecule capable of inhibiting the expression of a target gene can thus be produced efficiently.

DETAILED DESCRIPTION

Figure 1:
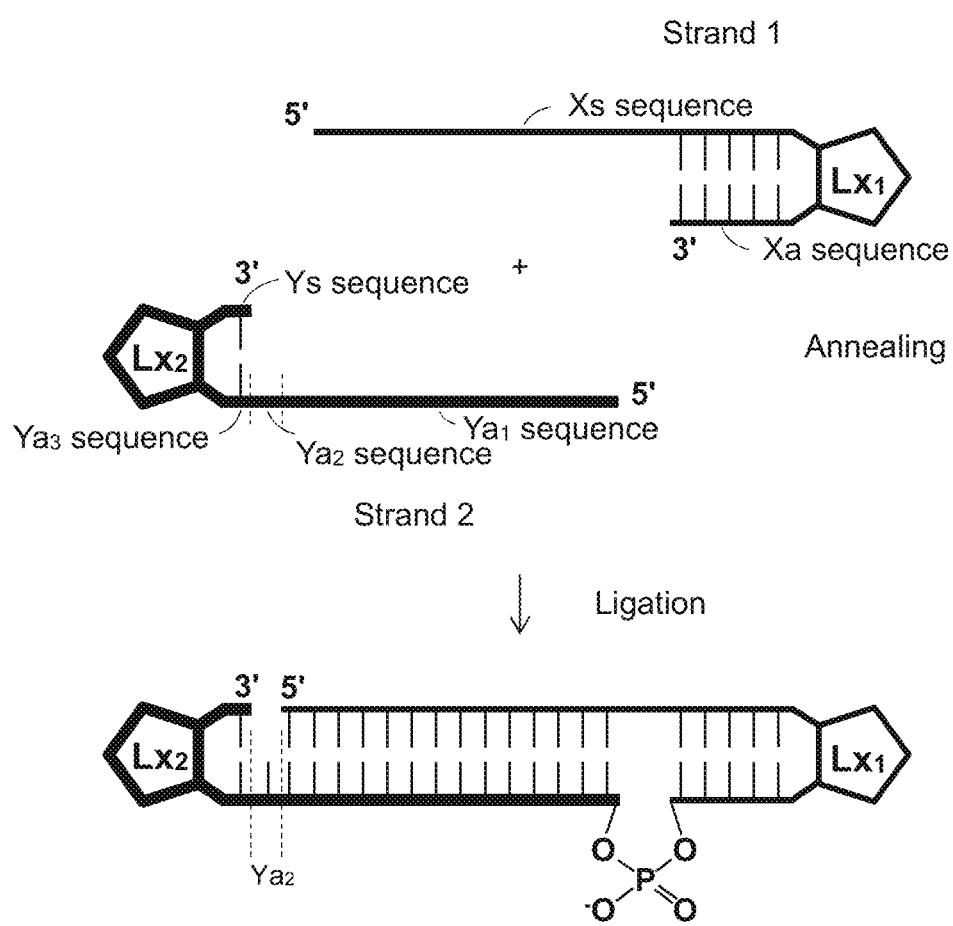
FIG. 1 is a schematic drawing illustrating an example of our ligation method.

Hereinafter, our methods, molecules and kits will be described in detail.

Our method produces a hairpin single-stranded RNA molecule capable of inhibiting expression of a target gene. A hairpin single-stranded RNA molecule produced by a method has a single strand structure, in which the 3' end of the sense strand and the 5' end of the antisense strand of a double-stranded RNA containing a gene expression-inhibiting sequence are connected via a sequence containing a linker such as a non-nucleotide linker or a nucleotide linker and at least one ribonucleotide residue is further connected, via a sequence containing a linker such as a non-nucleotide linker or a nucleotide linker, to the 3' end of the antisense strand. The 5' end and the 3' end of the hairpin single-stranded RNA molecule produced by the method are not linked therebetween. The "hairpin" means that a single-stranded RNA molecule is intramolecularly annealed (self-annealed) to form at least one double-stranded structure. In the hairpin single-stranded RNA molecule produced by our method, typically, a 5'-side region containing the 5' end and a 3'-side region containing the 3' end are each individually and intramolecularly annealed to form two double-stranded structures. The "RNA," "RNA molecule," "nucleic acid molecule" and "nucleic acid" may be composed of only nucleotides or may be composed of nucleotides and non-nucleotide substances (e.g., a cyclic amine derivative such as a proline derivative).

A hairpin single-stranded RNA molecule capable of inhibiting expression of a target genes are segmented into two segmentation fragments, within a sequence between two linkers (e.g., a non-nucleotide linker, a nucleotide linker, or a combination linker thereof) of the molecule, and the segmentation fragments are synthesized, annealed, and then ligated, thereby producing the hairpin single-stranded RNA molecule. The ligation means that two nucleic acids (typically RNAs) are connected by bonding (i.e., by a phosphodiester bond) the 5'-end phosphate group and the 3'-end hydroxyl group. A relatively long hairpin single-stranded RNA molecule can be produced by ligating a pair of shorter single-stranded RNA molecules. This method enables the hairpin single-stranded RNA molecule to be successfully produced in a high yield.

More specifically, our method produces a hairpin single-stranded RNA molecule capable of inhibiting expression of a target gene, the method comprising:

an annealing step of annealing a first single-stranded oligoRNA molecule and a second single-stranded oligoRNA molecule; and a ligation step of ligating 3' end of the first single-stranded oligoRNA molecule and 5' end of the second single-stranded oligoRNA molecule by an Rnl2 family ligase, wherein a sequence produced by ligating the first single-stranded oligoRNA molecule and the second single-stranded oligoRNA molecule comprises a gene expression-inhibiting sequence for the target gene.

The first single-stranded oligoRNA molecule comprises a first RNA region and a second RNA region that are connected via a first linker, and one of the first RNA region and the second RNA region is complementarily binding to the other. The complementary binding causes the first linker to form a loop. The first RNA region and the second RNA region can form a stem adjacent to the loop. In the first single-stranded oligoRNA molecule, the first RNA region is located on the 5'-end side and the second RNA region is located on the 3'-end side. In addition, the second single-stranded oligoRNA molecule comprises a third RNA region and a fourth RNA region connected via a second linker, and one of the third RNA region and the fourth RNA region is capable of complementarily binding to the other. The complementary binding causes the second linker to form a loop. The third RNA region and the fourth RNA region can form a stem adjacent to the loop. In the second single-stranded oligoRNA molecule, the third RNA region is located on the 5'-end side and the fourth RNA region is located on the 3'-end side. The first to fourth RNA regions each comprise one or two or more ribonucleotide residues. As such, the first single-stranded oligoRNA molecule and the second single-stranded oligoRNA molecule each contain a self-complementary sequence and are each intramolecularly annealed (self-annealed) to form a hairpin structure. One of the first RNA region or the second RNA region preferably has a longer nucleotide length than the other. Also, one of the third RNA region or the fourth RNA region preferably has a longer nucleotide length than the other. When the first RNA region has a longer nucleotide length than the second RNA region, the third RNA region preferably has a longer nucleotide length than the fourth RNA region. When the second RNA region has a longer nucleotide length than the first RNA region, the fourth RNA region preferably has a longer nucleotide length than the first RNA region. Of either the first RNA region or the second RNA region, an RNA region having a longer nucleotide length preferably contains a ribonucleotide residue(s) or a sequence thereof complementary to the other RNA region having a shorter nucleotide length, adjacent to the first linker. Of either the third RNA region or the fourth RNA region, an RNA region having a longer nucleotide length preferably contains a ribonucleotide residue(s) or a sequence thereof complementary to the other RNA region having a shorter nucleotide length, adjacent to the second linker.

That one of two RNA regions (the first and second RNA regions, or the third and fourth RNA regions) comprised in the single-stranded oligoRNA molecule is "capable of complementarily binding to" the other means that the full-length of one of the two RNA regions (usually an RNA region having a shorter nucleotide length) is able to bind to the other RNA region (usually, an RNA region having a longer nucleotide length) while forming a stable base-pairing. In this example, the full-length of the former RNA region is complementary to a corresponding ribonucleotide residue(s) or sequence thereof within the latter RNA region. It is more preferred that one of two RNA regions comprised in the single-stranded oligoRNA molecule be completely complementary to a corresponding ribonucleotide residue(s) or sequence thereof within the other RNA region (i.e., all ribonucleotide residues of one of the RNA regions have no mismatch with corresponding ribonucleotide residues of the other RNA region). Alternatively, one of two RNA regions comprised in the single-stranded oligoRNA molecule may contain one or more, for instance, one or two ribonucleotide residue mismatches with the other RNA region, as long as a stable base pairing can be formed. "Capable of complementarily binding to" can also apply to this example. In this regard, however, such mismatches preferably are not present at ribonucleotide residues at the end(s) of molecules to be ligated in the method.

In an example, one of the first RNA region or the fourth RNA region is shorter than the other and has preferably 1 to 7, for instance, 1 to 6, 1 to 4, 1 to 3, or 1 or 2 nucleotide(s) in length. In this example, a longer one (i.e., the other) of the first RNA region or the fourth RNA region may have from 19 to 28, for instance, from 19 to 27, from 19 to 25, from 19 to 23, from 20 to 28, from 21 to 27, from 20 to 25, from 22 to 27, from 23 to 26, from 24 to 28, or from 26 to 28 nucleotides in length.

When the first RNA region is longer than the fourth RNA region, the second RNA region may have, but is not limited to, from 1 to 20, for instance, from 2 to 20, from 2 to 15, from 3 to 10, from 3 to 6, from 5 to 12, or from 9 to 12 nucleotide(s) in length. When the first RNA region is shorter than the fourth RNA region, the second RNA region may have, but is not limited to, from 8 to 38, for instance from 8 to 36, from 12 to 36, from 14 to 34, from 14 to 33, from 14 to 36, or from 20 to 34 nucleotides in length.

The nucleotide sequence of the first RNA region may contain CC (cytosine-cytosine) adjacent to a linker and, in this example, the nucleotide sequence of the second RNA region preferably contains GG (guanine-guanine) adjacent to a linker to be complementary to the above sequence. In an example, the nucleotide sequence of the first RNA region may contain ACC (adenine-cytosine-cytosine), GCC (guanine-cytosine-cytosine), or UCC (uracil-cytosine-cytosine) adjacent to a linker and, in this example, the nucleotide sequence of the second RNA region preferably contains GGU (guanine-guanine-uracil), GGC (guanine-guanine-cytosine), or GGA (guanine-guanine-adenine) adjacent to a linker to be complementary to the above sequence. The nucleotide sequence of the third RNA region may contain C (cytosine) adjacent to a linker and, in this example, the nucleotide sequence of the fourth RNA region preferably contains G (guanine) adjacent to a linker to be complementary to the above residue.

The nucleotide length of the first or second single-stranded oligoRNA molecule, that is, the total nucleotide length of the two RNA regions (without a linker portion) is, but not limited to, preferably 13 to 48 nucleotides in length. When the first RNA region is longer than the fourth RNA region, the nucleotide length of the first single-stranded oligoRNA molecule, that is, the total nucleotide length of the first and second RNA regions (without a linker portion) is preferably from 21 to 48, for instance, from 21 to 45, from 25 to 45, from 26 to 35, from 26 to 30, from 26 to 28, or from 33 to 36 nucleotides in length. When the first RNA region is shorter than the fourth RNA region, the nucleotide length of the first single-stranded oligoRNA molecule, that is, the total nucleotide length of the first and second RNA regions (without a linker portion) is preferably from 13 to 45, for instance, from 13 to 43, from 15 to 41, from 15 to 30, from 17 to 25, or from 20 to 25 nucleotides in length.

A 5'-end sequence and/or a 3'-end sequence of the first single-stranded oligoRNA molecule and the second single-stranded oligoRNA molecule used in a method, are complementary to one another. The first single-stranded oligoRNA molecule and the second single-stranded oligoRNA molecule are capable of forming an intermolecular double strand between complementary sequences (preferably between completely complementary sequences) at the 5'-end or 3'-end of the single-stranded oligoRNA molecules. More specifically, in an example, an intermolecular double strand can be formed because a 5'-end sequence of the first single-stranded oligoRNA molecule having a hairpin structure (a 5'-end sequence of the first RNA region, outside a stem-loop of the hairpin structure) and a 5'-end sequence of the second single-stranded oligoRNA molecule having a hairpin structure (a 5'-end sequence of the third RNA region, outside a stem-loop of the hairpin structure) are complementary to one another. In another example, an intermolecular double strand can be formed because a 3'-end sequence of the first single-stranded oligoRNA molecule having a hairpin structure (a 3'-end sequence of the second RNA region, outside a stem-loop of the hairpin structure) and a 3'-end sequence of the second single-stranded oligoRNA molecule having a hairpin structure (a 3'-end sequence of the fourth RNA region, outside a stem-loop of the hairpin structure) are complementary to one another. In an annealing step in our method, the first single-stranded oligoRNA molecule and the second single-stranded oligoRNA molecule can form an intermolecular double strand between the complementary sequences at the 5'-end or 3'-end to produce a double-stranded oligoRNA.

In an example, the length of complementary sequences between the first and second single-stranded oligoRNA molecules (without a gap portion described below) may be, but is not limited to, usually 6 or longer, for instance, 7 or longer, 10 or longer, 12 or longer, 14 or longer, or 18 or longer and, for instance, from 6 to 27, from 7 to 25, from 10 to 25, from 12 to 23, from 12 to 22, from 12 to 15, or from 18 to 23 nucleotides in length.

When a double strand is formed between the first single-stranded oligoRNA molecule and the second single-stranded oligoRNA molecule during an annealing step in our method, a nick occurs between the 3'-end ribonucleotide residue of the first single-stranded oligoRNA molecule and the 5'-end ribonucleotide residue of the second single-stranded oligoRNA molecule. More specifically, during the annealing step, complementary sequences between the first and second single-stranded oligoRNA molecules are intermolecularly annealed to form a double strand (intermolecular double strand) between the first single-stranded oligoRNA molecule and the second single-stranded oligoRNA molecule. In addition, the first and second RNA regions and the third and fourth RNA regions are each intramolecularly annealed to form a double strand (an intramolecular double strand, namely a hairpin structure); and a nick occurs between the second RNA region and the third RNA region. The "nick" refers to a state in which a phosphodiester bond is cleaved between two nucleotide residues of one of the nucleotide strands of a nucleic acid double strand and the 3' hydroxyl group and the 5' phosphate group are dissociated. The nick can be joined by a ligation reaction.

When a double strand is formed between the first single-stranded oligoRNA molecule and the second single-stranded oligoRNA molecule during the annealing step in our method, a gap of at least one ribonucleotide residue is present between the 5'-end ribonucleotide residue of the first single-stranded oligoRNA molecule and the 3'-end ribonucleotide residue of the second single-stranded oligoRNA molecule. This gap is not filled by a ligation reaction. Thus, the first single-stranded oligoRNA molecule and the second single-stranded oligoRNA molecule are ligated to form a single-stranded RNA molecule. The gap of at least one ribonucleotide residue may be a gap of 1 to 4 residues (1, 2, 3, or 4 residues). In this gap, no base pairing is formed.

This gap between the 5'-end ribonucleotide residue of the first single-stranded oligoRNA molecule and the 3'-end ribonucleotide residue of the second single-stranded oligoRNA molecule may be positioned near the first linker or may be positioned near the second linker in a double strand having the first single-stranded oligoRNA molecule and the second single-stranded oligoRNA molecule annealed.

A sequence produced by ligating the first single-stranded oligoRNA molecule and the second single-stranded oligoRNA molecule comprises a gene expression-inhibiting sequence for a target gene. The first RNA region or the fourth RNA region may contain a gene expression-inhibiting sequence (a sense sequence or an antisense sequence; for instance, a sense sequence) for a target gene. A sequence in which the second RNA region and the third RNA region are linked by ligation may contain a gene expression-inhibiting sequence (an antisense sequence or a sense sequence; for instance, an antisense sequence) for a target gene. In an example, the second RNA region or the third RNA region may contain a gene expression-inhibiting sequence (an antisense sequence or a sense sequence; for instance, an antisense sequence) for a target gene.

A linker, for instance, the first linker or the second linker may be a non-nucleotide linker, a nucleotide linker, or a combination thereof.

In an example, the first single-stranded oligoRNA molecule has an uracil (U) or adenine (A) at the 3' end, and the second single-stranded oligoRNA molecule has an uracil (U) or adenine (A) at the 5' end. That a single-stranded oligoRNA molecule has an uracil (U) or adenine (A) at the 3' end or the 5' end means that the 3'-end or 5'-end ribonucleotide residue of the single-stranded oligoRNA molecule contains, as a nucleotide, an uracil (U) or adenine (A). Specifically, U-A, U-U, A-U, or A-A may be a preferred combination of a nucleotide of the 3'-end ribonucleotide residue of the first single-stranded oligoRNA molecule and a nucleotide of the 5'-end ribonucleotide residue of the second single-stranded oligoRNA molecule.

FIG. 1 is a schematic drawing illustrating a method according to an example. In FIG. 1, Lx$_1$ and Lx$_2$ are each a linker (e.g., a non-nucleotide linker, a nucleotide linker, or a combination thereof). A relatively long hairpin single-stranded RNA molecule may be produced by ligating a pair of shorter single-stranded RNA molecules. This allows for a high yield.

In an example, a method of producing a hairpin single-stranded RNA molecule capable of inhibiting expression of a target gene comprises:

an annealing step of annealing a first single-stranded oligoRNA molecule (Strand 1 in FIG. 1) represented by formula (I):

5'-Xs-Lx$_1$-Xa-3'      (I), a second single-stranded oligoRNA molecule (strand 2 in FIG. 1) represented by formula (II):

5'-Ya$_1$-Ya$_2$-Ya$_3$-Lx$_2$-Ys-3'      (II), and a ligation step of ligating the 3' end of the first single-stranded oligoRNA molecule with the 5' end of the second single-stranded oligoRNA molecule. This ligation may be carried out using an Rnl2 family ligase.

In another example, a method of producing a hairpin single-stranded RNA molecule capable of inhibiting expression of a target gene comprises:

an annealing step of annealing a first single-stranded oligoRNA molecule represented by formula (A):

5'-XXs-Lx$_1$-XXa$_3$-XXa$_2$-XXa$_1$-3'      (A); and a second single-stranded oligoRNA molecule represented by formula (B):

5'-YYa-Lx$_2$-YYs-3'      (B), and a ligation step of ligating the 3' end of the first single-stranded oligoRNA molecule with the 5' end of the second single-stranded oligoRNA molecule. This ligation may be carried out using an Rnl2 family ligase.

The "oligoRNA" and "oligoRNA molecule" refer to an RNA molecule having a nucleotide sequence with a nucleotide length of 49 or less (the number of residues in a linker portion such as a non-nucleotide linker and a nucleotide linker is not counted). The terms "oligoRNA" and "oligoRNA molecule" are used commonly and interchangeably. The single-stranded oligoRNA molecule is sometimes called a single-stranded oligoRNA, oligo nucleic acid, single-stranded nucleic acid molecule, oligoRNA, or oligoRNA molecule.

In formulas (I) and (II), Xs, Xa, Ya$_1$, Ya$_2$, Ya$_3$, and Ys each represent one or more ribonucleotide residues. In formulas (I) and (II), Lx$_1$ and Lx$_2$ each independently represent a linker such as a non-nucleotide linker, a nucleotide linker, or a combination thereof.

Formula (I) represents a structure in which regions Xs and Xa are connected via Lx$_1$. Formula (II) represents a structure in which a ribonucleotide sequence (Ya$_1$-Ya$_2$-Ya$_3$) having regions Ya$_1$, Ya$_2$, and Ya$_3$ connected in this order and a region Ys are connected via Lx$_2$.

In formulas (A) and (B), XXs, XXa$_3$, XXa$_2$, XXa$_1$, YYa, and YYs each represent one or more ribonucleotide residues. In formulas (A) and (B), Lx$_1$ and Lx$_2$ each independently represent a linker such as a non-nucleotide linker, a nucleotide linker, or a combination thereof.

Formula (A) represents a structure in which a ribonucleotide sequence (XXa$_3$-XXa$_2$-XXa$_1$) having regions XXa$_3$, XXa$_2$, and XXa$_1$ connected in this order and a region XXs are connected via Lx$_1$. Formula (B) represents a structure in which regions YYa and YYs are connected via Lx$_2$.

Xs, Xa, Ya$_1$, Ya$_2$, Ya$_3$, Ys, XXs, XXa$_3$, XXa$_2$, XXa$_1$, YYa, and YYs are each composed of a ribonucleotide residue(s). The ribonucleotide residue(s) may contain any nucleobase(s) selected from adenine, uracil, guanine, or cytosine. The ribonucleotide residue(s) may also have a modified ribonucleotide residue(s) and has, for instance, a modified nucleobase(s) (modified base(s)). Examples of the modification include, but are not limited to, fluorescent dye labeling, methylation, halogenation, pseudouridilation, amination, deamination, thiolation, or dihydroxylation. Xs, Xa, $Ya_1$, $Ya_2$, $Ya_3$, and Ys, each independently, may consist of only an unmodified ribonucleotide residue(s), may contain an unmodified ribonucleotide residue(s) and a modified ribonucleotide residue(s), or may contain only a modified ribonucleotide residue(s). The 5' end of Xs may contain a modified ribonucleotide residue. The 3' end of Ys may contain a modified ribonucleotide residue. Likewise, XXs, $XXa_2$, $XXa_3$, $XXa_1$, YYa, and YYs, each independently, may consist of only an unmodified ribonucleotide residue(s), may contain an unmodified ribonucleotide residue(s) and a modified ribonucleotide residue(s), or may contain only a modified ribonucleotide residue(s). The 5' end of XXs may contain a modified ribonucleotide residue. The 3' end of YYs may contain a modified ribonucleotide residue.

The Xa-$Ya_1$ produced in the ligation step (a nucleotide sequence in which Xa and $Ya_1$ are linked by ligation) is complementary to Xs. In an example, Xs may have from 19 to 28, for instance, from 19 to 27, from 19 to 25, from 19 to 23, from 20 to 28, from 21 to 27, from 21 to 25, from 22 to 27, from 23 to 26, from 24 to 28, or from 26 to 28 nucleotides in length.

The $XXa_1$-YYa produced in the ligation step (a nucleotide sequence in which $XXa_1$ and YYa are linked by ligation) is complementary to YYs. In an example, YYs may have from 19 to 28, for instance, from 19 to 27, from 19 to 25, from 19 to 23, from 20 to 28, from 21 to 27, from 21 to 25, from 22 to 27, from 23 to 26, from 24 to 28, or from 26 to 28 nucleotides in length.

Xa is complementary to a corresponding residue(s) or sequence in Xs. In an example, the nucleotide sequence of Xs in formula (I) may contain C (cytosine) adjacent to a linker. In this example, the nucleotide sequence of Xa contains G (guanine) that is complementary to Xs and adjacent to the linker. In an example, the nucleotide sequence of Xs in formula (I) may contain CC (cytosine-cytosine) adjacent to a linker. In this example, the nucleotide sequence of Xa contains GG (guanine-guanine) that is complementary to Xs and adjacent to the linker. In an example, the nucleotide sequence of Xs in formula (I) may contain ACC (adenine-cytosine-cytosine) adjacent to a linker. In this example, the nucleotide sequence of Xa contains GGU (guanine-guanine-uracil) that is complementary to Xs and adjacent to the linker. In an example, Xa may contain a nucleotide uracil (U) or adenine (A) at the 3' end. Xa may have from 1 to 20, for instance, from 2 to 20, from 2 to 15, from 3 to 10, from 3 to 6, from 5 to 12, or from 9 to 12 nucleotides in length.

$XXa_3$ is complementary to XXs. In an example, the nucleotide sequence of XXs in formula (A) may contain C (cytosine) adjacent to a linker. In this example, the nucleotide sequence of $XXa_3$ contains G (guanine) that is complementary to XXs and adjacent to the linker. In an example, the nucleotide sequence of XXs in formula (A) may contain CC (cytosine-cytosine) adjacent to a linker. In this example, the nucleotide sequence of $XXa_3$ contains GG (guanine-guanine) that is complementary to XXs and adjacent to the linker. In an example, the nucleotide sequence of XXs in formula (A) may contain ACC (adenine-cytosine-cytosine; in a 5'-to-3' direction) adjacent to a linker. In this example, the nucleotide sequence of $XXa_3$ contains GGU (guanine-guanine-uracil; in a 5'-to-3' direction) that is complementary to XXs and adjacent to the linker. In an example, the nucleotide sequence of $XXa_1$ may contain a nucleotide uracil (U) or adenine (A) at the 3' end. $XXa_3$ and XXs each preferably have from 1 to 7, for instance from 1 to 4, or 1 or 2 nucleotides in length. In an example, when YYs has from 26 to 28 nucleotides in length, $XXa_3$ and XXs may each have 1 nucleotide in length.

$Ya_3$ is complementary to Ys. In an example, the nucleotide sequence of $Ya_3$ may contain C (cytosine) adjacent to a linker. In this example, the nucleotide sequence of Ys contains G (guanine) that is complementary to $Ya_3$ and adjacent to the linker. $Ya_3$ and Ys each preferably have from 1 to 7, for instance, from 1 to 4, or 1 or 2 nucleotides in length. In an example, when Xs has from 26 to 28 nucleotides in length, $Ya_3$ and Ys may each have 1 nucleotide in length.

YYa is complementary to a corresponding residue(s) or sequence in YYs. In an example, the nucleotide sequence of YYa may contain C (cytosine) adjacent to a linker. In this example, the nucleotide sequence of YYs contains G (guanine) that is complementary to YYa and adjacent to the linker. YYa may have from 2 to 20, for instance, from 2 to 15, from 3 to 10, from 3 to 6, from 5 to 12, or from 9 to 12 nucleotides in length.

The "complementary" means that a stable base pairing can be formed between two nucleic acids or nucleotides. The two complementary nucleic acids have the same nucleotide length. The two complementary nucleic acids typically consist of sequences complementary to each other (complementary strands), that is, they are completely complementary. Alternatively, the two complementary nucleic acids may comprise a modified nucleotide(s) and a nucleotide(s) that can form a base pairing therewith at a corresponding position(s) during annealing.

$Ya_2$ fails to form any base pairing with either Xs or Ys when a hairpin single-stranded RNA molecule after ligation is intramolecularly annealed (self-annealed). $Ya_2$ preferably has from 1 to 4 nucleotides in length, for instance, 1, 2, or 3 nucleotides in length. Likewise, $XXa_2$ fails to form any base pairing with either XXs or YYs when a hairpin single-stranded RNA molecule after ligation is intramolecularly annealed (self-annealed). $XXa_2$ preferably has from 1 to 4, for instance, 1, 2, or 3 nucleotides in length.

Regarding the first single-stranded oligoRNA molecule (strand 1), the total nucleotide length of Xs and Xa (without a linker portion such as a non-nucleotide linker, a nucleotide length, or a combination thereof) in formula (I) is preferably from 21 to 48, for instance, from 21 to 45, from 25 to 45, from 26 to 35, from 26 to 30, from 26 to 28, or from 33 to 36 nucleotides in length.

Regarding the second single-stranded oligoRNA molecule (strand 2), $Ya_1$ in formula (II) has preferably from 6 to 27, for instance, from 7 to 25, from 10 to 25, from 12 to 23, from 12 to 22, from 12 to 15, or from 18 to 23 nucleotides in length.

Regarding the second single-stranded oligoRNA molecule (strand 2), the total nucleotide length of $Ya_1$, $Ya_2$, $Ya_3$, and Ys (without a linker portion such as a non-nucleotide linker, a nucleotide length, or a combination thereof) in formula (II) is preferably from 13 to 45, for instance, from 13 to 43, from 15 to 41, from 15 to 30, from 17 to 25, or from 20 to 25 nucleotides in length.

Regarding the first single-stranded oligoRNA molecule (strand 1), the total nucleotide length of XXs, $XXa_3$, $XXa_2$, and $XXa_1$ (without a linker portion such as a non-nucleotide linker, a nucleotide length, or a combination thereof) in formula (A) is preferably from 13 to 45, for instance, from 13 to 43, from 15 to 41, from 15 to 30, from 17 to 25, or from 20 to 25 nucleotides in length.

XXa$_1$ preferably has from 6 to 27, for instance, from 7 to 25, from 10 to 25, from 12 to 23, from 12 to 22, from 12 to 15, or from 18 to 23 nucleotides in length.

Regarding the second single-stranded oligoRNA molecule (strand 2), the total nucleotide length of YYa and YYs (without a linker portion such as a non-nucleotide linker, a nucleotide length, or a combination thereof) in formula (B) is preferably from 21 to 48, for instance, from 21 to 45, from 25 to 45, from 26 to 35, from 26 to 30, from 26 to 28, or from 33 to 36 nucleotides in length.

Linkers such as the first linker and the second linker are not particularly limited and may be each independently, for instance, a non-nucleotide linker, a nucleotide linker, or a combination thereof. The nucleotide linker comprises one or more nucleotide residues (ribonucleotide residues or deoxyribonucleotide residues; preferably ribonucleotide residues). The non-nucleotide linker contains no nucleotide residue. The constituent unit of a linker used is not particularly limited and may be a nucleotide residue(s) and/or a non-nucleotide residue(s). The combination linker of a non-nucleotide linker and a nucleotide linker contains both a nucleotide residue(s) and a non-nucleotide residue(s). A linker may be composed of, for instance, any of the following (1) to (7) residues:

(1) an unmodified nucleotide residue(s);
(2) a modified nucleotide residue(s);
(3) a combination of a unmodified nucleotide residue(s) and a modified nucleotide residue(s);
(4) a non-nucleotide residue(s);
(5) a combination of a non-nucleotide residue(s) and an unmodified nucleotide residue(s);
(6) a combination of a non-nucleotide residue(s) and a modified nucleotide residue(s); and
(7) a combination of a non-nucleotide residue(s), an unmodified nucleotide residue(s), and a modified nucleotide residue(s).

In an example, both the first linker and the second linker may consist of a nucleotide residue(s) (a nucleotide linker) or may consist of a non-nucleotide residue(s) (a non-nucleotide linker). Alternatively, one of the first linker or the second linker may consist of a nucleotide residue(s) and the other may consist of a non-nucleotide residue(s). The first linker and the second linker (as Lx$_1$ and Lx$_2$ linkers in the above formulas) may have the same structure or may have different structures.

A linker such as the first linker or the second linker (Lx$_1$ or Lx$_2$ in the above formulas) contains a non-nucleotide residue(s). In this example, the number of non-nucleotide residues is not particularly limited and may be, for instance, from 1 to 8, from 1 to 6, from 1 to 4, or 1, 2, or 3. The "non-nucleotide residue(s)" refers to a constituent unit of non-nucleotide linker. Examples of the non-nucleotide residue(s) include, but are not limited to, a cyclic amine derivative having a pyrrolidine backbone or a piperidine backbone. The non-nucleotide residue(s) may have, for instance, a structure represented by formula (III) below as a unit (one structure).

In an example, a linker such as the first linker or the second linker (Lx$_1$ or Lx$_2$ in the above formulas) may be a non-nucleotide linker containing at least one of a pyrrolidine backbone and/or a piperidine backbone. The first linker and the second linker (as Lx$_1$ and Lx$_2$ in the above formulas) may have the same structure or may have different structures. The first linker and the second linker (as Lx$_1$ and Lx$_2$ in the above formulas), each independently, may have a non-nucleotide structure containing a pyrrolidine backbone, may have a non-nucleotide structure containing a piperidine backbone, or may have both the non-nucleotide structure containing a pyrrolidine backbone and the non-nucleotide structure containing a piperidine backbone. A hairpin single-stranded RNA molecule produced by a method excels in nuclease resistance because the sense strand and the antisense strand thereof are connected via such linkers.

In a hairpin single-stranded RNA molecule, the pyrrolidine backbone, for instance, may be a pyrrolidine derivative backbone in which at least one carbon atom of the 5-membered pyrrolidine ring is replaced. If replaced, for instance, the carbon atom(s) other than the carbon atom at position 2 (C-2) is preferably replaced. The above carbon atom(s) may be replaced by, for instance, a nitrogen atom(s), an oxygen atom(s), or a sulfur atom(s). The pyrrolidine backbone may contain, for instance, a carbon-carbon double bond or a carbon-nitrogen double bond in the 5-membered pyrrolidine ring. In the above pyrrolidine backbone, for instance, a hydrogen atom(s) or the below-described substituent(s) may be attached to the carbon atom(s) and the nitrogen atom constituting the 5-membered pyrrolidine ring. The linker Lx$_1$ may be linked Xs and Xa in formula (I) and XXs and XXa$_3$ in formula (A) via, for instance, any of groups in the above pyrrolidine backbone. The linker Lx$_2$ may be linked Ya$_3$ and Ys in formula (II) and YYa and YYs in formula (B) via, for instance, any of groups in the above pyrrolidine backbone. They may be linked through any one of the carbon atoms and the nitrogen atom in the above 5-membered ring and preferably through the carbon atom at position 2 (C-2) and the nitrogen atom in the above 5-membered ring. Examples of the above pyrrolidine backbones include a proline backbone or a prolinol backbone.

The above piperidine backbone may be a piperidine derivative backbone in which at least one carbon of the 6-membered piperidine ring, for instance, is replaced. If replaced, for instance, the carbon atom(s) other than the C-2 carbon atom is preferably replaced. The above carbon atom(s) may be replaced by, for instance, a nitrogen atom(s), an oxygen atom(s), or a sulfur atom(s). The piperidine backbone may contain, for instance, a carbon-carbon double bond or a carbon-nitrogen double bond in the 6-membered piperidine ring. In the above piperidine backbone, for instance, a hydrogen atom(s) or the below-described substituent(s) may be attached to the carbon atom(s) and the nitrogen atom constituting the 6-membered piperidine ring. The linker Lx$_1$ may be linked Xs and Xa in formula (I) or XXs and XXa$_3$ in formula (A) via, for instance, any of groups in the above piperidine backbone. The linker Lx$_2$ may be used to link Ya$_3$ and Ys in formula (II) and YYa and YYs in formula (B) via, for instance, any of groups in the above piperidine backbone. They may be linked through any one of the carbon atoms and the nitrogen atom in the above 6-membered ring and preferably through the carbon atom at position 2 (C-2) and the nitrogen atom in the above 6-membered ring.

The above linker may comprise, for instance, only a non-nucleotide residue(s) composed of the above non-nucleotide structure.

The above linker region may be represented by formula (III) or may contain one or two or more non-nucleotide residues represented by formula (III):

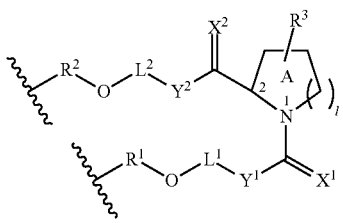

(III)

wherein $X^1$ and $X^2$ are each independently $H_2$, O, S, or NH;

$Y^1$ and $Y^2$ are each independently a single bond, $CH_2$, NH, O, or S;

$R^3$ is a hydrogen atom or a substituent bonded to C-3, C-4, C-5, or C-6 on ring A;

$L^1$ is an alkylene chain containing n atoms where a hydrogen atom on any alkylene carbon atom is optionally unsubstituted or substituted by OH, $OR^a$, $NH_2$, $NHR^a$, $NR^aR^b$, SH, or $SR^a$ or $L^1$ is a polyether chain in which at least one carbon atom of the alkylene chain is replaced by an oxygen atom, where when $Y^1$ is NH, O, or S, an $L^1$ atom bonded to $Y^1$ is carbon and an $L^1$ atom bonded to $OR^1$ is carbon while oxygen atoms are not next to each other;

$L^2$ is an alkylene chain containing m atoms where a hydrogen atom on any alkylene carbon atom is optionally unsubstituted or substituted by OH, $OR^c$, $NH_2$, $NHR^c$, $NR^cR^d$, SH, or $SR^c$ or $L^2$ is a polyether chain in which at least one carbon atom of the alkylene chain is replaced by an oxygen atom, where when $Y^2$ is NH, O, or S, an $L^2$ atom bonded to $Y^2$ is carbon and an $L^2$ atom bonded to $OR^2$ is carbon while oxygen atoms are not next to each other;

$R^a$, $R^b$, $R^c$, and $R^d$ are each independently a substituent or a protecting group;

l is 1 or 2;

m is an integer of 0 to 30;

n is an integer of 0 to 30;

ring A is provided such that a carbon atom other than C-2 on ring A is optionally replaced by a nitrogen atom, an oxygen atom, or a sulfur atom, and ring A optionally contains a carbon-carbon double bond or a carbon-nitrogen double bond; and wherein $R^1$ and $R^2$ are optionally present or absent and when present, $R^1$ and $R^2$ are each independently a non-nucleotide residue represented by formula (III) where neither $R^1$ nor $R^2$ is present.

Xs or Xa in formula (I) or XXs or $XXa_3$ in formula (A) may be linked, via $-OR^1-$ or $-OR^2-$ in formula (III), to the linker $Lx_1$. In an example, Xs may be linked, via $-OR^1-$, and Xa may be linked, via $-OR^2-$, to the linker $Lx_1$. In another example, Xs may be linked, via $-OR^2-$ and Xa may be linked, via $-OR^1-$, to the linker $Lx_1$. In another example, XXs may be linked, via $-OR^1-$, and $XXa_3$ may be linked, via $-OR^2-$, to the linker $Lx_1$. In another example, XXs may be linked, via $-OR^2-$, and $XXa_3$ may be linked, via $-OR^1-$, to the linker $Lx_1$.

$Ya_3$ or Ys in formula (II) or YYa or YYs in formula (B) may be linked, via $-OR^1-$ or $-OR^2-$ in formula (III), to the linker $Lx_2$. In an example, $Ya_3$ may be linked, via $-OR^1-$, and Ys may be linked, via $-OR^2-$, to the linker $Lx_2$. In another example, $Ya_3$ may be linked, via $-OR^2-$ and Ys may be linked, via $-OR^1-$, to the linker $Lx_2$. In another example, YYa may be linked, via $-OR^1-$, and YYs may be linked, via $-OR^2-$, to the linker $Lx_2$. In another example, YYa may be linked, via $-OR^2-$, and YYs may be linked, via $-OR^1-$, to the linker $Lx_2$.

In a preferred example, Xs may be linked, via $-OR^2-$, and Xa may be linked, via $-OR^1-$, to the linker $Lx_1$, and, in addition, $Ya_3$ may be linked, via $-OR^2-$, and Ys may be linked, via $-OR^1-$, to the linker $Lx_2$. In another preferred example, XXs may be linked, via $-OR^2-$, and $XXa_3$ may be linked, via $-OR^1-$, to the linker $Lx_1$ and, in addition, YYa may be linked, via $-OR^2-$, and YYs may be linked, via $-OR^1-$, to the linker $Lx_2$.

For instance, $X^1$ and $X^2$ in formula (III) are each independently $H_2$, O, S, or NH. That $X^1$ is $H_2$ in formula (III) means that $X^1$ and a carbon atom bonded to $X^1$ together form $CH_2$ (a methylene group). The same applies to $X^2$.

$Y^1$ and $Y^2$ in formula (III) are each independently a single bond, $CH_2$, NH, O, or S.

In ring A of formula (III), l is 1 or 2. When l=1, ring A is a 5-membered ring, for instance, the above pyrrolidine backbone. Examples of the above pyrrolidine backbone include a proline backbone or a prolinol backbone, and the above pyrrolidine backbone can be exemplified by a divalent structure thereof. When l=2, ring A is a 6-membered ring. Examples include the above piperidine backbone. Ring A is provided such that a carbon atom other than C-2 on ring A is optionally replaced by a nitrogen atom, an oxygen atom, or a sulfur atom. In addition, ring A optionally contains a carbon-carbon double bond or a carbon-nitrogen double bond in ring A. For instance, ring A may be either L-form or D-form.

In formula (III), $R^3$ is a hydrogen atom or a substituent bonded to C-3, C-4, C-5, or C-6 on ring A. When $R^3$ is the above substituent, the number of substituents $R^3$ may be 1 or more or zero. When there are a plurality of them, the substituents $R^3$ may be the same or different.

The substituent $R^3$ is, for instance, a halogen, OH, $OR^4$, $NH_2$, $NHR^4$, $NR^4R^5$, SH, $SR^4$, or an oxo group (=O).

For instance, $R^4$ and $R^5$ are each independently a substituent or a protecting group and may be the same or different. Examples of the substituent include a halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, or silyloxyalkyl. The same applies to the following. The substituent $R^3$ may be each substituent listed above.

The above protecting group is, for instance, a functional group that converts a highly reactive functional group to an inactive one. Examples include known protecting groups. For instance, the disclosure of a literature (J. F. W. McOmie, "Protecting Groups in Organic Chem-istry," Plenum Press, London and New York, 1973) may be incorporated for the above protecting group. Examples of the above protecting group include, but are not limited to, a tert-butyldimethylsilyl group (TBDMS), bis(2-acetoxyethyloxy)methyl group (ACE), triisopropylsilyloxymethyl group (TOM), 1-(2-cyanoethoxy)ethyl group (CEE), 2-cyanoethoxymethyl group (CEM), tolylsulfonylethoxymethyl group (TEM), or dimethoxytrityl group (DMTr). When $R^3$ is $OR^4$, examples of the above protecting group include, but are not particularly limited to, a TBDMS group, ACE group, TOM group, CEE group, CEM group, or TEM group. Other examples include a silyl-containing group. The same applies to the following.

In formula (III), $L^1$ is an alkylene chain containing n atoms. A hydrogen atom on any carbon atom of the alkylene may be substituted or unsubstituted by OH, $OR^a$, NH $NHR^a$ $NR^aR^b$, SH, or $SR^a$. Alternatively, $L^1$ may be a polyether chain in which at least one carbon atom of the alkylene chain is replaced by an oxygen atom. The above polyether chain is, for instance, polyethylene glycol. When $Y^1$ is NH, O, or S, an $L^1$ atom bonded to $Y^1$ is carbon and an $L^1$ atom bonded to $OR^1$ is carbon while oxygen atoms are not next to each other. That is, when $Y^1$ is O, for instance, this oxygen atom is not next to an oxygen atom of $L^1$ and the oxygen atom of $OR^1$ is not next to an oxygen atom of $L^1$.

In formula (III), $L^2$ is an alkylene chain containing m atoms. A hydrogen atom on any carbon atom of the alkylene may be substituted or unsubstituted by, for instance, OH, $OR^c$, $NH_2$, $NHR^c$, $NR^cR^d$, SH, or $SR^c$. Alternatively, $L^2$ may be a polyether chain in which at least one carbon atom of the alkylene chain is replaced by an oxygen atom. When $Y^2$ is NH, O, or S, an $L^2$ atom bonded to $Y^2$ is carbon and an $L^2$ atom bonded to $OR^2$ is carbon while oxygen atoms are not next to each other. That is, when $Y^2$ is O, for instance, this oxygen atom is not next to an oxygen atom of $L^2$ and the oxygen atom of $OR^2$ is not next to an oxygen atom of $L^2$.

n of $L^1$ and m of $L^2$ are not particularly limited and the lower limit of each is, for instance, 0 and the upper limit is also not particularly limited. Then, n and m may be set, if appropriate, depending on the desired lengths of the linkers $Lx_1$ and $Lx_2$. From the viewpoints of production cost and yield, for instance, n and m are each preferably from 0 to 30, more preferably from 0 to 20, and still more preferably from 0 to 15. n and m may be the same (n=m) or different. For instance, n+m is from 0 to 30, preferably from 0 to 20, and more preferably from 0 to 15.

For instance, $R^a$, $R^b$, $R^c$, and $R^d$ are each independently a substituent or a protecting group. The substituent and the protecting group are, for instance, as described above.

In formula (III), hydrogen atoms may be, for instance, each independently substituted by a halogen such as Cl, Br, F, and I.

In a preferred example, the above linker may be represented by any of formulas (IV-1) to (IV-9) or may comprise one or two or more non-nucleotide residues represented by any of formulas (IV-1) to (IV-9). In the formula below, q is an integer of 0 to 10. In the formulas below, n and m are the same as formula (III). Specifically, for instance, in formula (IV-1), n=8; in formula (IV-2), n=3; in formula (IV-3), n=4 or 8; in formula (IV-4), n=7 or 8; in formula (IV-5), n=3 and m=4; in formula (IV-6), n=8 and m=4; in formula (IV-7), n=8 and m=4; in formula (IV-8), n=5 and m=4; and in formula (IV-9), q=1 and m=4.

(IV-1)

(IV-2)

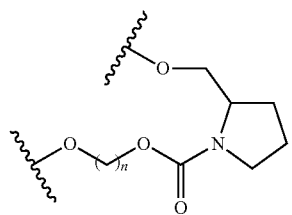

(IV-3)

(IV-4)

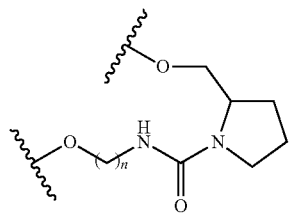

(IV-5)

(IV-6)

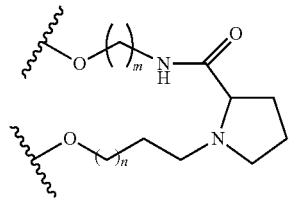

(IV-7)

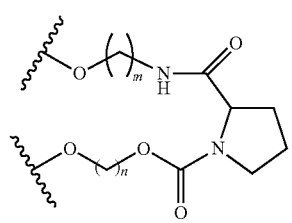

(IV-8)

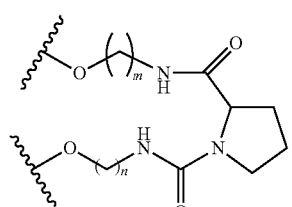

(IV-9)

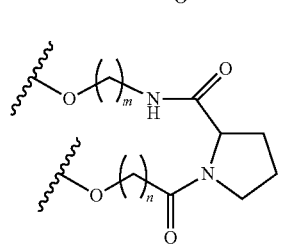

In an example, the above linker may be represented by formula (V) or (VI) or may comprise one or two or more non-nucleotide residues represented by formula (V) or (VI).

(V)

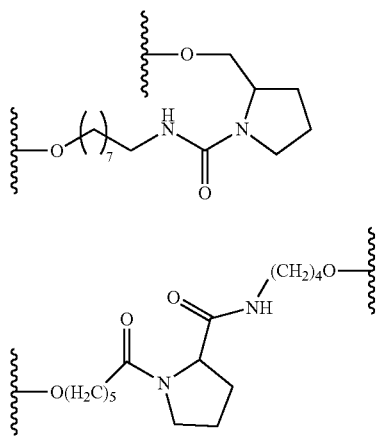

(VI)

In an example, the first RNA region (Xs, XXs) may be connected to the linker $Lx_1$ on the position-2 carbon atom side in formula (VI) and the second RNA region (Xa, $XXa_3$) may be connected to the linker $Lx_1$ on the position-1 nitrogen atom side in the formula (VI); and the third RNA region ($Ya_3$, YYa) may be connected to the linker $Lx_2$ on the position-2 carbon atom side and the fourth RNA region (Ys, YYs) may be connected to the linker $Lx_2$ on the position-1 nitrogen atom side in formula (VI).

The linker represented by formula (VI) may be an optically active substance represented by formula (VI-1) or (VI-2):

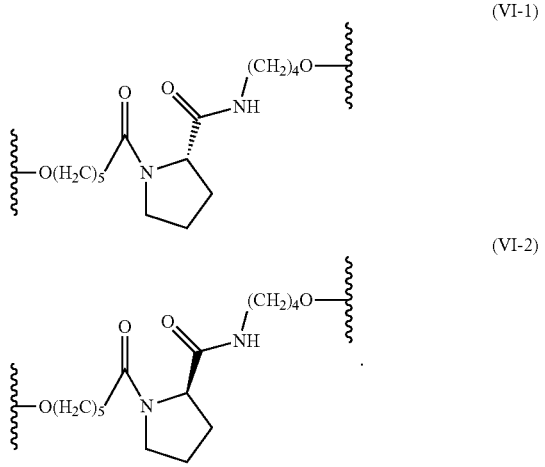

(VI-1)

(VI-2)

In the first and second single-stranded oligoRNA molecules, Xa is complementary to a 3'-side region of Xs and $Ya_3$ is complementary to Ys. Due to this, in the first single-stranded oligoRNA molecule, Xa is folded over Xs and Xa and Xs are self-annealed to form a double strand. Likewise, in the second single-stranded oligoRNA molecule, Ys is folded over $Ya_3$ and Ys and $Ya_3$ are self-annealed to form a double strand.

In the first and second single-stranded oligoRNA molecules, YYa is complementary to a 5'-side region of YYs and $XXa_3$ is complementary to XXs. Due to this, in the first single-stranded oligoRNA molecule, $XXa_3$ is folded over XXs and $XXa_3$ and XXs are self-annealed to form a double strand. Likewise, in the second single-stranded oligoRNA molecule, YYa is folded over YYs and YYa and YYs are self-annealed to form a double strand.

The above linkers are each likely to form a β-turn structure. This causes the first single-stranded oligoRNA molecule in formula (I) to adopt a structure folded on the β-turn side due to the linker $Lx_1$. The above should induce a structure in which when Xa and Xs are self-annealed, the distance between the 3' end of Xa and the 5' end (the 5' end of $Ya_1$) of the second single-stranded oligoRNA molecule in formula (II) is likely to become shorter. The same applies to the first and second single-stranded oligoRNA molecules in formulas (A) and (B).

In another example, the linker such as the first linker or the second linker ($Lx_1$ and $Lx_2$ in the above formulas) may be a nucleotide linker containing one or more nucleotide residues. When the linker is a nucleotide linker, the length is not particularly limited. However, it is preferred that the length should not prevent formation of a double strand between sequences before and after the linker, for instance, between the first RNA region and the second RNA region or between the third RNA region and the fourth RNA region. The lengths (the number of nucleotides) and nucleotide sequences of the first and second linkers ($Lx_1$ and $Lx_2$ in the above formulas), which are nucleotide linkers, may be the same or different. The length of each nucleotide linker may be, for instance, 1 or more nucleotides, 2 or more nucleotides, or 3 or more nucleotides and, for instance, 100 or less nucleotides, 80 or less nucleotides, or 50 or less nucleotides. The length of such a nucleotide linker may be, for instance, from 1 to 50 nucleotides, 1 to 30 nucleotides, 3 to 20 nucleotides, 3 to 10 nucleotides, or 3 to 7 nucleotides and, for instance, 1, 2, 3, 4, 5, 6, 7, 8, 9 or 10 nucleotides. The nucleotide linker is not self-complementary and it is preferred that self-annealing should not occur inside the sequence.

When a linker such as the first linker or the second linker ($Lx_1$ and $Lx_2$ in the above formulas) contains an unmodified nucleotide residue(s) and a modified nucleotide residue(s) (e.g., a modified ribonucleotide residue(s)), the number of modified nucleotide residues is not particularly limited and may be, for instance, 1 to 5, 1 to 4, or 1 to 3, and may be, for instance, 1 or 2.

Examples of a nucleotide linker include a linker consisting of the RNA sequence: 5'-C-A-C-A-C-C-3', 5'-C-C-A-C-A-C-C-3' or 5'-U-U-C-G-3'. In an example, the first linker and the second linker ($Lx_1$ and $Lx_2$ in the above formulas) are each independently selected from 5'-C-A-C-A-C-C-3', 5'-C-C-A-C-A-C-C-3', and 5'-U-U-C-G-3'. In an example, the first linker consists of the RNA sequence 5'-C-A-C-A-C-C-3' and the second linker consists of the RNA sequence 5'-U-U-C-G-3'.

The first and second single-stranded oligoRNA molecules may be produced using an RNA synthesis process known to those skilled in the art. Examples of the RNA synthesis process known to those skilled in the art include a phosphoramidite method or an H-phosphonate process. In the phosphoramidite method, a ribonucleoside bound to a hydrophobic group of a carrier is extended by a condensation reaction with an RNA amidite (ribonucleoside phosphoramidite) and undergoes oxidation and deprotection, and this condensation reaction with an RNA amidite is repeated to be able to carry out RNA synthesis. The first and second single-stranded oligoRNA molecules in formulas (I) and (II) will be described as an example. The first or second single-stranded oligoRNA molecule may be produced by synthesizing a sequence (Xa, Ys) from the 3' end side to a residue before a linker by using an RNA synthesis process such as a phosphoramidite method; forming the linker by bonding to a non-nucleotide residue such as a cyclic amine derivative having a pyrrolidine backbone or a piperidine backbone; and then, further synthesizing a sequence (Xs or $Ya_3$, $Ya_2$, and $Ya_1$) from the end of the liker to the 5' end in this order. Alternatively, the first or second single-stranded oligoRNA molecule may be produced by synthesizing a sequence (Xa, Ys) from the 3' end side to a residue before a nucleotide linker by using an RNA synthesis process such as a phosphoramidite method; subsequently synthesizing a sequence of the nucleotide linker; and further synthesizing a sequence (Xs or $Ya_3$, $Ya_2$, and $Ya_1$) from the end of the nucleotide linker to the 5' end in this order. When a non-nucleotide linker and a nucleotide linker are used in combination or when the first and second single-stranded oligoRNA molecules in formulas (A) and (B) are used, substantially the same procedure as described above is applicable to the production. Any RNA amidite can be used. For instance, it is possible to use any general-purpose RNA amidite having, at a hydroxyl group at position 2, a variety of protecting groups such as a t-butyldimethylsilyl group (TBDMS), triisopropylsilyloxymethyl group (TOM), bis(2-acetoxyethoxy)methyl group (ACE), 1-(2-cyanoethoxy)ethyl group (CEE), 2-cyanoethoxymethyl group (CEM), tolylsulfonylethoxymethyl group (TEM), or dimethoxytrityl group (DMTr). In addition, any solid-phase carrier may be used during RNA synthesis, including a polystyrene-based carrier, an acrylamide-based carrier, or a glass carrier. The carrier may be in any form such as a bead, plate, chip, or tube. Examples of the carrier include, but are not limited to, polystyrene beads such as NittoPhase® HL rG(ibu) or rU (KINOVATE).

Among the above linkers, a cyclic amine derivative for formation of a non-nucleotide linker is a monomer for RNA synthesis and has, for instance, a structure represented by formula (VII) below. This cyclic amine derivative corresponds basically to the structure of each linker described above, and the description about the linker structure is thus applied to this cyclic amine derivative. This linker-forming cyclic amine derivative can be used as, for instance, an amidite for automated nucleic acid synthesis, and is, for instance, applicable to a common automated nucleic acid synthesizer.

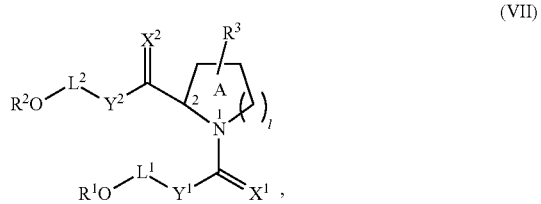

(VII)

wherein
$X^1$ and $X^2$ are each independently $H_2$, O, S, or NH;
$Y^1$ and $Y^2$ are each independently a single bond, $CH_2$, NH, O, or S;
$R^1$ and $R^2$ are each independently H, a protecting group, or a phosphate protecting group;
$R^3$ is a hydrogen atom or a substituent bonded to C-3, C-4, C-5, or C-6 on ring A;
$L^1$ is an alkylene chain containing n atoms where a hydrogen atom on any alkylene carbon atom is optionally substituted or unsubstituted by OH, $OR^a$, $NH_2$, $NHR^a$, $NR^aR^b$, SH, or $SR^a$ or $L^1$ is a polyether chain in which at least one carbon atom of the alkylene chain is replaced by an oxygen atom, where when $Y^1$ is NH, O, or S, an $L^1$ atom bonded to $Y^1$ is carbon and an $L^1$ atom bonded to $OR^1$ is carbon while oxygen atoms are not next to each other;
$L^2$ is an alkylene chain containing m atoms where a hydrogen atom on any alkylene carbon atom is optionally substituted or unsubstituted by OH, $OR^c$, $NH_2$, $NHR^c$, $NR^cR^d$, SH, or $SR^c$ or
$L^2$ is a polyether chain in which at least one carbon atom of the alkylene chain is replaced by an oxygen atom, where when $Y^2$ is NH, O, or S, an $L^2$ atom bonded to $Y^2$ is carbon and an $L^2$ atom bonded to $OR^2$ is carbon while oxygen atoms are not next to each other;
$R^a$, $R^b$, $R^c$, and $R^d$ are each independently a substituent or a protecting group;
l is 1 or 2;
m is an integer of 0 to 30;
n is an integer of 0 to 30;
ring A is provided such that a carbon atom other than C-2 on ring A is optionally replaced by a nitrogen atom, an oxygen atom, or a sulfur atom, and
ring A optionally contains a carbon-carbon double bond or a carbon-nitrogen double bond.

In formula (VII), the description of formula (III) can be cited for the same sites as in formula (III). Specifically, all the description of formula (III) is cited to, for instance, $X^1$, $X^2$, $Y^1$, $Y^2$, $R^3$, $L^1$, $L^2$, l, m, n, and ring A in formula (VII).

As described above, $R^1$ and $R^2$ in formula (VII) are each independently H, a protecting group, or a phosphate protecting group.

The above protecting group is, for instance, similar to those described for formula (III). Specifically, the protecting group may be selected from, for instance, group I. Examples of the group I include a dimethoxytrityl (DMTr) group, a TBDMS group, an ACE group, a TOM group, a CEE group, a CEM group, a TEM group, and a silyl-containing group represented by each of the following formulas; and particularly preferably, either a DMTr group or the silyl-containing group:

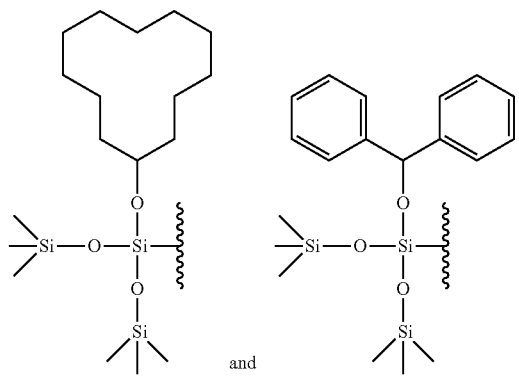

and

The above phosphate protecting group may be represented by, for instance, the following formula:

—P($OR^6$)($NR^7R^8$).

In the above formula, $R^6$ is a hydrogen atom or any substituent. For instance, $R^6$ is preferably a hydrocarbon group. The hydrocarbon group may be substituted or unsubstituted by an electron-withdrawing group. Examples of $R^6$ include a halogen, haloalkyl, heteroaryl, hydroxyalkyl, alkoxyalkyl, aminoalkyl, silyl, silyloxyalkyl, heterocyclylalkenyl, heterocyclylalkyl, heteroarylalkyl, and alkyl, alkenyl, alkynyl, aryl, arylalkyl, cycloalkyl, cycloalkenyl, cycloalkylalkyl, cyclylalkyl and other hydrocarbons. Further, $R^6$ may be substituted or unsubstituted by an electron-withdrawing group. Specific examples of $R^6$ include a Q-cyanoethyl group, a nitrophenylethyl group, or a methyl group.

$R^7$ and $R^8$ are each a hydrogen atom or any substituent and may be the same or different. For instance, $R^7$ or $R^8$ is preferably a hydrocarbon group. The hydrocarbon group may be substituted or unsubstituted further by any substituent. For instance, the above hydrocarbon group is as listed for the above-described $R^6$ and is preferably a methyl group, an ethyl group, or an isopropyl group. In this example, specific examples of —$NR^7R^8$ include a diisopropylamino group, a diethylamino group, or an ethylmethylamino group. Alternatively, the substituents $R^7$ and $R^8$ may be together bonded with a nitrogen (i.e., —$NR^7R^8$ is united) to form a nitrogen-containing ring (e.g., a piperidyl group, a morpholino group).

Specifically, the above phosphate protecting groups may be selected from, for instance, the following group II. Examples of the group II include —$P(OCH_2CH_2CN)(N(i-Pr)_2)$ or —$P(OCH_3)(N(i-Pr)_2)$. In the above formulas, i-Pr represents isopropyl.

For instance, in formula (VII), one of $R^1$ or $R^2$ is H or a protecting group and the other is H or a phosphate protecting group. Preferably, when $R^1$ is the above protecting group, for instance, $R^2$ is preferably H or the above phosphate protecting group. Specifically, it is preferred that when $R^1$ is selected from the above group I, $R^2$ be H or selected from the above group II. In addition, preferably, when $R^1$ is the above phosphate protecting group, for instance, $R^2$ is preferably H or the above protecting group. Specifically, it is preferred that when $R^1$ is selected from the above group II, $R^2$ be H or selected from the above group I.

The above cyclic amine derivative may be represented by any of formulas (VII-1) to (VII-9). In the formulas below, n and m are the same as formula (VII). In the formula below, q is an integer of 0 to 10. Specifically, for instance, in formula (VII-1), n=8; in formula (VII-2), n=3; in formula (VII-3), n=4 or 8; in formula (VII-4), n=7 or 8; in formula (VII-5), n=3 and m=4; in formula (VII-6), n=8 and m=4; in formula (VII-7), n=8 and m=4; in formula (VII-8), n=5 and m=4; and in formula (VII-9), q=1 and m=4.

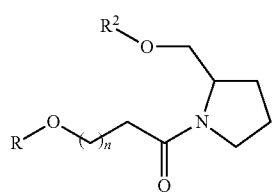

(VII-1)

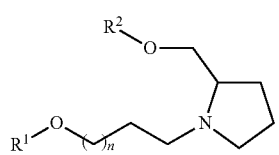

(VII-2)

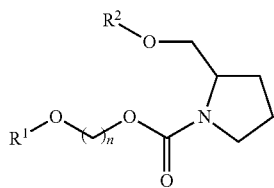

(VII-3)

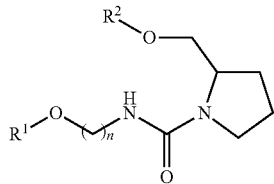

(VII-4)

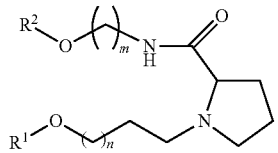

(VII-5)

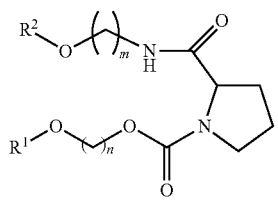

(VII-6)

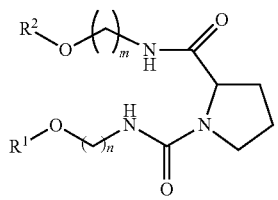

(VII-7)

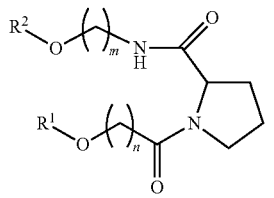

(VII-8)

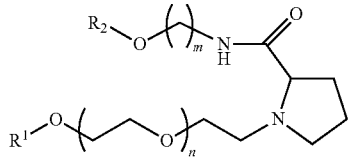

(VII-9)

In an example, the above cyclic amine derivative may be represented by a prolinol derivative represented by formula (VIII) or a proline derivative represented by formula (IX):

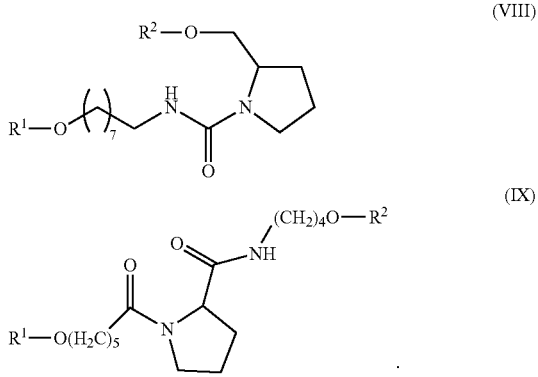

The above cyclic amine derivative may comprise, for instance, a labeled substance such as a stable isotope.

The above cyclic amine derivative may be synthesized, for instance, in accordance with a process of producing a monomer for nucleic acid molecule synthesis as disclosed in WO 2013/027843 or WO 2016/159374.

In our method, the above first single-stranded oligoRNA molecule (e.g., strand 1 in FIG. 1) and second single-stranded oligoRNA molecule (e.g., strand 2 in FIG. 1) may be annealed and ligated to produce a hairpin single-stranded RNA molecule capable of inhibiting expression of a target gene.

In the hairpin single-stranded RNA molecule produced by the method, Xa-$Ya_1$-$Ya_2$-$Ya_3$, which is generated by the ligation step, contains a gene expression-inhibiting sequence for the target gene. A gene expression-inhibiting sequence may be comprised in Xa, Xa-$Ya_1$, Xa-$Ya_1$-$Ya_2$, or Xa-$Ya_1$-$Ya_2$-$Ya_3$. Likewise, $XXa_3$-$XXa_2$-$XXa_1$-YYa, which is generated by the ligation step, contains a gene expression-inhibiting sequence for the target gene. A gene expression-inhibiting sequence may be comprised in YYa, $XXa_1$-YYa, $XXa_2$-$XXa_1$-YYa, or $XXa_3$-$XXa_2$-$XXa_1$-YYa. The gene expression-inhibiting sequence is preferably the whole or part of a sense or antisense sequence of mRNA transcribed from the target gene. Xa-$Ya_1$, which is generated by the ligation step, is complementary to Xs and Xs may thus contain a gene expression-inhibiting sequence for the target gene. Likewise, $XXa_1$-YYa is complementary to YYs and YYs may thus contain a gene expression-inhibiting sequence for the target gene.

The above hairpin single-stranded RNA molecule may contain one or two or more gene expression-inhibiting sequences. The above hairpin single-stranded RNA molecule may have, for instance, the same two or more gene expression-inhibiting sequences for the same target gene, may have two or more different gene expression-inhibiting sequences for the same target, or may have two or more different gene expression-inhibiting sequences for different target genes. The hairpin single-stranded RNA molecule having two or more gene expression-inhibiting sequences for different target genes is useful for inhibiting expression of two or more different target genes. The "gene" refers to a genome region from which mRNA is transcribed, and may be a protein-coding region or an RNA-coding region.

The hairpin single-stranded RNA molecule has an ability to inhibit expression of a target gene through a gene expression-inhibiting sequence. The target gene expression inhibiting using a hairpin single-stranded RNA molecule is preferably mediated, but not limited to, by RNA interference. The RNA interference is a phenomenon that generally speaking, a long double-stranded RNA (dsRNA) is cleaved in a cell, by Dicer, into an about 19- to 21-bp short double-stranded RNA (siRNA: small interfering RNA), the 3' end of which protrudes; one of the single-stranded RNA binds to a target mRNA; and the target mRNA is degraded so that translation of the target mRNA is repressed, which makes it possible to inhibit expression of a target gene derived from the target mRNA. For instance, various kinds of a single-stranded RNA sequence comprised in siRNA bound to a target mRNA have been reported in accordance with the kinds of target gene. For instance, a single-stranded RNA sequence (preferably, an antisense sequence) comprised in siRNA can be used as a gene expression-inhibiting sequence. A hairpin single-stranded RNA molecule produced by our method can inhibit expression of a target gene while cleaved in vivo to generate siRNA. A hairpin single-stranded RNA molecule can be used for treatment or prophylaxis of disease or disorder involving expression or an increase in expression of a target gene.

The gene expression-inhibiting sequence has preferably from 19 to 30, more preferably from 19 to 27, and, for instance, 19, 20, 21, 22, or 23 nucleotides in length. The gene expression-inhibiting sequence preferably consists of an RNA sequence completely identical or completely complementary to at least part of mRNA sequence of the target gene. The gene expression-inhibiting sequence may be designed for the nucleotide sequence of a target gene by a conventional procedure.

The target gene may be any gene and may be, for instance, any disease-related gene. It is preferred that the target gene be derived from the same biological species as a subject subjected to gene expression inhibiting in vivo or in a cell, tissue, organ or the like by the hairpin single-stranded RNA molecule. Examples may include those derived from animals (e.g., mammals (e.g., humans, chimpanzees, gorillas and other primates, horses, cows, pigs, sheep, goats, camels, donkeys and other domestic animals, dogs, cats, rabbits and other companion animals, mice, rats, guinea pigs and other rodents), fish, and insects), plants, fungi or the like. Examples of the target gene include, but are not particularly limited to, TGF-β1 gene, GAPDH gene, LAMA1 gene, or LMNA gene. The mRNA sequence of human TGF-β1 (transforming growth factor-β1) gene is accessible based on, for instance, GenBank (NCBI) Accession No. NM_000660 (NCBI Gene ID: 7040). The mRNA sequence of human GAPDH (glyceraldehyde-3-phosphate dehydrogenase) gene is accessible based on, for instance, GenBank (NCBI) Accession No. NM_002046 (NCBI Gene ID: 2597). The mRNA sequence of human LAMA1 gene is accessible based on, for instance, GenBank Accession No. NM_005559 (NCBI Gene ID: 284217). The mRNA sequence of human LMNA gene is accessible based on, for instance, GenBank Accession No. NM_170707 (NCBI Gene ID: 4000). When the target gene is TGF-β1 gene, a hairpin single-stranded RNA molecule produced by our method inhibit expression of TGF-β1 gene in vivo. Such a hairpin single-stranded RNA molecule can be used, through TGF-β1 gene expression inhibiting, to treat or prevent disease or disorder involving expression or an increase in expression of TGF-β1 gene such as lung fibrosis and/or acute pulmonary disease. Likewise, each hairpin single-stranded RNA molecule capable of inhibiting expression of other target genes such as GAPDH gene, LAMA1 gene, and LMNA gene can be used, through each target gene expression inhibiting, to treat or prevent disease or disorder involving expression or an increase in expression of the target gene.

Figure 2:
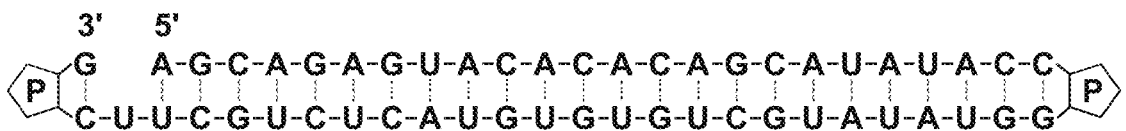
FIG. 2 is a schematic diagram of an ssTbRNA molecule (SEQ ID NO: 1). P represents a proline derivative. Positions 29 (U) to 47 (C) of SEQ ID NO: 1 correspond to an active sequence (a gene expression-inhibiting sequence for TGF-β1 gene; an antisense sequence).

One instance of the hairpin single-stranded RNA molecule produced by our method and is capable of inhibiting expression of a target gene is an RNA molecule consisting of the nucleotide sequence set forth in SEQ ID NO: 1 in which nucleotides (ribonucleotide residues) at positions 24 and 25 are connected via a linker ($Lx_1$) and nucleotides (ribonucleotide residues) at positions 50 and 51 are connected via a linker ($Lx_2$) (e.g., FIG. 2). Such a hairpin single-stranded RNA molecule comprising the nucleotide sequence set forth in SEQ ID NO: 1 comprises, from the 5' end-to-3' end direction, an RNA sequence consisting of the nucleotide sequence set forth in SEQ ID NO: 2, the former linker (a non-nucleotide linker, a nucleotide linker, or a combination thereof: $Lx_1$ in FIG. 1), an RNA sequence consisting of the nucleotide sequence set forth in SEQ ID NO: 3, the above linker (a non-nucleotide linker, a nucleotide linker, or a combination thereof, $Lx_2$ in FIG. 1), and a nucleotide G (guanine). The above hairpin single-stranded RNA molecule comprising the nucleotide sequence set forth in SEQ ID NO: 1 comprises a gene expression-inhibiting sequence for a target gene, namely TGF-β1 gene. The sequence from position 29 to position 47 of the nucleotide sequence set forth in SEQ ID NO: 1 corresponds to a gene expression-inhibiting sequence (active sequence; SEQ ID NO: 50). We provide a method of producing a hairpin single-stranded RNA molecule comprising this gene expression-inhibiting sequence.

The below-described Table 1 lists instances of the first single-stranded oligoRNA molecule (strand 1) and the second single-stranded oligoRNA molecule (strand 2) for the manufacture of such an RNA molecule. In sequences of the first single-stranded oligoRNA molecule (strand 1) and the second single-stranded oligoRNA molecule (strand 2) listed in Table 1, a P (proline derivative)-containing linker may be replaced by any linker such as the above another non-nucleotide linker or nucleotide linker. In an example, the first single-stranded oligoRNA molecule preferably has an uracil (U) or adenine (A) at the 3' end, and the second single-stranded oligoRNA molecule preferably has an uracil (U) or adenine (A) at the 5' end.

Examples of a pair of the particularly preferably first single-stranded oligoRNA molecule and second single-stranded oligoRNA molecule for production of a hairpin single-stranded RNA molecule comprising the nucleotide sequence set forth in SEQ ID NO: 1 include the following:

(1) a combination of the first single-stranded oligoRNA molecule consisting of the nucleotide sequence set forth in SEQ ID NO: 7 in which ribonucleotide residues at positions 24 and 25 are connected via the first linker ($Lx_1$) and the second single-stranded oligoRNA molecule consisting of the nucleotide sequence set forth in SEQ ID NO: 6 in which ribonucleotide residues at positions 10 and 11 are connected via the second linker ($Lx_2$);

(2) a combination of the first single-stranded oligoRNA molecule consisting of the nucleotide sequence set forth in SEQ ID NO: 19 in which ribonucleotide residues at positions 24 and 25 are connected via the first linker ($Lx_1$) and the second single-stranded oligoRNA molecule consisting of the nucleotide sequence set forth in SEQ ID NO: 18 in which ribonucleotide residues at positions 16 and 17 are connected via the second linker ($Lx_2$);

(3) a combination of the first single-stranded oligoRNA molecule consisting of the nucleotide sequence set forth in SEQ ID NO: 27 in which ribonucleotide residues at positions 24 and 25 are connected via the first linker ($Lx_1$) and the second single-stranded oligoRNA molecule consisting of the nucleotide sequence set forth in SEQ ID NO: 26 in which ribonucleotide residues at positions 20 and 21 are connected via the second linker ($Lx_2$);

(4) a combination of the first single-stranded oligoRNA molecule consisting of the nucleotide sequence set forth in SEQ ID NO: 29 in which ribonucleotide residues at positions 24 and 25 are connected via the first linker ($Lx_1$) and the second single-stranded oligoRNA molecule consisting of the nucleotide sequence set forth in SEQ ID NO: 28 in which ribonucleotide residues at positions 21 and 22 are connected via the second linker ($Lx_2$);

(5) a combination of the first single-stranded oligoRNA molecule consisting of the nucleotide sequence set forth in SEQ ID NO: 31 in which ribonucleotide residues at positions 24 and 25 are connected via the first linker ($Lx_1$) and the second single-stranded oligoRNA molecule consisting of the nucleotide sequence set forth in SEQ ID NO: 30 in which ribonucleotide residues at positions 22 and 23 are connected via the second linker ($Lx_2$); and (6) a combination of the first single-stranded oligoRNA molecule consisting of the nucleotide sequence set forth in SEQ ID NO: 33 in which ribonucleotide residues at positions 24 and 25 are connected via the first linker ($Lx_1$) and the second single-stranded oligoRNA molecule consisting of the nucleotide sequence set forth in SEQ ID NO: 32 in which ribonucleotide residues at positions 23 and 24 are connected via the second linker ($Lx_2$).

These first single-stranded oligoRNA molecules each comprise U or A at the 3' end (3' end of Xa). These second single-stranded oligoRNA molecules each comprise U or A at the 5' end (5' end of $Ya_1$).

For instance, regarding (1) the first single-stranded oligoRNA molecule, the wording "ribonucleotide residues at positions 24 and 25 are connected via the first linker ($Lx_1$)" means that the ribonucleotide residue at position 24 (nucleotide: C) and the ribonucleotide residue at position 25 (nucleotide: G) of the nucleotide sequence set forth in SEQ ID NO: 19 are connected via the first linker $Lx_1$ in the first single-stranded oligoRNA molecule. The expression "ribonucleotide residues at positions X and Y are connected via z" with respect to the single-stranded oligoRNA molecule and the hairpin single-stranded RNA molecule should be construed accordingly.

The linkers $Lx_1$ and $Lx_2$ in the first and second single-stranded oligoRNA molecules in (1) to (6) are preferably represented by formula (VI) including formula (VI-1) or formula (VI-2).

In a preferred example, the first and second single-stranded oligoRNA molecules in (1) to (6) have, as $Lx_1$ and $Lx_2$, linkers represented by formula (VI). Xa of formula (I) may be connected to the linker $Lx_1$ on the position-1 nitrogen atom side in formula (VI) and Xs may be connected to the linker $Lx_1$ on the position-2 carbon atom side. Ys of formula (VI) may be connected to the linker $Lx_2$ on the position-1 nitrogen atom side in formula (VI) and $Ya_3$ may be connected to the linker $Lx_2$ on the position-2 carbon atom side.

We provide single-stranded oligoRNA molecules that can be used, as the first and second single-stranded oligoRNA molecules, to produce a hairpin single-stranded RNA molecule in accordance with our method.

Examples of a single-stranded oligoRNA molecule used to produce a hairpin single-stranded RNA molecule capable of inhibiting expression of a target gene, namely TGF-β1 gene include, but are not limited to (a) to (l):

(a) a single-stranded oligoRNA molecule consisting of the nucleotide sequence set forth in SEQ ID NO: 7 in which ribonucleotide residues at positions 24 and 25 are connected via a linker;
(b) a single-stranded oligoRNA molecule consisting of the nucleotide sequence set forth in SEQ ID NO: 6 in which ribonucleotide residues at positions 10 and 11 are connected via a linker;
(c) a single-stranded oligoRNA molecule consisting of the nucleotide sequence set forth in SEQ ID NO: 19 in which ribonucleotide residues at positions 24 and 25 are connected via a linker;
(d) a single-stranded oligoRNA molecule consisting of the nucleotide sequence set forth in SEQ ID NO: 18 in which ribonucleotide residues at positions 16 and 17 are connected via a linker;
(e) a single-stranded oligoRNA molecule consisting of the nucleotide sequence set forth in SEQ ID NO: 27 in which ribonucleotide residues at positions 24 and 25 are connected via a linker;
(f) a single-stranded oligoRNA molecule consisting of the nucleotide sequence set forth in SEQ ID NO: 26 in which ribonucleotide residues at positions 20 and 21 are connected via a linker;
(g) a single-stranded oligoRNA molecule consisting of the nucleotide sequence set forth in SEQ ID NO: 29 in which ribonucleotide residues at positions 24 and 25 are connected via a linker;
(h) a single-stranded oligoRNA molecule consisting of the nucleotide sequence set forth in SEQ ID NO: 28 in which ribonucleotide residues at positions 21 and 22 are connected via a linker;
(i) a single-stranded oligoRNA molecule consisting of the nucleotide sequence set forth in SEQ ID NO: 31 in which ribonucleotide residues at positions 24 and 25 are connected via a linker;
(j) a single-stranded oligoRNA molecule consisting of the nucleotide sequence set forth in SEQ ID NO: 30 in which ribonucleotide residues at positions 22 and 23 are connected via a linker;
(k) a single-stranded oligoRNA molecule consisting of the nucleotide sequence set forth in SEQ ID NO: 33 in which ribonucleotide residues at positions 24 and 25 are connected via a linker; and
(l) a single-stranded oligoRNA molecule consisting of the nucleotide sequence set forth in SEQ ID NO: 32 in which ribonucleotide residues at positions 23 and 24 are connected via a linker.

In a preferred example, the single-stranded oligoRNA molecules: (a) and (b); (c) and (d); (e) and (f); (g) and (h); (i) and (j); or (k) and (l) are used in combination for a method of producing a hairpin single-stranded RNA molecule.

Figure 17:
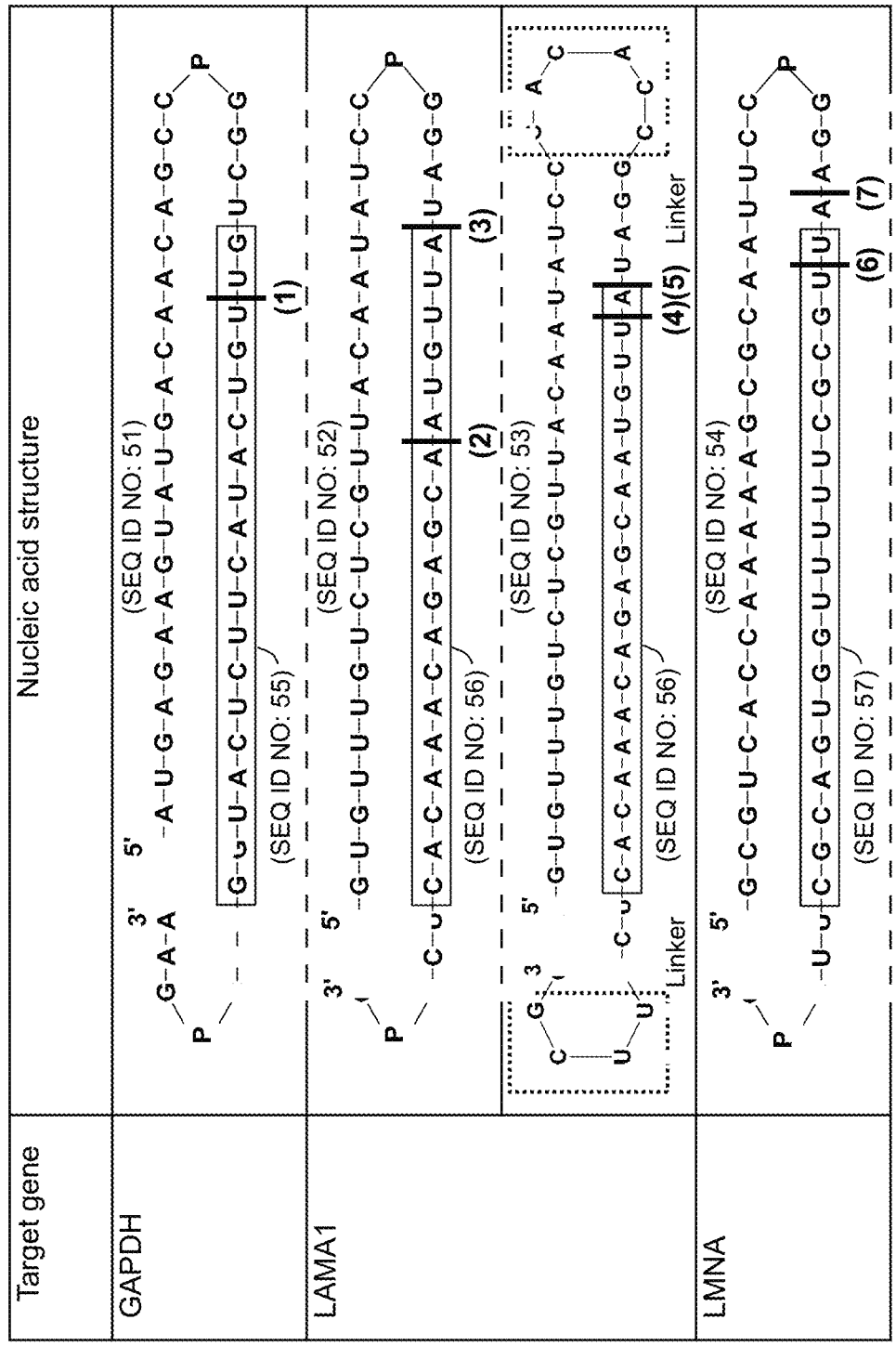
FIG. 17 shows hairpin single-stranded RNA molecules containing a gene expression-inhibiting sequence for GAPDH gene, LAMA1 gene, or LMNA gene and their segmentation positions. (1) to (7) indicate the segmentation positions. The gene expression-inhibiting sequence (active sequence/antisense sequence) for each gene is boxed.

Other examples of a hairpin single-stranded RNA molecule for a target gene such as GAPDH gene, LAMA1 gene, or LMNA gene as produced by a method are depicted in FIG. 17. An instance of a hairpin single-stranded RNA molecule for GAPDH gene is an RNA molecule consisting of the nucleotide sequence set forth in SEQ ID NO: 51 where nucleotides (ribonucleotide residues) at positions 22 and 23 are connected via the first linker ($Lx_1$) and nucleotides (ribonucleotide residues) at positions 48 and 49 are connected via the second linker ($Lx_2$). An instance of a hairpin single-stranded RNA molecule for LAMA1 gene is an RNA molecule consisting of the nucleotide sequence set forth in SEQ ID NO: 52 where nucleotides (ribonucleotide residues) at positions 24 and 25 are connected via the first linker ($Lx_1$) and nucleotides (ribonucleotide residues) at positions 50 and 51 are connected via the second linker ($Lx_2$). Another instance of a hairpin single-stranded RNA molecule for LAMA1 gene is an RNA molecule consisting of a nucleotide sequence set forth in SEQ ID NO: 53 where nucleotides (ribonucleotide residues) at positions 24 and 31 are connected via the first nucleotide linker ($Lx_1$) and nucleotides (ribonucleotide residues) at positions 56 and 61 are connected via the second nucleotide linker ($Lx_2$). An instance of a hairpin single-stranded RNA molecule for LMNA gene is an RNA molecule consisting of the nucleotide sequence set forth in SEQ ID NO: 54 where nucleotides (ribonucleotide residues) at positions 24 and 25 are connected via the first linker ($Lx_1$) and nucleotides (ribonucleotide residues) at positions 50 and 51 are connected via the second linker ($Lx_2$). FIG. 17 illustrates examples of a gene expression-inhibiting sequence for a target gene, namely GAPDH gene, LAMA1 gene, or LMNA gene (an antisense sequence; SEQ ID NO: 55, 56, or 57, respectively). We provide a method of producing a hairpin single-stranded RNA molecule comprising any of these gene expression-inhibiting sequences.

Examples of a single-stranded oligoRNA molecule used to produce a hairpin single-stranded RNA molecule capable of inhibiting expression of a target gene, namely GAPDH gene include, but are not limited to (m) or (n):

(m) a single-stranded oligoRNA molecule consisting of the nucleotide sequence set forth in SEQ ID NO: 37 in which ribonucleotide residues at positions 22 and 23 are connected via a linker; and
(n) a single-stranded oligoRNA molecule consisting of the nucleotide sequence set forth in SEQ ID NO: 36 in which ribonucleotide residues at positions 20 and 21 are connected via a linker.

In a preferred example, the single-stranded oligoRNA molecules of (m) and (n) may be used in combination for our method of producing a hairpin single-stranded RNA molecule.

Examples of a single-stranded oligoRNA molecule used to produce a hairpin single-stranded RNA molecule capable of inhibiting expression of a target gene, namely LAMA1 gene include, but are not limited to (o) to (v):

(o) a single-stranded oligoRNA molecule consisting of the nucleotide sequence set forth in SEQ ID NO: 39 in which ribonucleotide residues at positions 24 and 25 are connected via a linker;
(p) a single-stranded oligoRNA molecule consisting of the nucleotide sequence set forth in SEQ ID NO: 38 in which ribonucleotide residues at positions 16 and 17 are connected via a linker;
(q) a single-stranded oligoRNA molecule consisting of the nucleotide sequence set forth in SEQ ID NO: 41 in which ribonucleotide residues at positions 24 and 25 are connected via a linker;
(r) a single-stranded oligoRNA molecule consisting of the nucleotide sequence set forth in SEQ ID NO: 40 in which ribonucleotide residues at positions 22 and 23 are connected via a linker;
(s) a single-stranded oligoRNA molecule consisting of the nucleotide sequence set forth in SEQ ID NO: 43 in which ribonucleotide residues at positions 24 and 31 are connected via a nucleotide linker;

(t) a single-stranded oligoRNA molecule consisting of the nucleotide sequence set forth in SEQ ID NO: 42 in which ribonucleotide residues at positions 21 and 26 are connected via a nucleotide linker;
(u) a single-stranded oligoRNA molecule consisting of the nucleotide sequence set forth in SEQ ID NO: 45 in which ribonucleotide residues at positions 24 and 31 are connected via a nucleotide linker; and
(v) a single-stranded oligoRNA molecule consisting of the nucleotide sequence set forth in SEQ ID NO: 44 in which ribonucleotide residues at positions 22 and 27 are connected via a nucleotide linker.

In a preferred example, the single-stranded oligoRNA molecules: (o) and (p); (q) and (r); (s) and (t); or (u) and (v) can be used in combination for a method of producing a hairpin single-stranded RNA molecule.

Examples of a single-stranded oligoRNA molecule used to produce a hairpin single-stranded RNA molecule capable of inhibiting expression of a target gene, namely LMNA gene include, but are not limited to (w) to (z):
(w) a single-stranded oligoRNA molecule consisting of the nucleotide sequence set forth in SEQ ID NO: 47 in which ribonucleotide residues at positions 24 and 25 are connected via a linker;
(x) a single-stranded oligoRNA molecule consisting of the nucleotide sequence set forth in SEQ ID NO: 46 in which ribonucleotide residues at positions 21 and 22 are connected via a linker;
(y) a single-stranded oligoRNA molecule consisting of the nucleotide sequence set forth in SEQ ID NO: 49 in which ribonucleotide residues at positions 24 and 25 are connected via a linker; and
(z) a single-stranded oligoRNA molecule consisting of the nucleotide sequence set forth in SEQ ID NO: 48 in which ribonucleotide residues at positions 23 and 24 are connected via a linker.

In a preferred example, the single-stranded oligoRNA molecules of (w) and (x), or (y) and (z) may be used in combination for the method of producing a hairpin single-stranded RNA molecule.

Each "linker" in the single-stranded oligoRNA molecules (a) to (z) corresponds to the first linker or the second linker. Meanwhile, the above-described linkers may be used therefor. Each nucleotide linker in the single-stranded oligoRNA molecules (s) to (v) may be replaced by each linker (e.g., another nucleotide linker) as described above.

The above first and second single-stranded oligoRNA molecules may be linked by ligation to produce a hairpin single-stranded RNA molecule. The above first and second single-stranded oligoRNA molecules are annealed before the ligation. The annealing reaction may be elicited by mixing the first and second single-stranded oligoRNA molecules in an aqueous medium. During the annealing step, the first and second single-stranded oligoRNA molecules may be mixed in an aqueous medium (usually in water or buffer), and allowed to stand for a certain period (e.g., for 1 to 15 min) or used directly for a ligation reaction. During the annealing step, the first and second single-stranded oligoRNA molecules may be heat-denatured (e.g., heated at a temperature of 90° C. or higher) or maybe not. When heat-denatured, a reaction solution containing the first and second single-stranded oligoRNA molecules may be heated at, for instance, a heat denaturation temperature (e.g., 90° C. or higher), and then reacted and annealed for a certain period at an annealing temperature (typically, a temperature in a range of Tm value±5° C. based on $Ya_1$ sequence of the single-stranded oligoRNA molecule; for instance from 55 to 60° C.). After that, the temperature may be decreased (to, for instance, 4° C.). In annealing without heat denaturation, the first and second single-stranded oligoRNA molecules may be mixed at room temperature (from 15 to 35° C.) and allowed to stand for a certain period (e.g., from 1 min to 1 hours or from 5 to 15 min). In this way, the annealing step may be carried out.

In an example, during the annealing step, the first and second single-stranded oligoRNA molecules are mixed in equal molar quantities in a reaction solution. The "mixed in equal molar quantities" means that the first and second single-stranded oligoRNA molecules are mixed at a molar ratio of from 1:1.1 to 1.1:1.

After the annealing step, an annealing reaction solution containing a double-stranded oligoRNA obtained by annealing the first and second single-stranded oligoRNA molecules is subjected to ligation. A portion of the annealing reaction solution may be added to a ligation reaction solution, or all the volume of annealing reaction solution may be used to prepare a ligation reaction solution. The ligation may be an enzymatic ligation. The enzymatic ligation may be ligation mediated by an RNA ligase, in particular, an Rnl2 family ligase.

The Rnl2 family ligase (a Rnl2 family member) is an enzyme with an RNA nick-sealing activity, namely, a ligase activity in which an RNA nick (a nick in an RNA double strand or RNA-DNA double strand) is filled (sealed) by joining the 3' hydroxyl group (3'-OH) to the 5' phosphate group (5'-$PO_4$) (see, for instance, Nandakumar J. et al., Cell 127, p. 71-84 (2006)). Examples of the Rnl2 family ligase include, but are not limited to, T4 RNA ligase 2, *Trypanosoma* (e.g., *Trypanosoma brucei*) or *Leishmania* (e.g., *Leishmania tarenotolae*) RNA editing ligase (REL), bibliophage KVP40Rnl2, poxvirus AmEPV ligase, baculovirus AcNPV ligase, and baculovirus XcGV ligase, and variants or modified ligases thereof. These ligases are well-known to those skilled in the art, or may be commercially available or obtained in accordance with the teachings of research articles and the like. For instance, T4 RNA ligase 2 is commercially available from New England Biolabs. T4 RNA ligase 2 protein is encoded by gp24.1, a bacteriophage T4 gene. T4 RNA ligase 2 may be isolated in accordance with the disclosures in, for instance, Nandakumar J. and Shuman S., (2005) J. Biol. Chem., 280: 23484-23489; Nandakumar J., et al., (2004) J. Biol. Chem., 279: 31337-31347; and Nandakumar J. and Shuman S., (2004) Mol. Cell, 16: 211-221. The "Rnl2 family ligase" is not limited to isolated naturally occurring ligases and examples include, as long as the ligase has an RNA nick-sealing activity, a recombinant protein, a mutant, a deletion variant (e.g., in a truncated form), a peptide (e.g., a His, HA, c-Myc, V5, or DDDDK tag), a fusion protein, or a modified protein such as a glycosylated or lipidated protein.

The ligation reaction solution may be prepared using components commonly used in ligation or buffer containing the components. The ligation reaction solution may contain, in addition to the above first and second single-stranded oligoRNA molecules, components that can be used in an RNA ligation reaction such as Tris-HC, a divalent metal ion, dithiothreitol (DTT), and adenosine triphosphate (ATP). Examples of the divalent metal ion include, but are not limited to, $Mg^{2+}$ or $Mn^{2+}$. The ligation reaction solution usually contains a divalent metal ion in a salt form, for instance, a metal chloride (e.g., $MgCl_2$, $MnCl_2$).

The first and second single-stranded oligoRNA molecules may be ligated using an RNA ligase or another enzyme which has an activity of joining RNA termini or a dsRNA nick, in particular, an Rnl2 family ligase. A dsRNA ligase may be used as the RNA ligase. The dsRNA ligase is an enzyme with a main activity of joining a nick of a double-stranded RNA (dsRNA). Examples of the dsRNA ligase include, but are not limited to, T4 RNA ligase 2. The T4 RNA ligase 2 catalyzes the formation of a 3' to 5' phosphodiester bond.

An Rnl2 family ligase may be added to a ligation reaction solution; and a double-stranded oligoRNA molecule containing annealed first and second single-stranded oligoRNA molecules and the Rnl2 family ligase may be incubated under conditions allowing for ligation to ligate, into a single strand, the 3' end of the first single-stranded oligoRNA molecule with the 5' end of the second single-stranded oligoRNA molecule (in an antisense strand) constituting the double-stranded oligoRNA molecule.

The first and second single-stranded oligoRNA molecules may be ligated in a ligation reaction solution containing the first and second single-stranded oligoRNA molecules in equal molar quantities. The "containing . . . in equal molar quantities" means that the first and second single-stranded oligoRNA molecules are comprised at a molar ratio of from 1:1.1 to 1.1:1.

The ligation may be carried out in a ligation reaction solution containing the first and second single-stranded oligoRNA molecules each at a concentration of 10 μM or higher, 40 μM or higher, 100 μM or higher, 150 μM or higher, 200 μM or higher, 300 μM or higher, or 500 μM or higher. In an example, the ligation reaction solution may contain the first and second single-stranded oligoRNA molecules each at a concentration of 10,000 μM or less, for instance, 1,000 μM or less, 500 μM or less, or 300 μM or less. In an example, the first and second single-stranded oligoRNA molecules may be used in a ligation reaction solution at a concentration of, for instance, from 50 to 500 μM, from 100 to 300 μM, or from 100 to 250 μM. In an example, the first and second single-stranded oligoRNA molecules at such a concentration may be comprised in a ligation reaction solution containing the first and second single-stranded oligoRNA molecules in equal molar quantities. The first and second single-stranded oligoRNA molecules at a concentration (or quantity) higher than the concentration (or quantity) of the Rnl2 family ligase in a reaction solution may be used to increase efficiency of producing a hairpin single-stranded RNA molecule.

In an example, the ligation reaction solution may contain an Rnl2 family ligase at a concentration of 0.01 U/μL or higher, for instance, 0.01 U/μL or higher, 0.08 U/μL or higher, 0.2 U/μL or higher, or 0.35 U/μL or higher. The ligation reaction solution may contain an Rnl2 family ligase at a concentration of, for instance, 10 U/μL or lower, 1 U/μL or lower, or 0.5 U/μL or lower. In an example, the Rnl2 family ligase at such a concentration may be comprised in a ligation reaction solution containing the first and second single-stranded oligoRNA molecules in equal molar quantities.

In an example, the pH of the ligation reaction solution may be pH 6.5 or higher, for instance, pH 7.0 to 9.0, pH 7.4 or higher, pH 7.4 to 8.6, pH 7.5 to 8.5, or pH 7.5 to 8.0. The ligation reaction solution containing the first and second single-stranded oligoRNA molecules in equal molar quantities may have such a pH.

In an example, the ligation reaction solution contains a divalent metal ion at 1 mM or higher, for instance, 1 to 20 mM, 2 to 10 mM, 3 to 6 mM, or 5 mM. In an example, the ligation reaction solution may contain $Mg^{2+}$ or $Mn^{2+}$ at 1 mM or higher, for instance, 1 to 20 mM, 2 to 10 mM, 3 to 6 mM, or 5 mM and may contain, for instance, $MgCl_2$ at such a concentration. In an example, the divalent metal ion at such a concentration includes in a ligation reaction solution containing the first and second single-stranded oligoRNA molecules in equal molar quantities.

The ligation reaction solution may contain an additional additive(s) such as polyethylene glycol (PEG). Examples of the polyethylene glycol that can be used include PEG6000 to 20000 such as PEG6000, PEG8000, or PEG20000. The ligation reaction solution may contain polyethylene glycol at a quantity of, for instance, 3 to 30 w/v %, 5 to 20 w/v %, 5 to 15 w/v %, or 10 to 30 w/v %. In an example, the polyethylene glycol at such a concentration may be comprised in a ligation reaction solution containing the first and second single-stranded oligoRNA molecules in equal molar quantities. In an example, such polyethylene glycol may be added to and used in a ligation reaction solution containing an RNA ligase at 0.4 U/μL or lower, for instance, 0.01 to 0.4 U/μL, 0.08 to 0.4 U/μL, or 0.1 U/μL or more to less than 0.3 U/μL.

The ligation reaction solution usually contains ATP. The ligation reaction solution contains ATP at a concentration of, for instance, 5 mM or lower, 2 mM or lower, 1 mM or lower, and/or 0.1 mM or higher, or 0.1 to 1.5 mM.

In an example, the ligation reaction solution may contain Tris-HCl and may contain, for instance, Tris-HCl at a concentration of from 10 to 70 mM without limitation. The ligation reaction solution may contain dithiothreitol (DTT) and may contain DTT at a concentration of, for instance, from 0.1 to 5 mM without limitation.

The reaction time for ligation may be time fit for a ligation reaction with a double-stranded oligoRNA containing the first and second single-stranded oligoRNA molecules. The ligation reaction may be carried out for a reaction time of, for instance, 20 min or longer or 30 min or longer, 1 hour or longer, 2 hours or longer, or 3 hours or longer. The reaction time for ligation may be 4 hours or longer, 6 hours or longer, 8 hours or longer, 10 hours or longer, 12 hours or longer, 24 hours or longer, or 48 hours or longer. When the ligation reaction solution used contains the first and second single-stranded oligoRNA molecules at a particularly high concentration (e.g., 100 μM or 200 μM or higher), the ligation reaction may be carried out for a longer period. For instance, when the ligation reaction solution has a pH 7.4 or higher, pH 7.4 to 8.6, pH 7.5 to 8.5, or pH 7.5 to pH 8.0, a longer reaction time (e.g., 4 hours or longer, 12 hours or longer, or 24 hours or longer) may be used. In using a particularly highly concentrated single-stranded oligoRNA molecule, such a longer reaction time may be used.

The ligation step may be conducted while the first and second single-stranded oligoRNA molecules are added stepwise. The "added stepwise" with respect to the first and second single-stranded oligoRNA molecules means that during the ligation step, the first and second single-stranded oligoRNA molecules are added to the reaction solution multiple times with a temporal interval. For instance, the first and second single-stranded oligoRNA molecules and an RNA ligase are incubated over a time fit for a ligation reaction. Next, as an additional reaction step, the first and second single-stranded oligoRNA molecules are further added to perform further ligation reaction. The additional reaction step may be performed once or repeated more than one time. In this way, ligation may be performed while adding the single-stranded RNA molecules stepwise to a reaction system. The additional reaction step may be repeated two, three, four or more times. In this example, the first incubation period (initial reaction time) for ligation of the first and second single-stranded oligoRNA molecules may depend on the above ligation reaction time and may be, for instance, 4 hours or longer, 8 hours or longer, 12 hours or longer, or 24 hours or longer. The incubation period (additional reaction time) after the first and second single-stranded oligoRNA molecules are further added may be, for instance, 4 hours or longer, 8 hours or longer, 12 hours or longer, or 24 hours or longer. In the additional reaction step during the ligation, the additional reaction time per cycle may be the same or different from each other. The initial reaction time during the ligation and the additional reaction time per cycle may be the same or different. When the first and second single-stranded oligoRNA molecules are added stepwise, the concentration of the single-stranded oligoRNA molecule(s) added to the ligation reaction solution for the first time may be the same as above and may be, for instance, 40 µM or higher, 100 µM or higher, 150 µM or higher, or 200 µM or higher. The quantity of single-stranded RNA molecules added to the ligation reaction solution during each additional reaction step may be the same as or different from the quantity (the number of moles) of single-stranded RNA molecules comprised in the initial reaction solution, and may be, for instance, 4 nmol or higher, 10 nmol or higher, 15 nmol or higher, or 20 nmol or higher.

The first and second single-stranded oligoRNA molecules are ligated while added stepwise. This can increase the content of the first and second single-stranded oligoRNA molecules in the reaction solution while reducing a reaction inhibition (a decrease in ligation efficiency) caused by a high concentration of single-stranded RNA molecules. This can increase the yield of the above hairpin single-stranded RNA molecule.

The above reaction conditions may be optionally used in combination. A plurality of conditions selected from the above conditions such as the temperature during the annealing step, the time during the annealing step, the ratio of mixing the first and second single-stranded oligoRNA molecules to be annealed, the quantity (concentration) of the first and second single-stranded oligoRNA molecules in the ligation reaction solution, the kind and usage of enzyme (e.g., an Rnl2 family ligase), the kind and concentration of divalent metal ion, pH, ATP concentration, components added such as PEG and the concentration thereof, the reaction time for ligation, and stepwise addition (supplemental addition) of the first and second single-stranded oligoRNA molecules during the ligation reaction may be optionally combined. For instance, the first and second single-stranded oligoRNA molecules at a relatively high concentration (e.g., from 100 µM to 300 µM) in the above ligation reaction solution may be combined with any of the other conditions. Alternatively, usage (e.g., 0.01 U/µL to 1 U/µL) of enzyme (e.g., an Rnl2 family ligase) may be combined with any of the other conditions.

The ligation reaction conditions may be adjusted as above. In this example, an RNA ligase, in particular, an Rnl2 family ligase in an amount less than the amount of the first and second single-stranded oligoRNA molecules used may be used to relatively or absolutely increase the yield of ligation product. It is possible to use an RNA ligase, in particular, an Rnl2 family ligase in an amount of 10 unit (U) or less, 5 U or less, 4 U or less, 2 U or less, 1 U or less, 0.7 U or less, 0.5 U or less, 0.3 U or less, or 0.1 U or less per nmol (the number of moles) of the first and/or second single-stranded oligoRNA molecules used for the ligation. In an example, the usage of RNA ligase, in particular, an Rnl2 family ligase may be 0.001 unit (U) or higher, 0.01 U or higher, 0.1 U or higher, 0.2 U or higher, or 1 U or higher per quantity (nmol) of the first and/or second single-stranded oligoRNA molecules. The "RNA ligase in an amount of "X" unit or less per nmol (the number of moles) of the first and/or second single-stranded oligoRNA molecules" means that the amount of activity of RNA ligase, in particular, an Rnl2 family ligase is "X" unit or less when compared to one of or both the numbers of moles (nmol) of the first and second single-stranded oligoRNA molecules. In an example, the number of moles (nmol) of the first or second single-stranded oligoRNA molecule, whichever smaller, may be used as a reference to determine the amount of RNA ligase used. The number of moles (nmol) of the first single-stranded oligoRNA molecule may be calculated as the total amount of the first single-stranded oligoRNA molecule added to the ligation reaction system. For instance, when the single-stranded oligoRNA molecule is added stepwise, the number of moles of the first single-stranded oligoRNA molecule in the initial reaction solution during the ligation and the number of moles of the first single-stranded oligoRNA molecule added to the reaction system during the additional reaction step may be totaled as the number of moles.

The temperature of the ligation reaction may be changed depending on the enzyme used (an Rnl2 family ligase) and may be, for instance, 10 to 50° C., 15 to 45° C., 20 to 40° C., 20 to 30° C., or 23 to 28° C. For instance, when T4 RNA ligase 2 is used, the temperature may be 10 to 50° C., 15 to 45° C., 20 to 40° C., 20 to 30° C., or 23 to 28° C.

After completion of the ligation step, the ligation reaction solution contains, at a high proportion, a hairpin single-stranded RNA molecule including a gene expression-inhibiting sequence.

The hairpin single-stranded RNA molecule including a gene expression-inhibiting sequence in the ligation reaction solution may be purified by a method known to those skilled in the art. Examples of the purification technique include, but are not limited to, chromatography such as reverse phase chromatography, reverse phase high performance liquid chromatography (RP-HPLC), ultra-high performance liquid chromatography (UHPLC), or ion exchange chromatography, gel filtration, column purification, polyacrylamide gel electrophoresis (PAGE), or any combination thereof.

In the procedure described in WO 2013/027843, nucleic acid impurities such as short-strand nucleic acid impurities and deletion variants may be generated due to termination of an elongation reaction of a very short strand, thereby causing a decrease in purity of a product of interest in the reaction solution. By contrast, a method according to a preferred example has an advantage from the viewpoint of being able to decrease nucleic acid impurities in the ligation reaction solution after a hairpin single-stranded RNA molecule is produced. A method according to a preferred example can be used to produce a highly stable single-stranded RNA molecule capable of inhibiting gene expression by using general-purpose RNA amidites while decreasing the generation of nucleic acid impurities.

A hairpin single-stranded RNA molecule produce by our method may be used and administered in vivo or intracellularly to inhibit expression of a target gene by a conventional procedure.

We further provide a kit that produces a hairpin single-stranded RNA molecule for inhibiting expression of a target gene, the kit comprising a combination (pair) of single-stranded oligoRNA molecules. Such a kit may be suitably used to put into practice a method of producing a hairpin single-stranded RNA molecule capable of inhibiting expression of a target gene.

In an example, examples of the kit include, but are not limited to, a kit for producing a hairpin single-stranded RNA molecule capable of inhibiting expression of TGF-β1 gene, the kit comprising a combination of single-stranded oligoRNA molecules represented by any of (i) to (vi):

(i) a combination of the first single-stranded oligoRNA molecule consisting of the nucleotide sequence set forth in SEQ ID NO: 7 in which ribonucleotide residues at positions 24 and 25 are connected via the first linker and the second single-stranded oligoRNA molecule consisting of the nucleotide sequence set forth in SEQ ID NO: 6 in which ribonucleotide residues at positions 10 and 11 are connected via the second linker;

(ii) a combination of the first single-stranded oligoRNA molecule consisting of the nucleotide sequence set forth in SEQ ID NO: 19 in which ribonucleotide residues at positions 24 and 25 are connected via the first linker and the second single-stranded oligoRNA molecule consisting of the nucleotide sequence set forth in SEQ ID NO: 18 in which ribonucleotide residues at positions 16 and 17 are connected via the second linker;

(iii) a combination of the first single-stranded oligoRNA molecule consisting of the nucleotide sequence set forth in SEQ ID NO: 27 in which ribonucleotide residues at positions 24 and 25 are connected via the first linker and the second single-stranded oligoRNA molecule consisting of the nucleotide sequence set forth in SEQ ID NO: 26 in which ribonucleotide residues at positions 20 and 21 are connected via the second linker;

(iv) a combination of the first single-stranded oligoRNA molecule consisting of the nucleotide sequence set forth in SEQ ID NO: 29 in which ribonucleotide residues at positions 24 and 25 are connected via the first linker and the second single-stranded oligoRNA molecule consisting of the nucleotide sequence set forth in SEQ ID NO: 28 in which ribonucleotide residues at positions 21 and 22 are connected via the second linker;

(v) a combination of the first single-stranded oligoRNA molecule consisting of the nucleotide sequence set forth in SEQ ID NO: 31 in which ribonucleotide residues at positions 24 and 25 are connected via the first linker and the second single-stranded oligoRNA molecule consisting of the nucleotide sequence set forth in SEQ ID NO: 30 in which ribonucleotide residues at positions 22 and 23 are connected via the second linker; and (vi) a combination of the first single-stranded oligoRNA molecule consisting of the nucleotide sequence set forth in SEQ ID NO: 33 in which ribonucleotide residues at positions 24 and 25 are connected via the first linker and the second single-stranded oligoRNA molecule consisting of the nucleotide sequence set forth in SEQ ID NO: 32 in which ribonucleotide residues at positions 23 and 24 are connected via the second linker.

Examples of the kit include, but are not limited to, a kit for producing a hairpin single-stranded RNA molecule capable of inhibiting expression of GAPDH gene, the kit comprising a combination of single-stranded oligoRNA molecules represented by any of (vii):

(vii) a combination of a single-stranded oligoRNA molecule consisting of the nucleotide sequence set forth in SEQ ID NO: 37 in which ribonucleotide residues at positions 22 and 23 are connected via the first linker and a single-stranded oligoRNA molecule consisting of the nucleotide sequence set forth in SEQ ID NO: 36 in which ribonucleotide residues at positions 20 and 21 are connected via the second linker.

Examples of the kit include, but are not limited to, a kit for producing a hairpin single-stranded RNA molecule capable of inhibiting expression of LAMA1 gene, the kit comprising a combination of single-stranded oligoRNA molecules represented by any of (viii) to (xi):

(viii) a combination of a single-stranded oligoRNA molecule consisting of the nucleotide sequence set forth in SEQ ID NO: 39 in which ribonucleotide residues at positions 24 and 25 are connected via the first linker and a single-stranded oligoRNA molecule consisting of the nucleotide sequence set forth in SEQ ID NO: 38 in which ribonucleotide residues at positions 16 and 17 are connected via the second linker;

(ix) a combination of a single-stranded oligoRNA molecule consisting of the nucleotide sequence set forth in SEQ ID NO: 41 in which ribonucleotide residues at positions 24 and 25 are connected via the first linker and a single-stranded oligoRNA molecule consisting of the nucleotide sequence set forth in SEQ ID NO: 40 in which ribonucleotide residues at positions 22 and 23 are connected via the second linker;

(x) a combination of a single-stranded oligoRNA molecule consisting of the nucleotide sequence set forth in SEQ ID NO: 43 (in which ribonucleotide residues at positions 24 and 31 are connected via a nucleotide linker) and a single-stranded oligoRNA molecule consisting of the nucleotide sequence set forth in SEQ ID NO: 42 (in which ribonucleotide residues at positions 21 and 26 are connected via a nucleotide linker); and (xi) a combination of a single-stranded oligoRNA molecule consisting of the nucleotide sequence set forth in SEQ ID NO: 45 (in which ribonucleotide residues at positions 24 and 31 are connected via a nucleotide linker) and a single-stranded oligoRNA molecule consisting of the nucleotide sequence set forth in SEQ ID NO: 44 (in which ribonucleotide residues at positions 22 and 27 are connected via a nucleotide linker).

Examples of the kit include, but are not limited to, a kit for producing a hairpin single-stranded RNA molecule capable of inhibiting expression of LMNA gene, the kit comprising a combination of single-stranded oligoRNA molecules represented by any of (xii) to (xiii):

(xii) a combination of a single-stranded oligoRNA molecule consisting of the nucleotide sequence set forth in SEQ ID NO: 47 in which ribonucleotide residues at positions 24 and 25 are connected via the first linker and a single-stranded oligoRNA molecule consisting of the nucleotide sequence set forth in SEQ ID NO: 46 in which ribonucleotide residues at positions 21 and 22 are connected via the second linker; and (xiii) a combination of a single-stranded oligoRNA molecule consisting of the nucleotide sequence set forth in SEQ ID NO: 49 in which ribonucleotide residues at positions 24 and 25 are connected via the first linker and a single-stranded oligoRNA molecule consisting of the nucleotide sequence set forth in SEQ ID NO: 48 in which ribonucleotide residues at positions 23 and 24 are connected via the second linker.

EXAMPLES

Hereinafter, our methods, molecules and kits will be described further specifically by using Examples. In this regard, however, the technical scope of this disclosure is not limited to the Examples.

Reference Example 1: Synthesis of Proline Diamido Amidite

A proline diamido amidite to be used to produce a hairpin single-stranded RNA molecule, comprising a proline derivative linker can be synthesized in accordance with the descriptions in WO 2013/027843. Specific examples of synthesis will be illustrated below, but the synthesis method is not limited to them.

(1) Fmoc-Hydroxyamido-L-Proline

Fmoc-L-proline is used as a starting material. Fmoc stands for a 9-fluorenylmethyl-oxycarbonyl group. Fmoc-L-proline (10.00 g, 29.64 mmol), 4-amino-1-butanol (3.18 g, 35.56 mmol), and 1-hydroxybenzotriazole (10.90 g, 70.72 mmol) are mixed. The resulting mixture is degassed under reduced pressure and argon gas is then charged. To the resulting mixture is added anhydrous acetonitrile (140 mL) at room temperature and is further added an anhydrous acetonitrile solution (70 mL) of dicyclohexyl carbodiimide (7.34 g, 35.56 mmol). The resulting mixture is stirred under an argon atmosphere at room temperature for 15 hours. After completion of reaction, the resulting precipitates are filtered. Regarding a filtrate collected, a solvent is distilled away under reduced pressure. Dichloromethane (200 mL) is added to the resulting residue, which is then washed with saturated sodium bicarbonate water (200 mL). Next, an organic layer is collected, dried over magnesium sulfate, and then filtered. Regarding the resulting filtrate, a solvent is distilled away under reduced pressure. Diethyl ether (200 mL) is added to the resulting residue, which is then powdered. The resulting powder was separated by filtration to produce Fmoc-hydroxyamido-L-proline as a colorless powdered substance.

(2) DMTr-Amido-L-Proline

Fmoc-hydroxyamido-L-proline (7.80 g, 19.09 mmol) and anhydrous pyridine (5 mL) are mixed, azeotroped twice at room temperature, and then dried. To the resulting residue are added 4,4'-dimethoxytrityl chloride (8.20 g, 24.20 mmol), 4-dimethylaminopyridine (DMAP) (23 mg, 0.19 mmol), and anhydrous pyridine (39 mL). This mixture is stirred at room temperature for 1 hour, and methanol (7.8 mL) is then added thereto and the mixture is stirred at room temperature for 30 min. The resulting mixture is diluted with dichloromethane (100 mL) and washed with saturated sodium bicarbonate water (150 mL), followed by separation of an organic layer. This organic layer is dried over sodium sulfate, and is then filtered. Regarding the resulting filtrate, a solvent is distilled away under reduced pressure. Anhydrous dimethylformamide (39 mL) and piperidine (18.7 mL, 189 mmol) are added to the resulting crude residue, and the mixture is stirred at room temperature for 1 hour. After completion of the reaction, a solvent is distilled away from the liquid mixture under reduced pressure at room temperature. The resulting residue is subjected to silica gel column chromatography (trade name: Wakogel C-300; eluent $CH_2Cl_2$:$CH_3OH$=9:1, containing 0.05% pyridine) to produce DMTr-amido-L-proline as a pale yellow oily substance. DMTr stands for a dimethoxytrityl group.

(3) DMTr-Hydroxydiamido-L-Proline

An anhydrous dichloromethane solution (120 mL) containing the resulting DMTr-amido-L-proline (6.01 g, 12.28 mmol), N-(3'-dimethylaminopropyl)-N'-ethylcarbodiimide (EDC) (2.83 g, 14.74 mmol), 1-hydroxybenzotriazole (3.98 g, 29.47 mmol), and triethylamine (4.47 g, 44.21 mmol) is mixed. To this liquid mixture is further added under an argon atmosphere at room temperature 6-hydroxy hexanoic acid (1.95 g, 14.47 mmol). The mixture is then stirred under an argon atmosphere at room temperature for 1 hour. The resulting liquid mixture is diluted with dichloromethane (600 mL) and washed with brine (saturated saline) (800 mL) three times. An organic layer is collected, dried over sodium sulfate, and then filtered. Regarding the resulting filtrate, a solvent is distilled away under reduced pressure. This yields DMTr-hydroxydiamido-L-proline as a pale yellow foamed substance.

(4) DMTr-Diamido-L-Proline Amidite

The resulting DMTr-hydroxydiamido-L-proline (8.55 g, 14.18 mmol) is mixed with anhydrous acetonitrile, azeotroped three times at room temperature, and then dried. Diisopropyl ammonium tetrazolide (2.91 g, 17.02 mmol) is added to the resulting residue, degassed under reduced pressure and then argon gas is charged. To the resulting mixture is added anhydrous acetonitrile (10 mL) and is further added an anhydrous acetonitrile solution (7 mL) of 2-cyanoethoxy-N,N,N',N'-tetraisopropyl phosphordiamidite (5.13 g, 17.02 mmol). This mixture is stirred under an argon atmosphere at room temperature for 2 hours. The resulting mixture is diluted with dichloromethane, washed with saturated sodium bicarbonate water (200 mL) three times, and then washed with brine (200 mL). An organic layer is collected, dried over sodium sulfate, and then filtered. Regarding the resulting filtrate, a solvent is distilled away under reduced pressure. The resulting residue is subjected to column chromatography using amino silica gel as a filler (eluent hexane:ethyl acetate=1:3, containing 0.05% pyridine) to provide DMTr-diamido-L-proline amidite as a colorless syrup-like substance.

Example 1: Synthesis of Single-Stranded OligoRNA Molecule

In the Examples below, a hairpin single-stranded RNA molecule having a human TGF-β1 gene expression-inhibiting sequence and linkers using a proline derivative (hereinafter, also referred to as "ssTbRNA molecule," FIG. 2) was produced by ligating two segmentation fragments, namely single-stranded oligoRNA molecules (strand and strand 2) using an RNA ligase (T4 RNA ligase 2) (ligation method, FIG. 1).

To examine their segmentation position, the pairs of single-stranded oligoRNA molecules (strand 1 and strand 2; Table 1), the segmentation position of which was shifted one by one nucleotide in the ssTbRNA molecules, were produced as described below.

TABLE 1

Strand 1 (3'-OH)

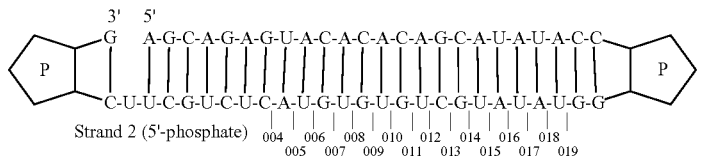

Strand 2 (5'-phosphate)

| Pair name | Strand 1 (sense) | Strand 2 (antisense) |
| --- | --- | --- |
| 004 | 5'-AGCAGAGUACACACAGCAUAUACC-P-GGUAUAUGCUGUGUGUA-3' (SEQ ID NO: 5) | 5'-CUCUGCUUC-P-G-3' (SEQ ID NO: 4) |
| 005 | 5'-AGCAGAGUACACACAGCAUAUACC-P-GGUAUAUGCUGUGUGU-3' (SEQ ID NO: 7) | 5'-ACUCUGCUUC-P-G-3' (SEQ ID NO: 6) |
| 006 | 5'-AGCAGAGUACACACAGCAUAUACC-P-GGUAUAUGCUGUGUG-3' (SEQ ID NO: 9) | 5'-UACUCUGCUUC-P-G-3' (SEQ ID NO: 8) |
| 007 | 5'-AGCAGAGUACACACAGCAUAUACC-P-GGUAUAUGCUGUGU-3' (SEQ ID NO: 11) | 5'-GUACUCUGCUUC-P-G-3' (SEQ ID NO: 10) |
| 008 | 5'-AGCAGAGUACACACAGCAUAUACC-P-GGUAUAUGCUGUG-3' (SEQ ID NO: 13) | 5'-UGUACUCUGCUUC-P-G-3' (SEQ ID NO: 12) |
| 009 | 5'-AGCAGAGUACACACAGCAUAUACC-P-GGUAUAUGCUGU-3' (SEQ ID NO: 15) | 5'-GUGUACUCUGCUUC-P-G-3' (SEQ ID NO: 14) |
| 010 | 5'-AGCAGAGUACACACAGCAUAUACC-P-GGUAUAUGCUG-3' (SEQ ID NO: 17) | 5'-UGUGUACUCUGCUUC-P-G-3' (SEQ ID NO: 16) |
| 011 | 5'-AGCAGAGUACACACAGCAUAUACC-P-GGUAUAUGCU-3' (SEQ ID NO: 19) | 5'-GUGUGUACUCUGCUUC-P-G-3' (SEQ ID NO: 18) |
| 012 | 5'-AGCAGAGUACACACAGCAUAUACC-P-GGUAUAUGC-3' (SEQ ID NO: 21) | 5'-UGUGUGUACUCUGCUUC-P-G-3' (SEQ ID NO: 20) |
| 013 | 5'-AGCAGAGUACACACAGCAUAUACC-P-GGUAUAUG-3' (SEQ ID NO: 23) | 5'-CUGUGUGUACUCUGCUUC-P-G-3' (SEQ ID NO: 22) |
| 014 | 5'-AGCAGAGUACACACAGCAUAUACC-P-GGUAUAU-3' (SEQ ID NO: 25) | 5'-GCUGUGUGUACUCUGCUUC-P-G-3' (SEQ ID NO: 24) |
| 015 | 5'-AGCAGAGUACACACAGCAUAUACC-P-GGUAUA-3' (SEQ ID NO: 27) | 5'-UGCUGUGUGUACUCUGCUUC-P-G-3' (SEQ ID NO: 26) |
| 016 | 5'-AGCAGAGUACACACAGCAUAUACC-P-GGUAU-3' (SEQ ID NO: 29) | 5'-AUGCUGUGUGUACUCUGCUUC-P-G-3' (SEQ ID NO: 28) |
| 017 | 5'-AGCAGAGUACACACAGCAUAUACC-P-GGUA-3' (SEQ ID NO: 31) | 5'-UAUGCUGUGUGUACUCUGCUUC-P-G-3' (SEQ ID NO: 30) |
| 018 | 5'-AGCAGAGUACACACAGCAUAUACC-P-GGU-3' (SEQ ID NO: 33) | 5'-AUAUGCUGUGUGUACUCUGCUUC-P-G-3' (SEQ ID NO: 32) |
| 019 | 5'-AGCAGAGUACACACAGCAUAUACC-P-GG-3' (SEQ ID NO: 35) | 5'-UAUAUGCUGUGUGUACUCUGCUUC-P-G-3' (SEQ ID NO: 34) |

*P: Proline derivative

Specifically, each single-stranded oligoRNA molecule (strand 1 or strand 2) was synthesized via a phosphoramidite method in the 3' to 5' direction by using a nucleic acid synthesizer (trade name: AKTA oligopilot-100, manufactured by GE Healthcare Life Sciences; or trade name: nS-8 and nS-811, manufactured by GeneDesign, Inc.). For the RNA synthesis based on the phosphoramidite method, 5'-O-DMT-2'-O-TBDMSi-RNA phosphoramidite (ThermoFisher Scientific) or 5'-O-DMT-2'-O-TBDMS-RNA phosphoramidite (Sigma-Aldrich Co., LLC.) was used as an RNA amidite. As a carrier, polystyrene beads (NittoPhase® HL rG(ibu), or rU; KINOVATE) or porous glass (CPG) beads (Universal UnyLinker Support 1000 Å; Chem-genes) was used. As a 5'-phosphorylation reagent, 3-(4,4'-dimethoxytrityloxy)-2,2-(N-methyl-amido)]propyl-[(2-cyanoethyl)-(N,N-diisopropyl)]-phosphoramidite (Solid Chemical Phosphorylation Reagent; LINK) was used.

First, an RNA sequence from the 3' end to a residue immediately before a linker (Xa or Ys in FIG. 1) was synthesized. Then, a DMTr-diamido-L-proline amidite for linker formation was linked to the 5' end, and then at the 5' side thereof, an RNA sequence from a residue immediately after the linker to the 5' end (Xs; or Ya₃, Ya₂, and Ya₁ in FIG. 1) was further synthesized. In this way, single-stranded oligoRNA molecules of strand 1 and strand 2 were produced. The single-stranded oligoRNA molecules have, as $Lx_1$ or $Lx_2$, a linker represented by formula (VI-1). Xa is connected to the linker $Lx_1$ on the position-1 nitrogen atom side and Xs is connected to the linker $Lx_1$ on the position-2 carbon atom side in formula (VI-1). Ys is connected to the linker $Lx_2$ on the position-1 nitrogen atom side and $Ya_3$ is connected to the linker $Lx_2$ on the position-2 carbon atom side in formula (VI-1).

Regarding strand 2 (on the antisense side), the synthesis was terminated in a DMTr-OFF state. The single-stranded oligoRNA molecule was cleaved and the bases and the position 2 were deprotected by a conventional procedure. Regarding strand 1 (on the sense side), the synthesis was terminated in a DMTr-ON state.

Example 2: Examination of Ligation Method (Segmentation Position)

To examine a segmentation position where an ssTbRNA molecule should be segmented into two segmentation fragments, the paired strand 1 and strand 2 (Table 1) were ligated using an RNA ligase (T4 RNA ligase 2), and determined the ligation efficiency.

Specifically, first, strand 1 and strand 2 of the respective pairs were each dissolved in injection water (DW) and mixed in equal molar quantities. This equimolar liquid mixture was heat-denatured by heating at 93° C. for 1 min, and then allowed to stand at 55° C. for 15 min for annealing. Thereafter, the temperature was decreased to 4° C. After the temperature fall, the reaction solution was analyzed by reverse-phase high performance liquid chromatography (RP-HPLC) (at 20° C.) and non-denatured polyacrylamide gel electrophoresis (Native PAGE) to examine the annealing state of strand 1 and strand 2.

Conditions for RP-HPLC used to examine the annealing state were as follows:
Column: ACQUITY UPLC Oligonucleotide BEH C18 Column, 130 Å, 1.7 µm, 2.1 mm×100 mm;
Mobile phase: A) 0.1M triethylammonium acetate (TEAA), B) acetonitrile (MeCN); and
Analysis conditions: B5-30%, 10 min, 20° C., 0.4 ml/min.

The conditions for Native PAGE (non-denatured PAGE) used were as follows:
Non-denatured PAGE: 19% acrylamide, electrophoresis at 150 V for 90 min.

This yielded each double-stranded oligoRNA in which strand 1 and strand 2 were annealed from each other. There were some pairs where most molecules of strand 1 and strand 2 were annealed, and other pairs where strand 1 and strand 2 were annealed at a lower percentage.

The resulting double-stranded oligoRNAs (with strand 1 and strand 2 at the final concentration of 10 µM) were comprised in a buffer (50 mM Tris-HCl, 2 mM $MgCl_2$, 1 mM dithiothreitol (DTT), 400 µM adenosine triphosphate (ATP)) to prepare a reaction solution (pH 7.5). Then, 2 µL of 10 U/µL T4 RNA ligase 2 (New England Biolabs; the same applies to the following) was added at 40 U/nmol oligoRNA to have a volume of reaction solution of 50 µL. This reaction solution was incubated at 37° C. for 30 min.

After the enzymatic reaction, the ligation efficiency in the reaction solution was determined by ultra-high performance liquid chromatography (UHPLC) and denatured polyacrylamide gel electrophoresis (Denatured PAGE).

Post-ligation UHPLC conditions were as follows:
Column: ACQUITY UPLC Oligonucleotide BEH C18 Column, 130 Å, 1.7 µm, 2.1 mm×100 mm;
Mobile phase: A) 100 mM hexafluoro-2-propanol (HFIP)-8 mM triethylamine (TEA), B) methanol (MeOH); and
Analysis conditions: B5-40%, 10 min, 80° C., 0.4 ml/min.

The conditions for Denatured PAGE (denatured PAGE) were as follows:
Denatured PAGE: 19% acrylamide, 7.5 M urea, 200 V, 90 min electrophoresis, followed by staining with ethidium bromide (EtBr).

The ligation efficiency (FLP (%)) was calculated, based on the UHPLC analysis result, by an area percentage method using the equation below:

FLP (Full Length Product)(%)=(Peak area of ligation product of interest)/(Total peak area in a chromatogram)×100.

Figure 3:
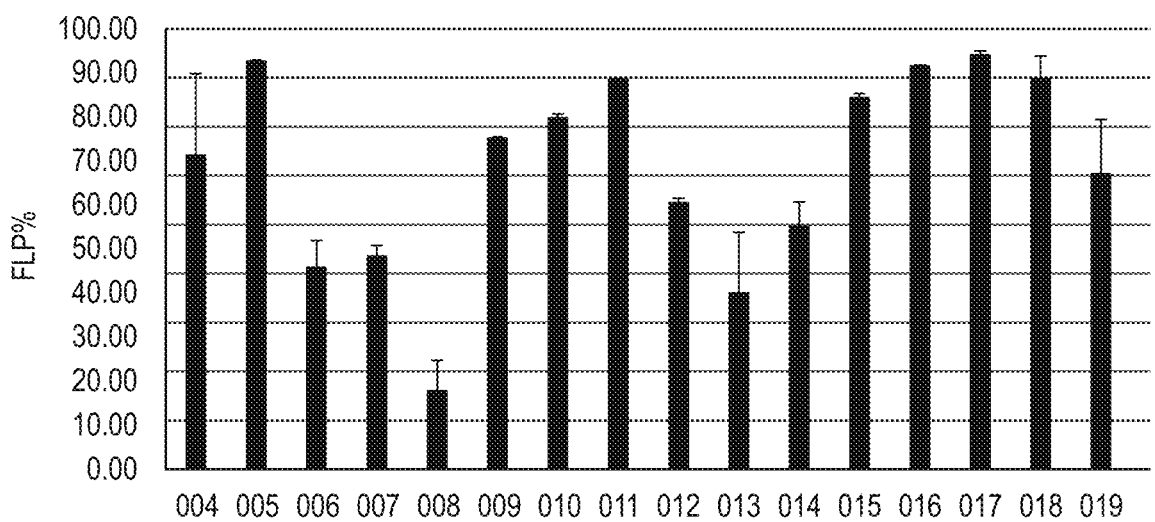
FIG. 3 shows ligation efficiency after annealing and ligation reaction with T4 RNA ligase 2 of a set (pair) of single-stranded oligoRNA molecules (strands 1 and 2) designated as 004 to 019 in Table 1.

FIG. 3 shows the results. Different segmentation positions caused a large difference in the ligation efficiency. At the segmentation positions where the 3' end of strand 1 was U, the ligation efficiency tended to increase. In addition, there was a tendency that in adopting the segmentation position where the 3' end of strand 1 or the 5' end of strand 2 was A, the ligation efficiency was also high. Further, in adopting the segmentation position where a nucleotide at the 3' end of strand 1 or a nucleotide at the 5' end of strand 2 was U or A, respectively, excellent ligation efficiency was exhibited.

Each ligation product was analyzed by LC-MS to confirm a predicted molecular weight. The following equipment was used for the LS-MS analysis:
LC apparatus: UHPLC UltiMate3000 (manufactured by ThermoFisher Scientific, Inc.); and
MS equipment: Q-Exactive (manufactured by ThermoFisher Scientific, Inc.).

Based on the results, the pairs 011, 016, and 018, which were suitable for the ligation method, were selected.

As such, strand 1 and strand 2 of each pair 011, 016, or 018 were annealed from each other, and the reaction solution after they were connected by ligation was analyzed by RP-HPLC under the above conditions. There was a tiny amount of nucleic acid impurities in the reaction solution, except for the ssTbRNA molecule of interest and free strands 1 and 2. Besides, the amount of deletion variants (with a lack of a portion of the sequence of ssTbRNA molecule) appearing at or near the peak of ssTbRNA molecule was also small (Table 2). By contrast, in a solid-phase procedure for synthesizing the entire ssTbRNA molecule by a phosphoramidite method (WO '843), a relatively large amount of short-strand nucleic acid impurities (such as RNA molecules generated by early termination of synthesis at the stage of short strands) other than the ssTbRNA molecule was comprised in the post-synthesis reaction solution, with many deletion variants located at or near the peak of ssTbRNA molecule (Table 2). It has thus been demonstrated that our method enables a hairpin single-stranded RNA molecule of interest to be produced in high purity.

In Table 2, the values for strand 1, strand 2, and the ssTbRNA molecule each indicate a peak area rate based on a chromatogram. In addition, as a relative amount of nucleic acid at or near the peak of ssTbRNA molecule (mainly containing the ssTbRNA molecule and its deletion variants), the total of the peak area rates (%) within the RRT (relative retention time; the relative retention time when the retention time of the peak of ssTbRNA molecule was set to 1)=0.98 to 1.07 was calculated. The peak retention times of strand 1 or strand 2 were sufficiently apart from that of the ssTbRNA molecule and were not present in the range of RRT=0.98 to 1.07.

TABLE 2

| Reaction solution | Strand 1 | Strand 2 | ssTb | Nucleic acid at or near ssTb peak (including deletion variants) |
|---|---|---|---|---|
| 011 | 1.7% | 1.2% | 94.7% | 95.4% |
| 016 | 0.4% | 0.3% | 97.0% | 97.7% |
| 018 | 0.7% | 0.6% | 95.6% | 96.9% |
| Solid synthesis of full-length products | — | — | 85.7% | 91.2% |

Example 3: Examination of Ligation Method (Annealing Temperature)

Single-stranded oligoRNA molecules, which were strand 1 and strand 2 of each pair 011, 016, or 018, were used to conduct an annealing test under two different conditions.

First, under heat denaturation conditions, strand 1 and strand 2 of the respective pairs were each dissolved in injection water and mixed in equal molar quantities of 40 µM. The liquid mixture was heat-denatured by heating at 93° C. for 1 min, and then allowed to stand at 55° C. for 15 min for annealing. Thereafter, the temperature was decreased to 4° C. After the temperature fall, the reaction solution was analyzed by reverse-phase high performance liquid chromatography (RP-HPLC) (at 20° C.) and non-denatured polyacrylamide gel electrophoresis (Native PAGE) to examine the annealing state of strand 1 and strand 2.

Meanwhile, under room temperature conditions, strand 1 and strand 2 of the respective pairs were each dissolved in injection water and mixed in equal molar quantities of from 200 to 400 µM. The resulting liquid mixture was allowed to stand at room temperature for 10 min. The reaction solution after allowed to stand was analyzed by RP-HPLC (at 20° C.) and non-denatured polyacrylamide gel electrophoresis to examine the annealing state of strand 1 and strand 2.

As a result, no single-strand peak was shown by RP-HPLC under any of the heat denaturation conditions or the room temperature conditions, while a peak of a double-strand generated by the annealing was observed. In addition, in the non-denatured polyacrylamide gel electrophoresis, most molecules of strands 1 and 2 were demonstrated to be annealed from each other under both the heat denaturation conditions and the room temperature conditions.

Because the comparable results were obtained under the heat denaturation conditions and the room temperature conditions, the annealing in the ligation method was performed under the room temperature conditions hereinafter.

In the following Examples, the annealing state between single-stranded oligoRNA molecules of strand 1 and strand 2 was verified by RP-HPLC and non-denatured polyacrylamide gel electrophoresis (Native PAGE). After the purity (FLP) of the double-stranded RNA was verified to be 95% or higher by RP-HPLC, the double-stranded RNA was used for the ligation reaction.

Conditions for RP-HPLC used to verify the annealing state were as follows:
Column: ACQUITY UPLC Oligonucleotide BEH C18 Column, 130 Å, 1.7 µm, 2.1 mm×100 mm;
Mobile phase: A) 0.1M triethylammonium acetate (TEAA), B) acetonitrile (MeCN); and
Analysis conditions: B5-30%, 10 min, 20° C., 0.4 ml/min.
The conditions for Native PAGE (non-denatured PAGE) used were as follows:
Non-denatured PAGE: 19% acrylamide, electrophoresis at 150 V for 90 min.

Example 4: Examination of Ligation Method (Reaction Temperature and Reaction Time)

Figure 4:
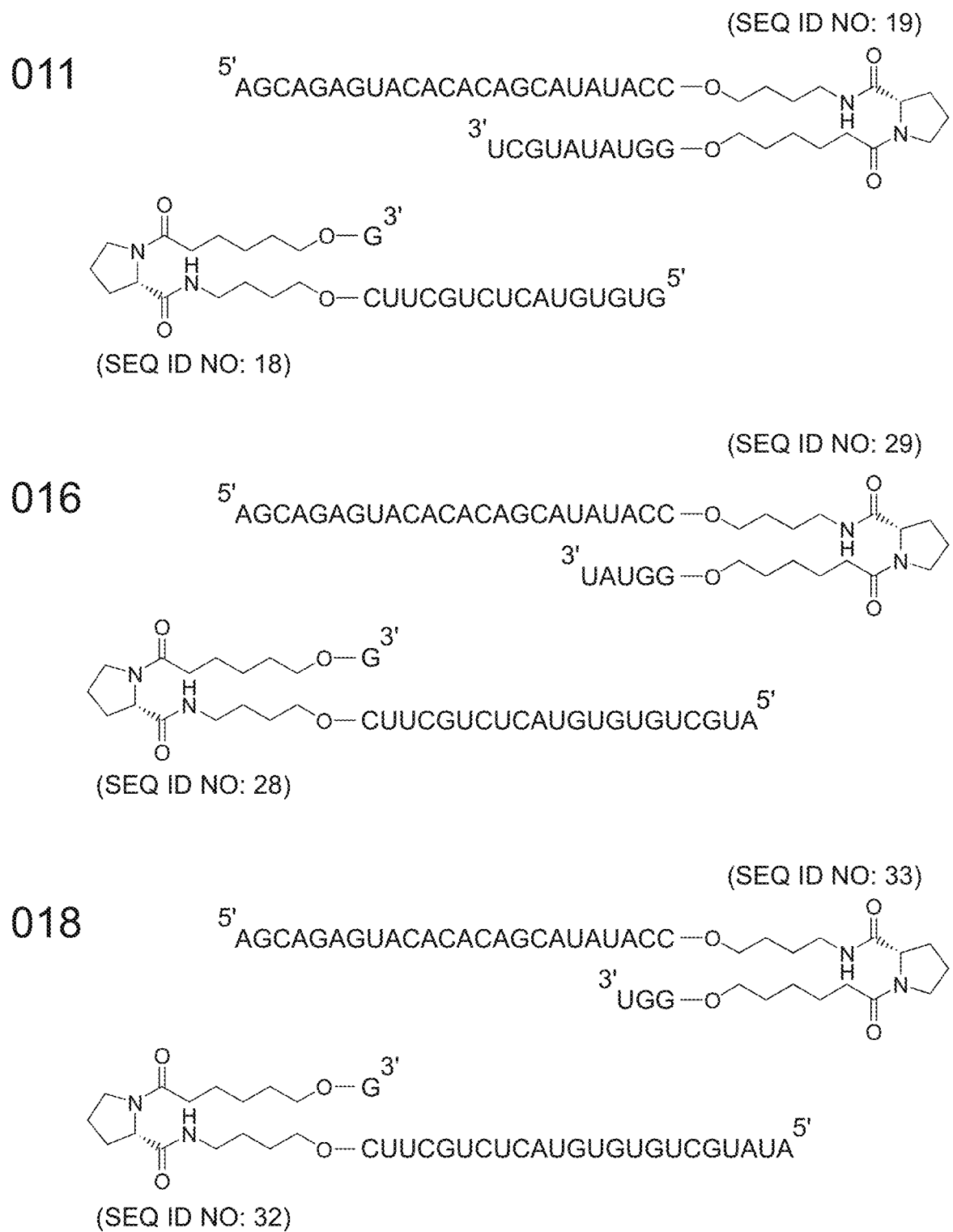
FIG. 4 shows the structures of single-stranded oligoRNA molecules (strands 1 and 2) designated as 011, 016, and 018. The strand 1 is shown on the right side and the strand 2 is shown on the left side in each pair.

Three pairs 011, 016, and 018 (Table 1; hereinafter, the pairs are simply also referred to as 011, 016, or 018, respectively) were each used to examine the temperature and the time of the ligation reaction. FIG. 4 shows the structures of strand 1 and strand 2 of 011, 016, or 018.

Like Example 2, strand 1 and strand 2 of the respective pairs were each dissolved in injection water and mixed in equal molar quantities. This equimolar liquid mixture was allowed to stand at room temperature for 10 min, and double-stranded oligoRNA was prepared by annealing.

Then, 100 µL of a reaction solution containing the resulting double-stranded oligoRNA (equimolar liquid mixture of strands 1 and 2; with each strand at the final concentration of 10 µM, 40 µM, or 100 µM) and 0.4 U/µL T4 RNA ligase 2 (New England Biolabs) in a buffer (50 mM Tris-HCl, 2 mM MgCl$_2$, 1 mM DTT, 400 µM ATP, at pH 7.5 (25° C.)) supplied with T4 RNA ligase 2 was incubated and ligated at 25° C. or 37° C. The amount of enzyme (T4 RNA ligase 2) used in this ligation reaction was 40 U/nmol oligoRNA, 10 U/nmol oligoRNA, or 4 U/nmol oligoRNA. During the ligation reaction, 20 to 25 µL of a sample was taken after 0.5 hours, 2 hours, 4 hours, or 24 hours, and then heated at 85° C. for 20 min for inactivation of the enzyme. The heat-inactivated reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

The results showed that in using each oligoRNA at a concentration of 10 µM or 40 µM, the ligation efficiency was not significantly varied depending on the reaction temperature and the reaction time and was very high in either instance. When the oligoRNA was used at a concentration of 100 µM, a ligation efficiency was decreased compared with using 10 µM or 40 µM. As the reaction time became longer, the ligation efficiency was increased when the oligoRNA was used at a concentration of 100 µM. In addition, the ligation efficiency after 4 hours when the oligoRNA at a concentration of 100 µM was incubated at 25° C. was higher than the example of being incubated at 37° C.

Figure 5:
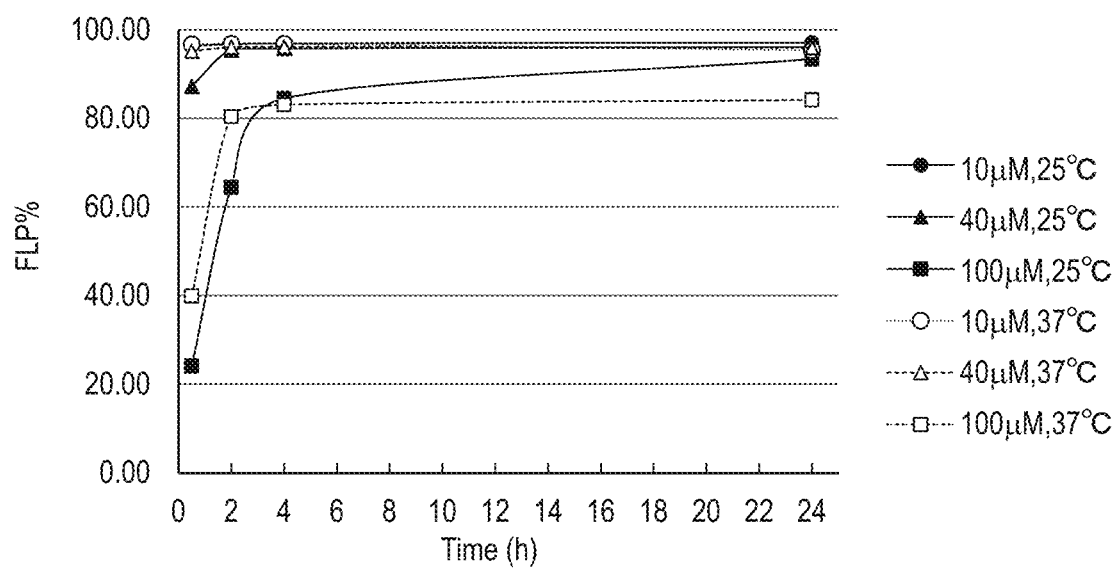
FIG. 5 shows a time-course change in ligation efficiency when oligo-nucleic acids designated as 016 were ligated at different oligoRNA concentrations and different reaction temperatures.
Figure 6:
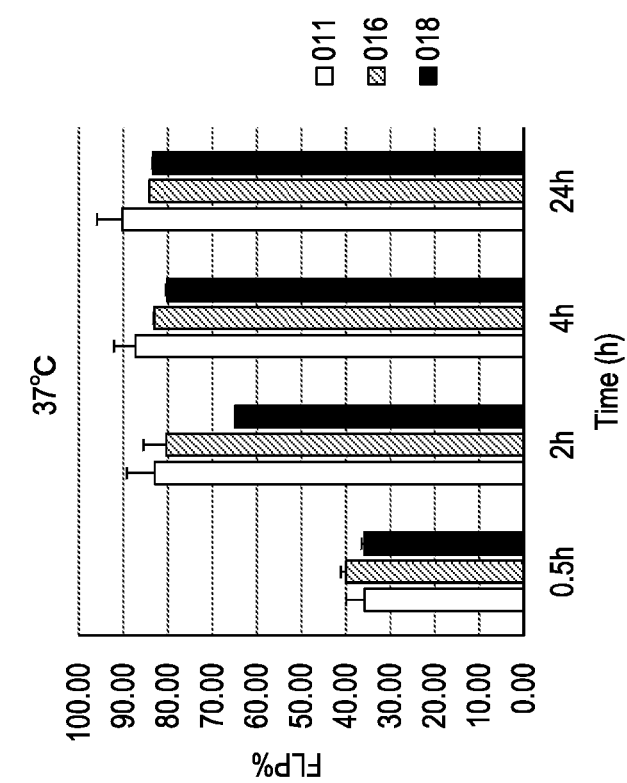
FIG. 6 shows a time-course change in ligation efficiency when oligoRNAs (100 μM) designated as 011, 016, and 018 were ligated at different reaction temperatures. A and B show the results of ligation at 25° C. and 37° C., respectively.
Figure 6:
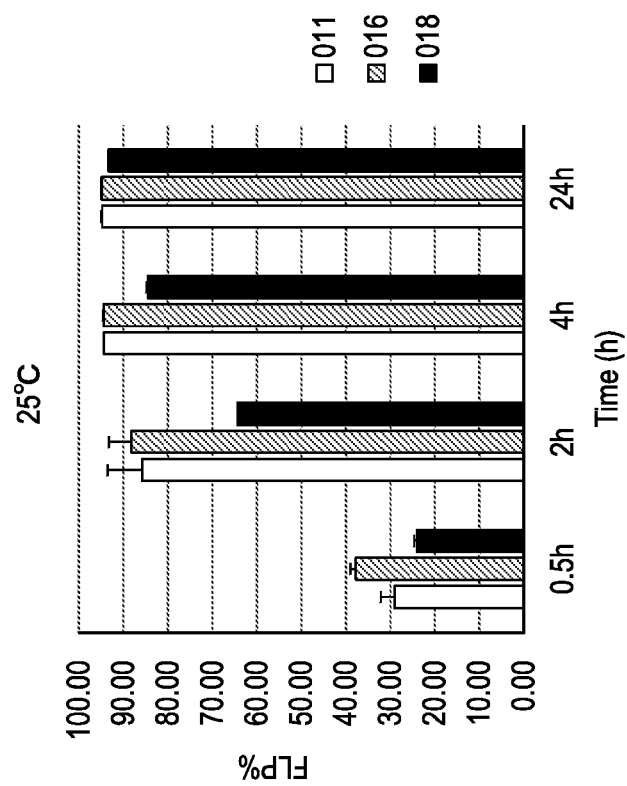

FIG. 5 shows the results of 016. In addition, FIG. 6 shows the results of the ligation reaction at a concentration of 100 µM oligoRNA (A: 25° C., B: 37° C.). The ligation efficiency of 011 or 016 was particularly high.

Example 5: Examination of Ligation Method (ATP Concentration)

The double-stranded oligoRNA of 011 (equimolar liquid mixture) prepared as described in Example 4 was used to examine ATP concentration of the ligation reaction solution. ATP was added to the buffer (50 mM Tris-HCl, 2 mM MgCl$_2$, 1 mM DTT, 400 µM ATP, pH 7.5 (at 25° C.)) supplied with T4 RNA ligase 2 (New England Biolabs) to have an ATP concentration of 0.4 mM (no addition), 1 mM, 2 mM, 5 mM, or 10 mM. Then, 25 µL of a reaction solution containing the double-stranded oligoRNA (with each strand at the final concentration of 10 µM, 20 µM, or 40 µM) and T4 RNA ligase 2 in the buffer prepared above was incubated and ligated at 37° C. for 30 min. After the ligation reaction, the enzyme was inactivated by heating at 85° C. for 20 min. The resulting reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

Figure 7:
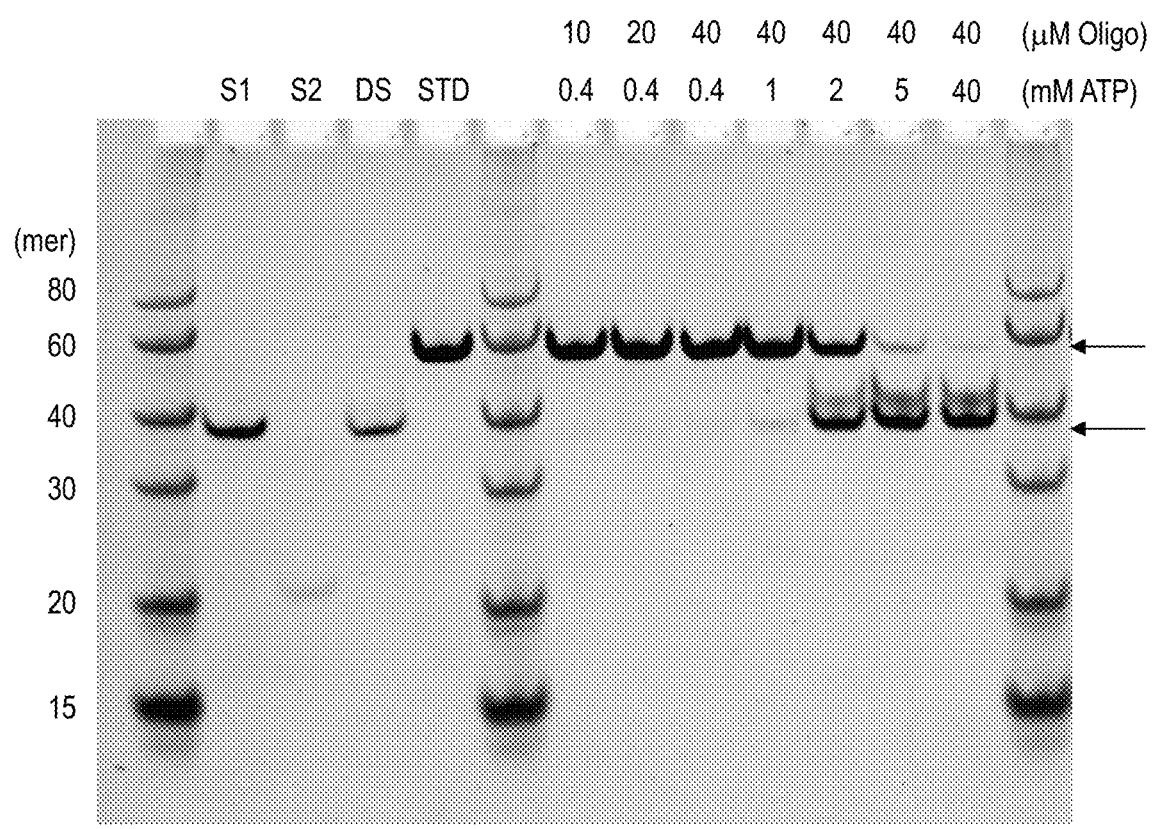
FIG. 7 shows the results of denaturing PAGE analysis when oligoRNAs of 011 were ligated under the conditions of different ATP concentrations.
Figure 8:
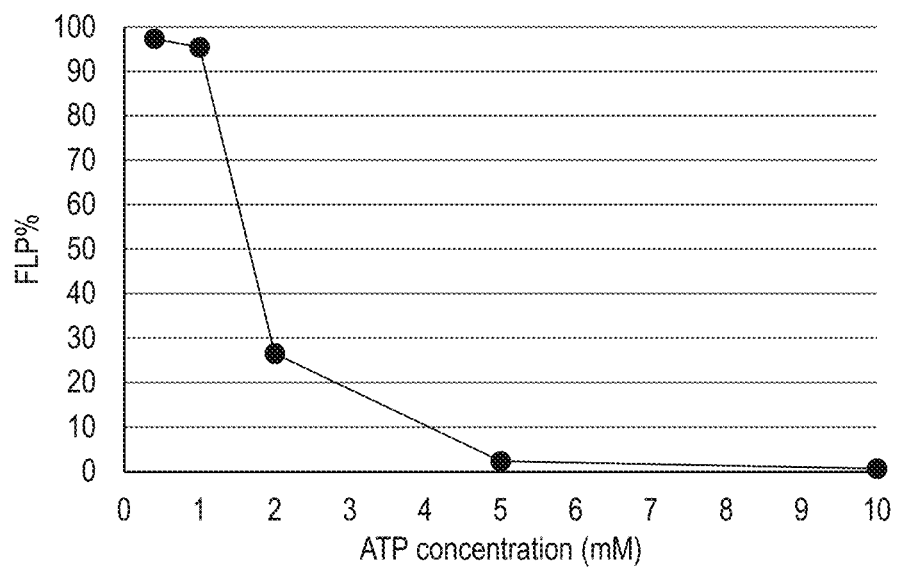
FIG. 8 shows ligation efficiency when oligoRNAs of 011 were ligated under the conditions of different ATP concentrations.

FIG. 7 shows the results of the denatured PAGE and FIG. 8 shows the FLP (%) provided at a concentration of 40 µM oligoRNA. As the ATP concentration increased, the ligation reaction was inhibited more.

Example 6: Examination of Ligation Method (pH)

The double-stranded oligoRNA of 016 (equimolar liquid mixture) prepared as described in Example 4 was used to examine a pH condition in the ligation reaction solution. The following three buffers were used:
(1) 50 mM Tris-HCl (pH 7.0), 2 mM MgCl$_2$, 1 mM dithiothreitol (DTT), 400 µM ATP;
(2) 50 mM Tris-HCl (pH 7.5), 2 mM MgCl$_2$, 1 mM DTT, 400 µM ATP; and
(3) 50 mM Tris acetate (pH 6.5), 2 mM MgCl$_2$, 1 mM DTT, 400 µM ATP.

Then, 30 µL of a reaction solution containing the double-stranded oligoRNA of 016 (with each strand at the final concentration of 10 µM, 100 µM, or 200 µM) and T4 RNA ligase 2 (at the final concentration of 0.4 U/µL) in one of the above buffers was incubated and ligated at 25° C. for 30 minutes, 4 hours, or 24 hours. After the ligation reaction, the enzyme was inactivated by heating at 85° C. for 20 min. The resulting reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

Figure 9:
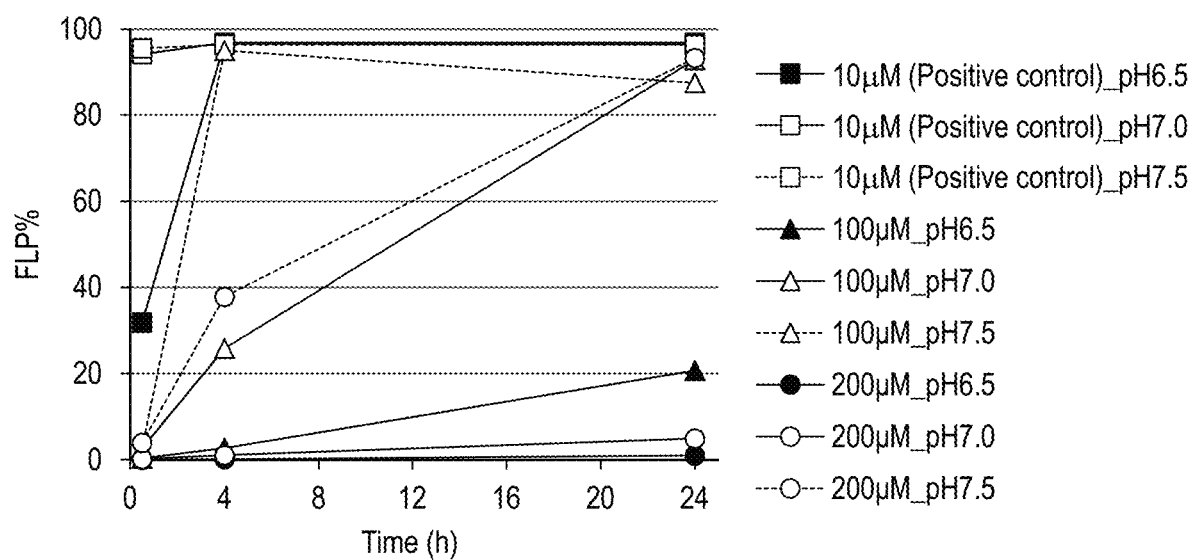
FIG. 9 shows a time course change in ligation efficiency when oligoRNAs of 016 were ligated under the conditions of different oligoRNA concentrations and under different pH conditions.

FIG. 9 shows the results. In the reaction solution at pH 7.5, the ligation efficiency of 95% or higher was exhibited after reaction for 24 hours, even if the reaction solution contains the oligoRNA at a high concentration.

Example 7: Examination of Ligation Method (pH 8.0 or Higher)

The double-stranded oligoRNA of 016 (equimolar liquid mixture) prepared as described in Example 4 was used to further examine a pH condition in the ligation reaction solution. The following four buffers were used:
(1) 50 mM Tris-HCl (pH 7.0), 2 mM $MgCl_2$, 1 mM DTT, 400 µM ATP;
(2) 50 mM Tris-HCl (pH 7.5), 2 mM $MgCl_2$, 1 mM DTT, 400 µM ATP;
(3) 50 mM Tris-HCl (pH 8.0), 2 mM $MgCl_2$, 1 mM DTT, 400 µM ATP; and
(4) 50 mM Tris-HCl (pH 8.5), 2 mM $MgCl_2$, 1 mM DTT, 400 µM ATP.

Figure 10:
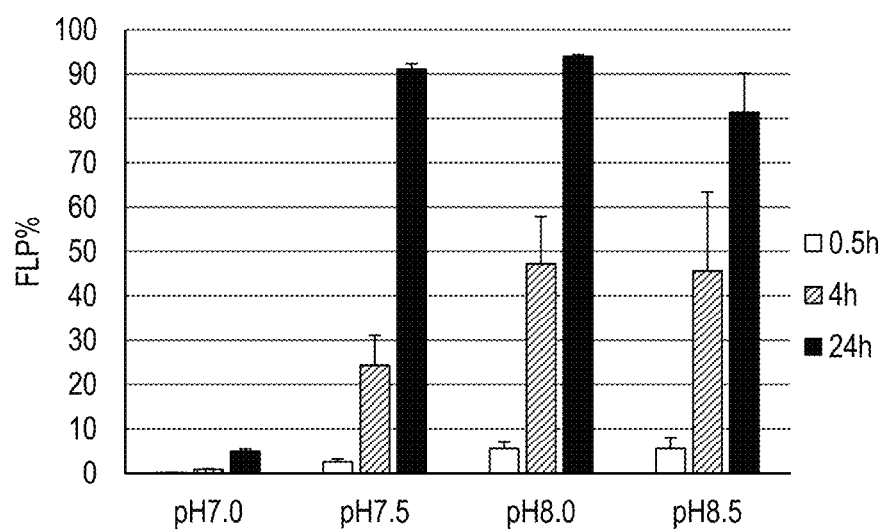
FIG. 10 shows ligation efficiency when oligoRNAs of 016 were ligated under different pH conditions.

Then, 30 µL of a reaction solution containing the double-stranded oligoRNA of 016 (with each strand at the final concentration of 10 µM or 200 µM) and T4 RNA ligase 2 (at the final concentration of 0.4 U/µL) in one of the above buffers was incubated and ligated at 25° C. for 30 minutes, 4 hours, or 24 hours. After the ligation reaction, the enzyme was inactivated by heating at 85° C. for 20 min. The resulting reaction solution was analyzed by denatured PAGE and UHPLC, followed by calculation of the ligation efficiency (FLP (%)). The conditions for the denatured PAGE and UHPLC and how to calculate the FLP (%) were the same as in Example 2. FIG. 10 shows the results. The reaction solutions at pH 7.5 or higher had a high ligation efficiency.

Example 8: Examination of Ligation Method (Divalent Ion Concentration)

The double-stranded oligoRNA of 016 (equimolar liquid mixture) prepared as described in Example 4 was used to examine $MgCl_2$ concentration in the ligation reaction solution. The following five buffers were used:
(1) 0.5 mM $MgCl_2$, 50 mM Tris-HCl (pH 7.5), 1 mM DTT, 400 µM ATP;
(2) 1 mM $MgCl_2$, 50 mM Tris-HCl (pH 7.5), 1 mM DTT, 400 µM ATP;
(3) 2 mM $MgCl_2$, 50 mM Tris-HCl (pH 7.5), 1 mM DTT, 400 µM ATP;
(4) 5 mM $MgCl_2$, 50 mM Tris-HCl (pH 7.5), 1 mM DTT, 400 µM ATP; and
(5) 10 mM $MgCl_2$, 50 mM Tris-HCl (pH 7.5), 1 mM DTT, 400 µM ATP.

Then, 30 µL of a reaction solution containing the double-stranded oligoRNA of 016 (with each strand at the final concentration of 10 µM, 100 µM, or 200 µM) and T4 RNA ligase 2 (at the final concentration of 0.4 U/µL) in one of the above buffers was incubated and ligated at 25° C. for 30 minutes, 4 hours, or 24 hours. After the ligation reaction, the enzyme was inactivated by heating at 85° C. for 20 min. The resulting reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

Figure 11:
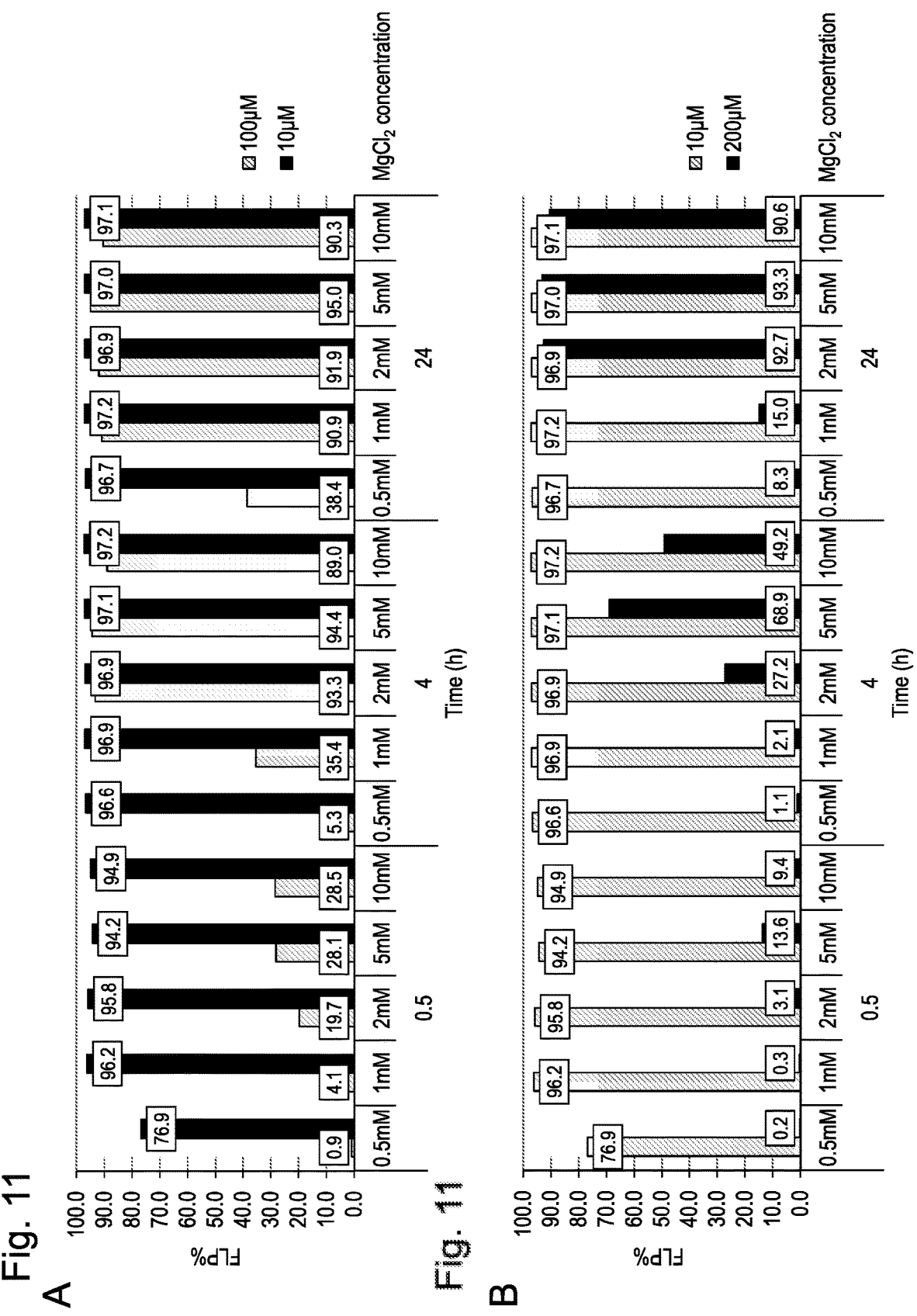
FIG. 11 shows ligation efficiency when oligoRNAs of 016 were ligated under the conditions of different oligoRNA concentrations and of different $MgCl_2$ concentrations. A and B show the results of ligation in the presence of oligoRNAs at 10 μM or 100 μM and oligoRNAs at 10 μM or 200 μM, respectively.

FIG. 11 shows the results (A: 10 µM or 100 µM oligoRNA; B: 10 µM or 200 µM oligoRNA). When the double-stranded oligoRNA was used at a concentration of 100 µM, the reaction at a $MgCl_2$ concentration of 2 mM or higher for 4 hours or longer exhibited a ligation efficiency of 95% or higher. When the oligoRNA concentration was 200 µM, the reaction at a $MgCl_2$ concentration of 2 mM or higher for 24 hours or longer exhibited a ligation efficiency of 95% or higher and at a $MgCl_2$ concentration of 5 mM, the ligation efficiency after 4 hours was shown to very rapidly increase. These results indicated that in using an oligoRNA at a higher concentration, an appropriate increase in the $MgCl_2$ concentration can make the ligation reaction to proceed rapidly.

Example 9: Examination of Enzymatic Ligation Method (Divalent Ion Concentration and pH)

The double-stranded oligoRNA of 016 (equimolar liquid mixture) prepared as described in Example 4 was used to examine a divalent ion concentration in the ligation reaction solution. The following six buffers were used:
(1) 50 mM Tris-HCl (pH 7.5), 1 mM DTT, 400 µM ATP, 2 mM, 5 mM, or 10 mM $MgCl_2$; and
(2) 50 mM Tris-HCl (pH 8.0), 1 mM DTT, 400 µM ATP, 2 mM, 5 mM, or 10 mM $MgCl_2$.

Then, 30 µL of a reaction solution containing the double-stranded oligoRNA of 016 (with each strand at the final concentration of 10 µM or 200 µM) and T4 RNA ligase 2 (at the final concentration of 0.4 U/µL) in one of the above buffers was incubated and ligated at 25° C. for 30 minutes, 4 hours, or 24 hours. After the ligation reaction, the enzyme was inactivated by heating at 85° C. for 20 min. The resulting reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

Figure 12:
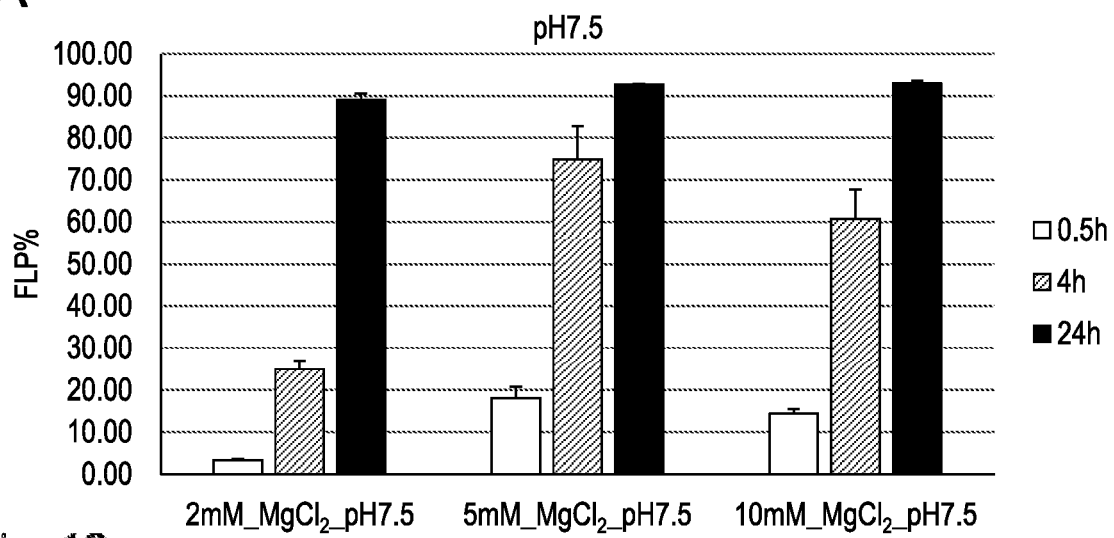
FIG. 12 shows ligation efficiency when oligoRNAs of 016 were ligated under the conditions of different $MgCl_2$ concentrations and under different pH conditions. A and B show the results of ligation at pH 7.5 and pH 8.0, respectively.
Figure 12:
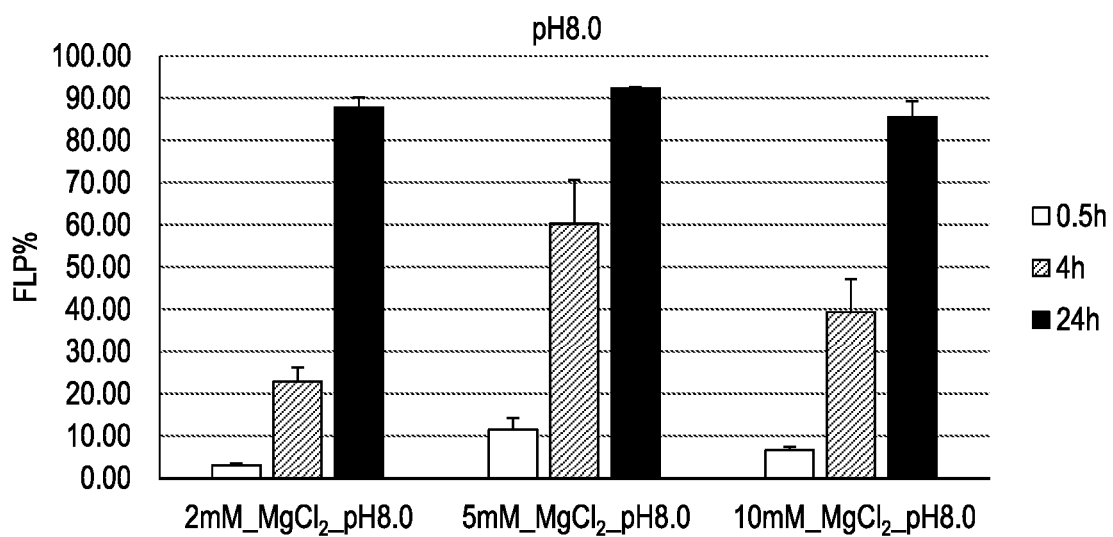

FIG. 12 shows the results (A: pH 7.5, B: pH 8.0). At each of pH 7.5 or pH 8.0, the most rapid increase in the ligation efficiency was found in using 5 mM $MgCl_2$, at the time after 4 hours.

Example 10: Examination of Enzymatic Ligation Method (PEG Addition)

The double-stranded oligoRNA of 018 (equimolar liquid mixture) prepared as described in Example 4 was used to examine how addition of PEG to the ligation reaction solution affected the ligation efficiency.

Then, 30 µL of a reaction solution containing 0.4 U/µL or 0.2 U/µL T4 RNA ligase 2 and the double-stranded oligoRNA (with each strand at the final concentration of 200 µM) in a buffer (5, 10, or 15% (w/v) PEG8000, 50 mM Tris-HCl (pH 8.0), 2 mM $MgCl_2$, 1 mM DTT, 400 µM ATP) was incubated and ligated at 25° C. for 30 minutes, 4 hours, or 24 hours. The amount of enzyme (T4 RNA ligase 2) used in this ligation reaction was 2 U/nmol oligoRNA or 1 U/nmol oligoRNA, which was 1/20 or 1/40, respectively, of the amount of enzyme used in Example 4. After the ligation reaction, the enzyme was inactivated by heating at 85° C. for 20 min. The heat-inactivated reaction solution was analyzed by denatured PAGE and UHPLC, followed by calculation of the ligation efficiency (FLP (%)). The conditions for the denatured PAGE and UHPLC and how to calculate the FLP (%) were the same as in Example 2.

Figure 13:
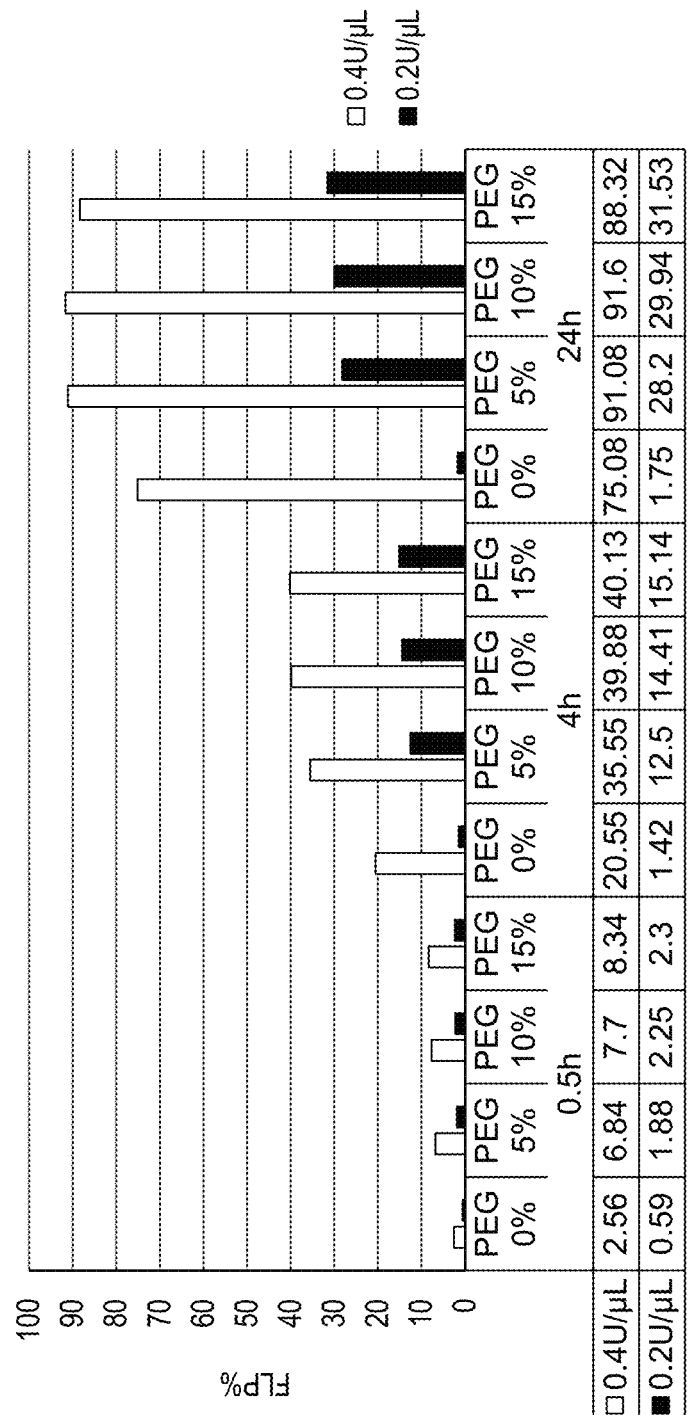
FIG. 13 shows ligation efficiency when ligation was carried out while different amounts of enzyme were used and PEG was added.

FIG. 13 shows the results. It was shown that addition of PEG caused an increase in the ligation efficiency.

Example 11: Analysis of Reaction Time Course in Enzymatic Ligation Method

The double-stranded oligoRNA of 016 (equimolar liquid mixture) prepared as described in Example 4 was used to examine a time course of the ligation reaction.

80 µL of a reaction solution containing the double-stranded oligoRNA (each strand at the final concentration of 100 µM or 200 µM) and 0.4 U/µL T4 RNA ligase 2 in a buffer (50 mM Tris-HCl (pH8.0), 5 mM $MgCl_2$, 1 mM DTT, 400 µM ATP) was incubated and ligated at 25° C. Samples were taken therefrom during the ligation reaction, after 1, 2, 3, 4, 6, 9, 12, 15, 18, and 24 hours from the start. After the enzyme was inactivated by heating at 85° C. for 20 min, UHPLC analysis was conducted, followed by calculation of the FLP %. The conditions for the UHPLC and how to calculate the FLP (%) were the same as in Example 2.

Figure 14:
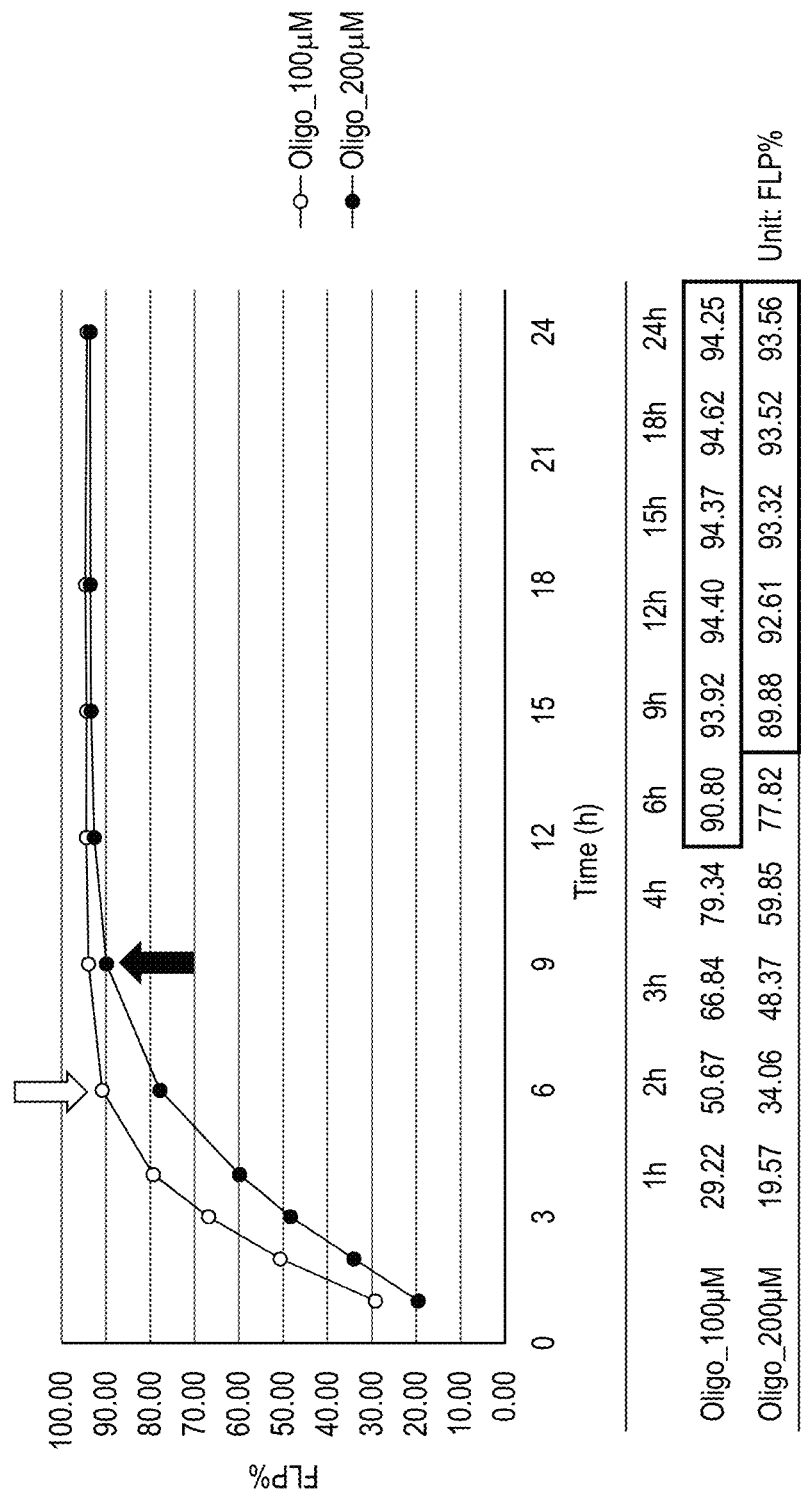
FIG. 14 shows a time course of ligation reaction using different oligoRNA concentrations.

FIG. 14 shows the results. The ligation reaction almost reached a plateau at 6 hours after the start of reaction when the oligoRNA concentration was 100 µM and at 9 hours after the start of reaction 200 µM.

Example 12: Supplemental Addition of OligoRNA in Enzymatic Ligation Method

The double-stranded oligoRNA of 016 (equimolar liquid mixture) prepared as described in Example 4 was used to examine how to increase the yield of an ssTbRNA molecule by sequentially adding single-stranded oligoRNA molecules of strands 1 and 2 to a ligation reaction phase.

First, a ligation reaction solution containing a double-stranded oligoRNA at the final concentration of 100 µM of each strand was used for the examination. 100 µL of a reaction solution containing the double-stranded oligoRNA (at the final concentration of 100 µM; the total amount of oligoRNA in 100 µL of the reaction solution was 10 nmol for each of strand 1 and strand 2) and T4 RNA ligase 2 (0.4 U/µL; 4 U/nmol oligoRNA) in a buffer (50 mM Tris-HCl (pH 8.0), 5 mM $MgCl_2$, 1 mM DTT, 400 µM ATP) was divided into 4 tubes. Then, the ligation reaction was started by incubation at 25° C.

Twelve hours after the start of the ligation reaction, the double-stranded oligoRNA of 016 (equimolar liquid mixture of strands 1 and 2 of 016 in a reaction buffer (50 mM Tris-HCl, 5 mM $MgCl_2$, 1 mM DTT, 400 µM ATP (pH 8.0))) was added to the three tubes at an amount including each strand of 10 nmol (11.1 µL) and the incubation was continued. The oligoRNA concentration in the reaction solution after the addition of oligoRNA was 180 µM (at a concentration of each strand), and the amount of enzyme (T4 RNA ligase 2) was 0.36 U/µL (2 U/nmol oligoRNA).

Twelve hours after the addition of oligoRNA, 2 out of the 3 tubes having received the addition of oligoRNA, were further added with the double-stranded oligoRNA of 016 (the same equimolar liquid mixture as above) at an amount of 10 nmol of each strand (11.1 µL), and the incubation was continued. The oligoRNA concentration in the reaction solution after the second oligoRNA addition was 245 µM (each strand concentration), and the amount of enzyme (T4 RNA ligase 2) was 0.33 U/µL (1.33 U/nmol oligoRNA).

Twelve hours after that, 1 out of the 2 tubes having received the oligoRNA addition twice, was further added with the double-stranded oligoRNA of 016 (the same equimolar liquid mixture as above) at an amount of 10 nmol of each strand (11.1 µL), and the tubes were incubated for another 12 hours. The oligoRNA concentration in the reaction solution after the third oligoRNA addition was 300 µM (each strand concentration), and the amount of enzyme (T4 RNA ligase 2) was 0.3 U/µL (1 U/nmol oligoRNA).

The reaction solution was sampled from each tube every 12 hours, and the enzyme was inactivated by heating samples at 85° C. for 20 min. The resulting post-reaction samples were as follows. The reaction time refers to a time from the start of the ligation reaction.

Tube 1) 100 µM oligoRNA (total 10 nmol for each strand; no addition), the enzyme amount of 0.4 U/µL, the reaction temperature of 25° C., the reaction time of 12, 24, 36, or 48 hours;

Tube 2) 180 µM oligoRNA (total 20 nmol for each strand; added once), the enzyme amount of 0.36 U/µL, the reaction temperature of 25° C., the reaction time of 24, 36, or 48 hours;

Tube 3) 245 µM oligoRNA (total 30 nmol for each strand; added twice), the enzyme amount of 0.33 U/µL, the reaction temperature of 25° C., the reaction time of 36 or 48 hours; or Tube 4) 300 µM oligoRNA (total 40 nmol for each strand; added three times), the enzyme amount of 0.3 U/µL, the reaction temperature of 25° C., the reaction time of 48 hours.

Each sample was analyzed by UHPLC, followed by calculation of the FLP %. The conditions for the UHPLC and how to calculate the FLP (%) were the same as in Example 2. Table 3 shows the results.

TABLE 3

| | FLP (%) | | | |
|---|---|---|---|---|
| | No addition | Added once | Added twice | Added three times |
| After 12 hours | 94.48 | 94.48 | 94.48 | 94.48 |
| After 24 hours | 94.76 | 93.75 | 93.75 | 93.75 |
| After 36 hours | 94.29 | 93.77 | 92.82 | 92.82 |
| After 48 hours | 94.91 | 93.88 | 92.80 | 75.89 |

Figure 15:
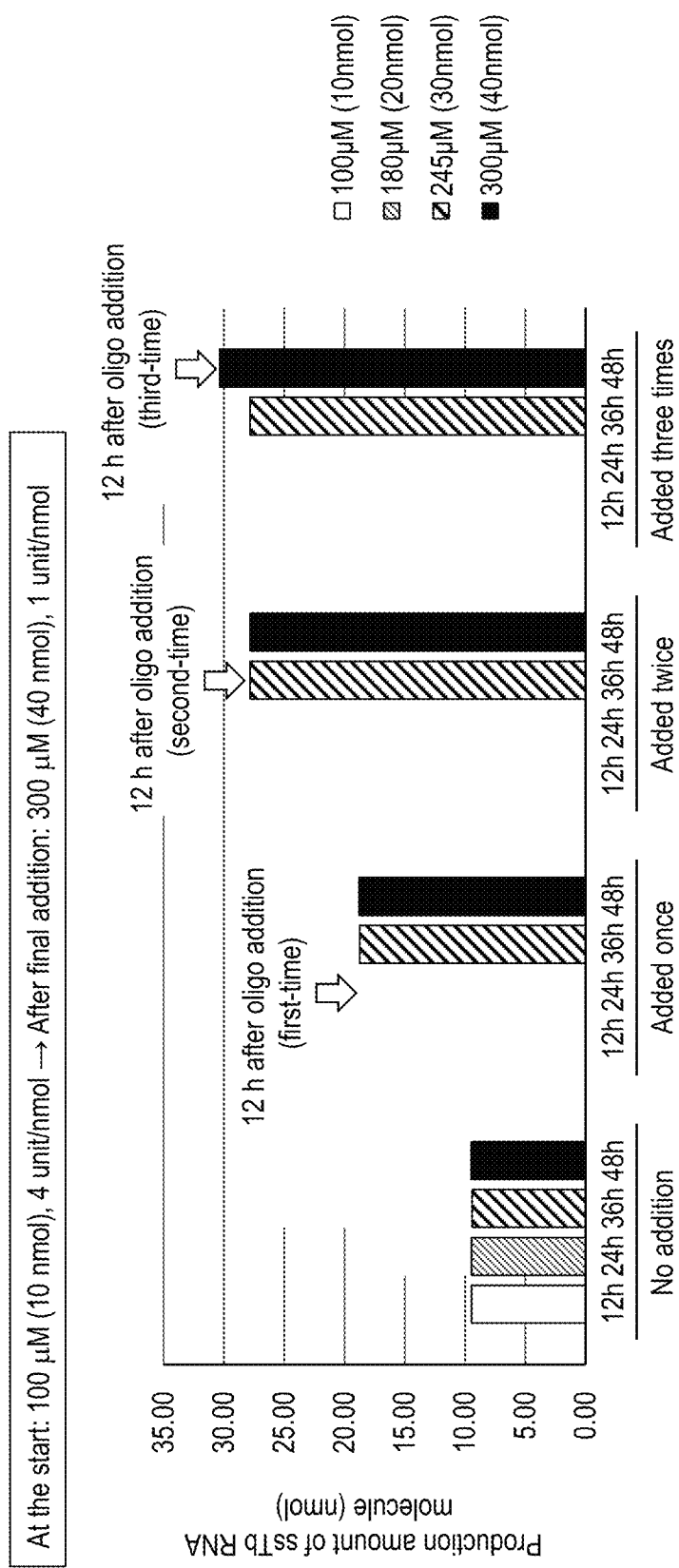
FIG. 15 indicates the amount of ssTbRNA molecule, which is a product of interest, produced during a ligation reaction while the initial oligoRNA concentration was set to 100 μM and oligoRNAs were sequentially added. Amount of ssTbRNA molecule produced (nmol)=(Amount of single-stranded oligoRNA molecule added)×(FLP (Full Length Product)(%))/100. The horizontal axis (h) of the graph represents time after the start of ligation. At the start of ligation, the oligoRNA concentration was 100 µM (10 nmol) and the enzyme concentration was 4 unit/nmol oligoRNA. After the final addition of oligoRNAs, the oligoRNA concentration was 300 µM (40 nmol) and the enzyme concentration was 1 unit/nmol oligoRNA.

Further, for each sample, the production amount (nmol) of the product of interest (ssTbRNA molecule) was estimated from the FLP % and the amount of single-stranded oligoRNA molecules added. FIG. 15 shows the results.

A ligation reaction solution containing a double-stranded oligoRNA at the final concentration of 200 µM of each strand was used for a similar examination.

Next, 100 µL of a reaction solution containing the double-stranded oligoRNA (at the final concentration of 200 µM; the total oligoRNA amount of each of strand 1 or strand 2 in the 100 µL of the reaction solution was 20 nmol) and T4 RNA ligase 2 (0.4 U/µL; 4 U/nmol oligoRNA) in a buffer (50 mM Tris-HCl, 5 mM $MgCl_2$, 1 mM DTT, 400 µM ATP (pH 8.0)) was divided into 4 tubes. Then, the ligation reaction was started by incubation at 25° C. Twelve hours after that, the double-stranded oligoRNA of 016 (equimolar liquid mixture of strands 1 and 2 of 016 in a reaction buffer (50 mM Tris-HCl, 5 mM $MgCl_2$, 1 mM DTT, 400 µM ATP (pH 8.0))) was added to the 3 tubes at an amount of 20 nmol of each strand (22.2 µL) and the incubation was continued. Thereafter, as with using the oligoRNA at the final concentration of 100 μM, the oligoRNA was added every 12 hours three times, and the ligation reaction was continued.

The reaction solution was sampled from each tube every 12 hours, and the enzyme was inactivated by heating at 85° C. for 20 min. The resulting post-reaction samples were as follows. The reaction time refers to a time from the start of the ligation reaction.

Tube 1) 200 μM oligoRNA (total 20 nmol for each strand; no addition), the enzyme amount of 0.4 U/μL, the reaction temperature of 25° C., the reaction time of 12, 24, 36, or 48 hours;

Tube 2) 327 μM oligoRNA (total 40 nmol for each strand; added once), the enzyme amount of 0.36 U/μL, the reaction temperature of 25° C., the reaction time of 24, 36, or 48 hours;

Tube 3) 415 μM oligoRNA (total 60 nmol for each strand; added twice), the enzyme amount of 0.33 U/μL, the reaction temperature of 25° C., the reaction time of 36 or 48 hours; or Tube 4) 480 μM oligoRNA (total 80 nmol for each strand; added three times), the enzyme amount of 0.3 U/μL, the reaction temperature of 25° C., the reaction time of 48 hours.

Each sample was analyzed by UHPLC, followed by calculation of the FLP %. The conditions for the UHPLC and how to calculate the FLP (%) were the same as in Example 2. Table 4 shows the results.

TABLE 4

| | FLP (%) | | | |
|---|---|---|---|---|
| | No addition | Added once | Added twice | Added three times |
| After 12 hours | 92.94 | 92.94 | 92.94 | 92.94 |
| After 24 hours | 93.22 | 91.48 | 91.48 | 91.48 |
| After 36 hours | 93.21 | 92.26 | 74.82 | 74.82 |
| After 48 hours | 93.83 | 92.04 | 74.63 | 56.35 |

Figure 16:
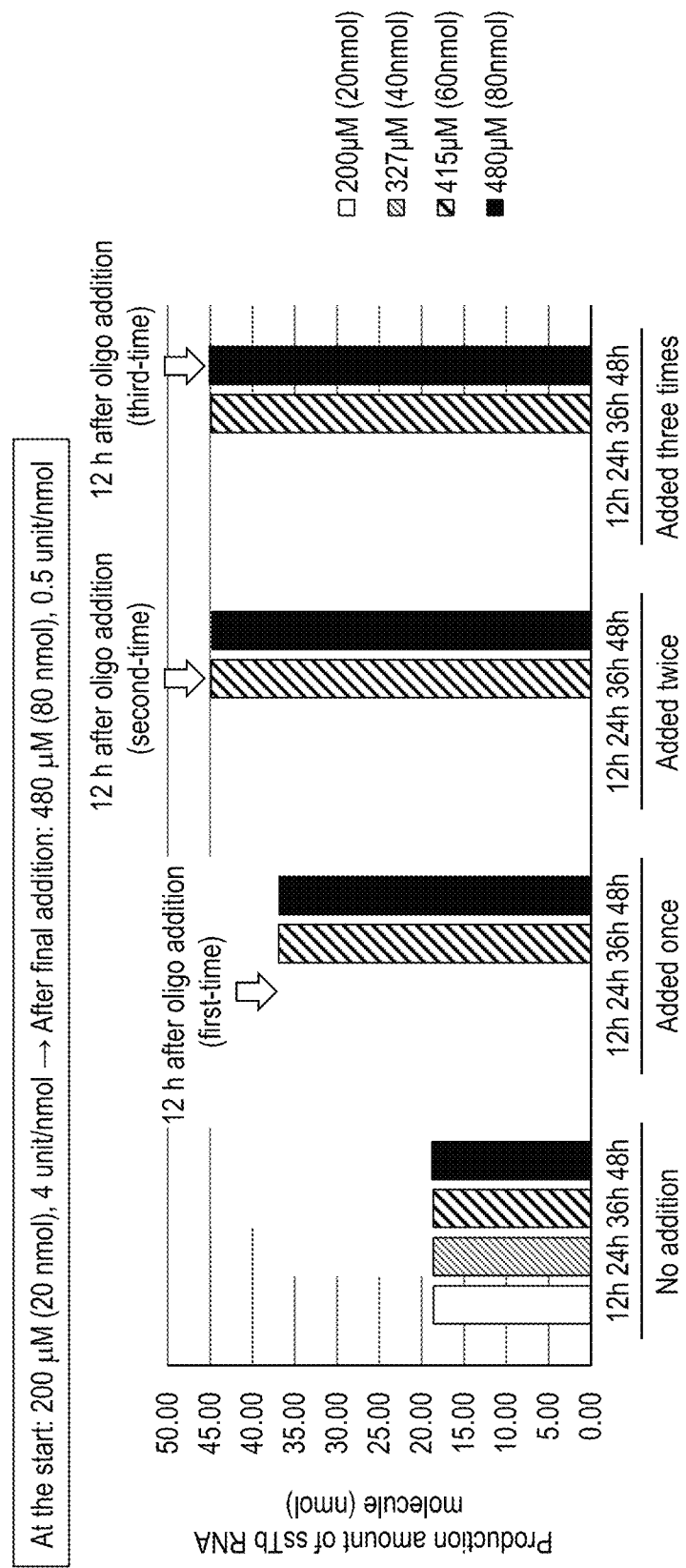
FIG. 16 shows the amount of ssTbRNA molecule, which is a product of interest, produced during a ligation reaction while the initial oligoRNA concentration was set to 200 µM and oligoRNAs were sequentially added. Amount of ssTbRNA molecule produced (nmol)=(Amount of single-stranded oligoRNA molecule added)×(FLP (%))/100. The horizontal axis (h) of the graph represents time after the start of ligation. At the start of ligation, the oligoRNA concentration was 200 µM (20 nmol) and the enzyme concentration was 4 unit/nmol oligoRNA. After the final addition of oligoRNAs, the oligoRNA concentration was 480 µM (80 nmol) and the enzyme concentration was 0.5 unit/nmol oligoRNA.

Further, for each sample, the production amount (nmol) of the product of interest (ssTbRNA molecule) was estimated from the FLP % and the amount of single-stranded oligoRNA molecules added. FIG. 16 shows the results.

The above results have demonstrated that our method can increase the production amount of hairpin single-stranded RNA molecule (herein, an ssTbRNA molecule) by sequentially adding the oligoRNA to a ligation reaction phase.

The typical usage of RNA ligase (the enzyme amount of 0.4 U/μL relative to the amount of a starting oligoRNA of 10 μM) provides a ligation efficiency of more than 90% FLP under substantially the same ligation reaction conditions as above. However, the amount of ssTbRNA molecule produced per 100 μL reaction solution was less than 1 nmol. When compared to such typical examples, it has been shown that our method can reduce the enzyme usage per oligoRNA amount to 1/30 to 1/40, under the efficient reaction conditions which exhibit the FLP of 90% or more.

Example 13: Production of Hairpin Single-Stranded RNA Molecules for Other Target Genes The method in which two segmentation fragments, strands 1 and 2, were ligated as described in Examples 1 and 2 was used to produce hairpin single-stranded RNA molecules containing a gene expression-inhibiting sequence for human GAPDH gene, human LAMA1 gene, or human LMNA gene, instead of human TGF-β1 gene. As a linker, a proline derivative as described in Examples 1 and 2 or a nucleotide linker was used.

FIG. 17 shows the hairpin single-stranded RNA molecules and their segmentation positions in the molecules. The gene expression-inhibiting sequence (antisense sequence) for the gene, which is comprised in each the hairpin single-stranded RNA molecule is boxed in FIG. 17. Table 5 lists pairs of strand 1 and strand 2, which are two segmentation fragments of each hairpin single-stranded RNA molecule. Each pair of strand 1 and strand 2 in Table 5 has U-U, A-A, A-U, or U-A as a combination of terminal nucleotides to be ligated.

TABLE 5

| Pair | Strand 1 (5' to 3') (sense) | Strand 2 (5' to 3') (antisense) |
|---|---|---|
| GAPDH_(1) | CAUGAGAAGUAUGACA ACAGCC-P-GGCUGU (SEQ ID NO: 37) | UGUCAUACUUCUCA UGGUUC-P-GAA (SEQ ID NO: 36) |
| LAMA1_(2) | AGUGUUUGUCUCG UUACAAUAUCC-P-GGAUAUUGUA (SEQ ID NO: 39) | ACGAGACAAACAC UCC-P-G (SEQ ID NO: 38) |
| LAMA1_(3) | AGUGUUUGUCUCGU UACAAUAUCC-P-GGAU (SEQ ID NO: 41) | AUUGUAACGAGAC AAACACUCC-P-G (SEQ ID NO: 40) |
| LAMA1_(4) | AGUGUUUGUCUCGU UACAAUAUCCCACA CCGGAUA (SEQ ID NO: 43) | UUGUAACGAGACA GAACACUCCUUCG (SEQ ID NO: 42) |
| LAMA1_(5) | AGUGUUUGUCUCGU UACAAUAUCCCACA CCGGAU (SEQ ID NO: 45) | AUUGUAACGAGACA AACACUCCUUCGG (SEQ ID NO: 44) |
| LMNA_(6) | AGCGUCACCAAAAA GCGCAAUUCC-P-GGAAU (SEQ ID NO: 47) | UGCGCUUUUUGGUG ACGCUUC-P-G (SEQ ID NO: 46) |
| LMNA_(7) | AGCGUCACCAAAAAGC GCAAUUCC-P-GGA (SEQ ID NO: 49) | AUUGCGCUUUUUGG UGACGCUUC-P-G (SEQ ID NO: 48) |

P: Proline derivative

A method similar to one described in Example 1 was used to synthesize single-stranded oligoRNA molecules of strands 1 and 2 each containing a proline derivative. A solid-phase synthesis using a phosphoramidite method was used to synthesize single-stranded oligoRNA molecules of strands 1 and 2 each containing a nucleotide linker instead of a proline derivative.

Strands 1 and 2 of each pair (Table 5) were annealed from each other to prepare a double-stranded oligoRNA, as described in Example 2. The resulting double-stranded oligoRNA (with strand 1 and strand 2 at the final concentration of 10 μM) were comprised in a buffer (50 mM Tris-HCl, 2 mM MgCl$_2$, 1 mM dithiothreitol (DTT), 400 μM adenosine triphosphate (ATP)) to prepare a reaction solution (pH 7.5, at 25° C.). Then, 2 μL of 10 U/μL T4 RNA ligase 2 (New England Biolabs) (40 U/nmol oligoRNA) was added to have a volume of reaction solution of 50 μL. This reaction solution was incubated at 37° C. for 30 min.

After the enzymatic reaction, the ligation efficiency in the reaction solution was determined with ultra-high performance liquid chromatography (UHPLC) and denatured polyacrylamide gel electrophoresis (Denatured PAGE). The conditions for UHPLC after the ligation and how to calculate the ligation efficiency (FLP (%)) were the same as in Example 2.

Each ligation product was analyzed by LC-MS to confirm having a predicted molecular weight. The LC apparatus and MS equipment used for the LC-MS analysis were the same as those used in Example 2.

Figure 18:
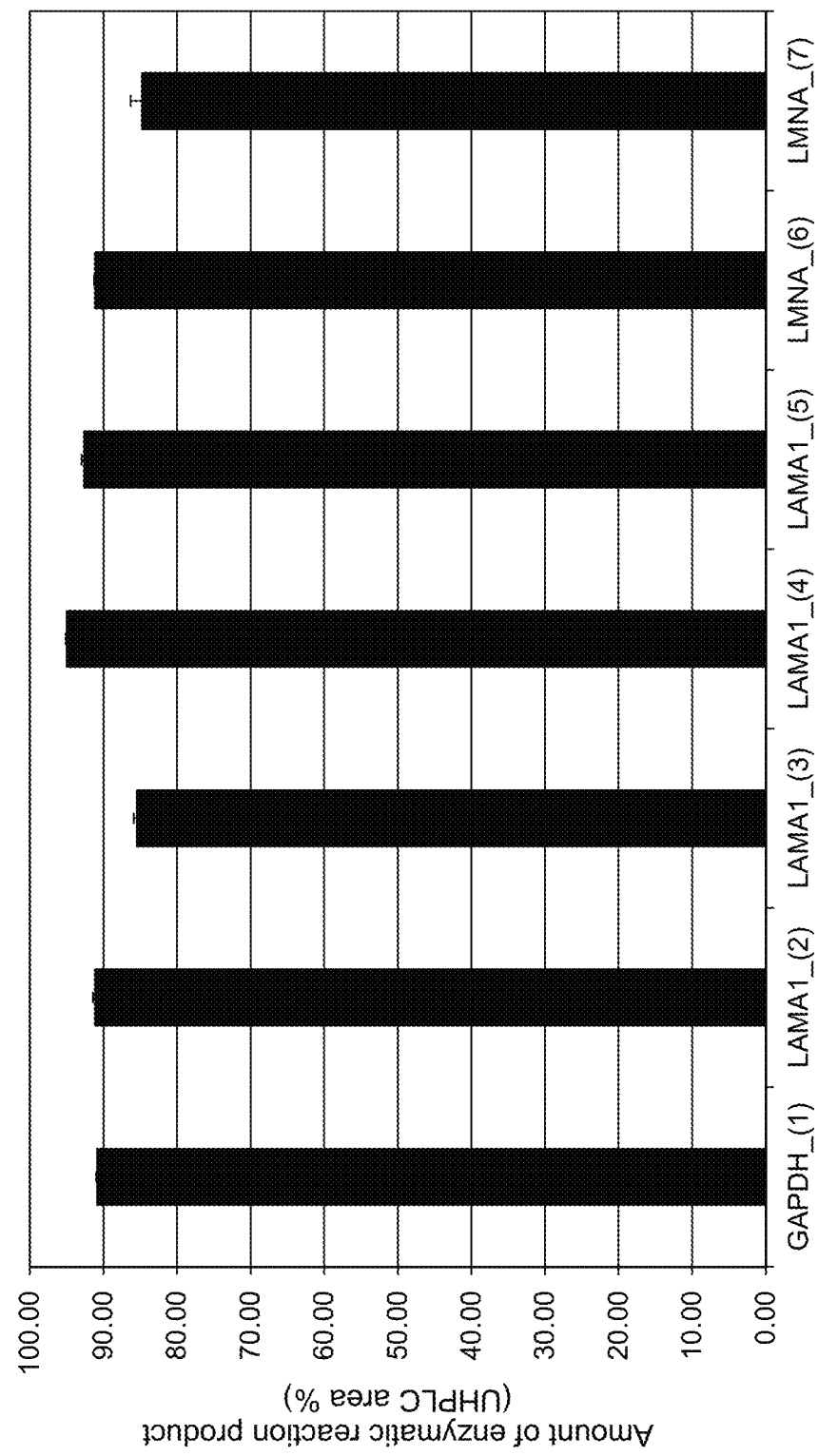
FIG. 18 shows ligation efficiency after annealing and ligation reaction of a pair of single-stranded oligoRNA molecules (strands 1 and 2), which are segmentation fragments of a hairpin single-stranded RNA molecule containing a gene expression-inhibiting sequence for GAPDH gene, LAMA1 gene, or LMNA gene.

FIG. 18 shows the results. Any of the pairs of strands 1 and 2 in Table 5 exhibited a high ligation efficiency.

Comparative Example

In parallel to the experiments in Example 2, double-stranded oligoRNA in which strands 1 and 2 indicated in Table 1 had been annealed from each other was ligated by using T4 RNA ligase, instead of T4 RNA ligase 2, and its ligation efficiency was determined.

Strands 1 and 2 of each of the pairs (Table 1) were annealed to produce a double-stranded oligoRNA, as described in Example 2. The resulting double-stranded oligoRNA (with strand 1 and strand 2 at the final concentration of 10 μM) was comprised in a buffer (50 mM Tris-HCl, 10 mM $MgCl_2$, 5 mM dithiothreitol (DTT), 1 mM adenosine triphosphate (ATP)) to prepare a reaction solution (pH 7.8). 0.5 μL of 10 U/μL T4 RNA ligase (Promega) (10 U/nmol oligoRNA) was added to have a volume of reaction solution of 50 μL. This reaction solution was incubated at 37° C. for 30 min.

After the enzymatic reaction, the ligation efficiency in the reaction solution was determined by ultra-high performance liquid chromatography (UHPLC) and denatured polyacrylamide gel electrophoresis (Denatured PAGE). The conditions for UHPLC after the ligation and how to calculate the ligation efficiency (FLP (%)) were the same as in Example 2.

Figure 19:
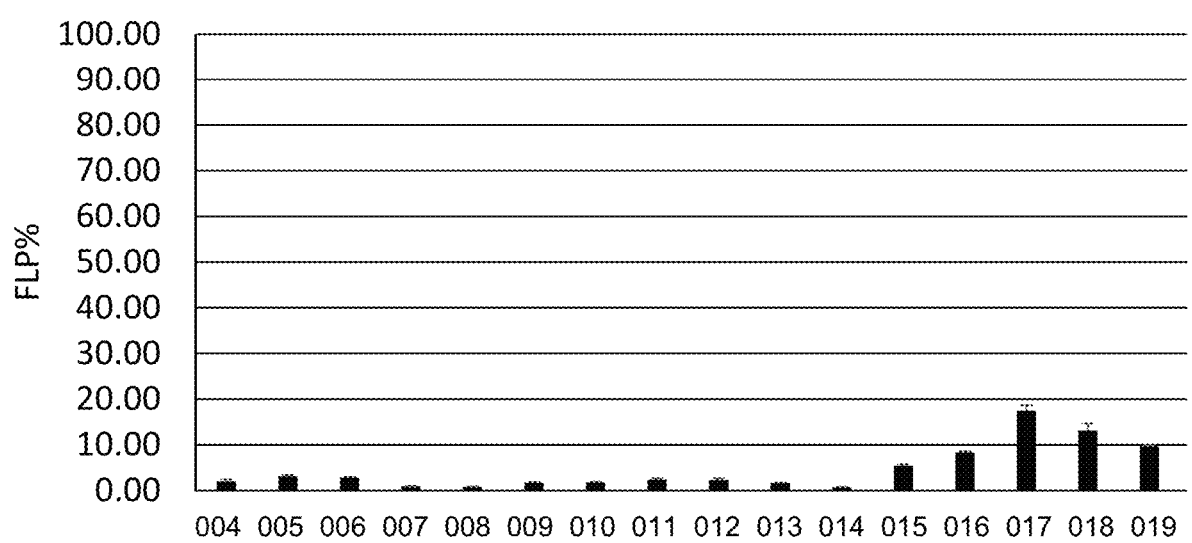
FIG. 19 shows ligation efficiency after annealing and ligation reaction of a set (pair) of strands 1 and 2 listed in Table 1 using T4 RNA ligase.

FIG. 19 shows the results. The ligation efficiency in using T4 RNA ligase was markedly lower than that in using T4 RNA ligase 2 (FIG. 3).

INDUSTRIAL APPLICABILITY

We make it possible to efficiently produce a hairpin single-stranded RNA molecule containing a target gene expression-inhibiting sequence while general-purpose amidites are used and the usage of enzyme is reduced.

SEQUENCE LISTING FREE TEXT

SEQ ID NOs: 1 to 57: synthetic RNA.

All the publications, patents, and patent applications cited herein are incorporated herein by reference in the entirety.

The invention claimed is:

1. A method of producing a hairpin single-stranded RNA molecule capable of inhibiting expression of a target gene, the method comprising:
    an annealing step of annealing a first single-stranded oligoRNA molecule and a second single-stranded oligoRNA molecule; and
    a ligation step of ligating 3' end of the first single-stranded oligoRNA molecule and 5' end of the second single-stranded oligoRNA molecule by an Rnl2 family ligase,
    wherein the first single-stranded oligoRNA molecule comprises a first RNA region and a second RNA region connected via a first linker, and one of the first RNA region and the second RNA region is capable of complementarily binding to the other,
    the second single-stranded oligoRNA molecule comprises a third RNA region and a fourth RNA region connected via a second linker, and one of the third RNA region and the fourth RNA region is capable of complementarily binding to the other,
    the first linker and the second linker are non-nucleotide linkers,
    the first single-stranded oligoRNA molecule and the second single-stranded oligoRNA molecule are capable of forming an intermolecular double strand between complementary sequences at 5'-end or 3'-end thereof,
    when the double strand is formed between the first single-stranded oligoRNA molecule and the second single-stranded oligoRNA molecule during the annealing step, a nick occurs between the 3'-end ribonucleotide residue of the first single-stranded oligoRNA molecule and the 5'-end ribonucleotide residue of the second single-stranded oligoRNA molecule, and a gap of at least one ribonucleotide residue is present between the 5'-end ribonucleotide residue of the first single-stranded oligoRNA molecule and the 3'-end ribonucleotide residue of the second single-stranded oligoRNA molecule, and
    a sequence produced by ligating the first single-stranded oligoRNA molecule and the second single-stranded oligoRNA molecule comprises a gene expression-inhibiting sequence for the target gene.

2. The method according to claim 1, wherein the first single-stranded oligoRNA molecule is represented by formula (I) and the second single-stranded oligoRNA molecule is represented by formula (II):

$$5'\text{-Xs-Lx}_1\text{-Xa-}3' \qquad \text{(I)}$$

$$5'\text{-Ya}_1\text{-Ya}_2\text{-Ya}_3\text{-Lx}_2\text{-Ys-}3' \qquad \text{(II)}$$

wherein Xs, Xa, $Ya_1$, $Ya_2$, $Ya_3$, and Ys each represent one or more ribonucleotide residues,
$Lx_1$ and $Lx_2$ represent the first linker and the second linker, respectively,
$Ya_3$ is complementary to Ys,
Xa-$Ya_1$, which is generated by the ligation step, is complementary to Xs, and
Xa-$Ya_1$-$Ya_2$-$Ya_3$, which is generated by the ligation step, comprises a gene expression-inhibiting sequence for the target gene.

3. The method according to claim 1, wherein the first single-stranded oligoRNA molecule has an uracil (U) or adenine (A) at the 3' end, and the second single-stranded oligoRNA molecule has an uracil (U) or adenine (A) at the 5' end.

4. The method according to claim 1, wherein the first linker and the second linker are each independently a non-nucleotide linker comprising at least one selected from a pyrrolidine backbone and a piperidine backbone.

5. The method according to claim 1, wherein the Rnl2 family ligase is T4 RNA ligase 2.

6. The method according to claim 1, wherein the ligating is carried out in a reaction solution at pH 7.4 to 8.6.

7. The method according to claim 1, wherein the ligating is carried out in a reaction solution comprising 2 to 10 mM divalent metal ion.

8. The method according to claim 1, wherein the first linker and the second linker are each independently a non-nucleotide linker represented by formula (VI):

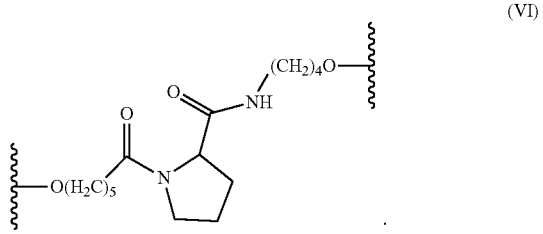

(VI)

9. The method according to claim 1, wherein the target gene is TGF-β1 gene, GAPDH gene, LAMA1 gene, or LMNA gene.

10. The method according to claim 1, wherein the hairpin single-stranded RNA molecule consists of the nucleotide sequence set forth in SEQ ID NO: 1 wherein ribonucleotide residues at positions 24 and 25 are connected via the first linker and ribonucleotide residues at positions 50 and 51 are connected via the second linker.

11. The method according to claim 1, wherein the first single-stranded oligoRNA molecule and the second single-stranded oligoRNA molecule are any of (1) to (21):
   (1) a combination of the first single-stranded oligoRNA molecule consisting of the nucleotide sequence set forth in SEQ ID NO: 7 in which ribonucleotide residues at positions 24 and 25 are connected via the first linker and the second single-stranded oligoRNA molecule consisting of the nucleotide sequence set forth in SEQ ID NO: 6 in which ribonucleotide residues at positions 10 and 11 are connected via the second linker;
   (2) a combination of the first single-stranded oligoRNA molecule consisting of a nucleotide sequence set forth in SEQ ID NO: 19 in which ribonucleotide residues at positions 24 and 25 are connected via the first linker and the second single-stranded oligoRNA molecule consisting of the nucleotide sequence set forth in SEQ ID NO: 18 in which ribonucleotide residues at positions 16 and 17 are connected via the second linker;
   (3) a combination of the first single-stranded oligoRNA molecule consisting of the nucleotide sequence set forth in SEQ ID NO: 27 in which ribonucleotide residues at positions 24 and 25 are connected via the first linker and the second single-stranded oligoRNA molecule consisting of the nucleotide sequence set forth in SEQ ID NO: 26 in which ribonucleotide residues at positions 20 and 21 are connected via the second linker;
   (4) a combination of the first single-stranded oligoRNA molecule consisting of a nucleotide sequence set forth in SEQ ID NO: 29 in which ribonucleotide residues at positions 24 and 25 are connected via the first linker and the second single-stranded oligoRNA molecule consisting of the nucleotide sequence set forth in SEQ ID NO: 28 in which ribonucleotide residues at positions 21 and 22 are connected via the second linker;
   (5) a combination of the first single-stranded oligoRNA molecule consisting of a nucleotide sequence set forth in SEQ ID NO: 31 in which ribonucleotide residues at positions 24 and 25 are connected via the first linker and the second single-stranded oligoRNA molecule consisting of the nucleotide sequence set forth in SEQ ID NO: 30 in which ribonucleotide residues at positions 22 and 23 are connected via the second linker;
   (6) a combination of the first single-stranded oligoRNA molecule consisting of a nucleotide sequence set forth in SEQ ID NO: 33 in which ribonucleotide residues at positions 24 and 25 are connected via the first linker and the second single-stranded oligoRNA molecule consisting of the nucleotide sequence set forth in SEQ ID NO: 32 in which ribonucleotide residues at positions 23 and 24 are connected via the second linker;
   (7) a combination of the first single-stranded oligoRNA molecule consisting of the nucleotide sequence set forth in SEQ ID NO: 5 in which ribonucleotide residues at positions 24 and 25 are connected via the first linker and the second single-stranded oligoRNA molecule consisting of the nucleotide sequence set forth in SEQ ID NO: 4 in which ribonucleotide residues at positions 9 and 10 are connected via the second linker;
   (8) a combination of the first single-stranded oligoRNA molecule consisting of the nucleotide sequence set forth in SEQ ID NO: 9 in which ribonucleotide residues at positions 24 and 25 are connected via the first linker and the second single-stranded oligoRNA molecule consisting of the nucleotide sequence set forth in SEQ ID NO: 8 in which ribonucleotide residues at positions 11 and 12 are connected via the second linker;
   (9) a combination of the first single-stranded oligoRNA molecule consisting of the nucleotide sequence set forth in SEQ ID NO: 11 in which ribonucleotide residues at positions 24 and 25 are connected via the first linker and the second single-stranded oligoRNA molecule consisting of the nucleotide sequence set forth in SEQ ID NO: 10 in which ribonucleotide residues at positions 12 and 13 are connected via the second linker;
   (10) a combination of the first single-stranded oligoRNA molecule consisting of the nucleotide sequence set forth in SEQ ID NO: 13 in which ribonucleotide residues at positions 24 and 25 are connected via the first linker and the second single-stranded oligoRNA molecule consisting of the nucleotide sequence set forth in SEQ ID NO: 12 in which ribonucleotide residues at positions 13 and 14 are connected via the second linker;
   (11) a combination of the first single-stranded oligoRNA molecule consisting of the nucleotide sequence set forth in SEQ ID NO: 15 in which ribonucleotide residues at positions 24 and 25 are connected via the first linker and the second single-stranded oligoRNA molecule consisting of the nucleotide sequence set forth in SEQ ID NO: 14 in which ribonucleotide residues at positions 14 and 15 are connected via the second linker;
   (12) a combination of the first single-stranded oligoRNA molecule consisting of the nucleotide sequence set forth in SEQ ID NO: 17 in which ribonucleotide residues at positions 24 and 25 are connected via the first linker and the second single-stranded oligoRNA molecule consisting of the nucleotide sequence set forth in SEQ ID NO: 16 in which ribonucleotide residues at positions 15 and 16 are connected via the second linker;
   (13) a combination of the first single-stranded oligoRNA molecule consisting of the nucleotide sequence set forth in SEQ ID NO: 21 in which ribonucleotide residues at positions 24 and 25 are connected via the first linker and the second single-stranded oligoRNA molecule consisting of the nucleotide sequence set forth in SEQ ID NO: 20 in which ribonucleotide residues at positions 17 and 18 are connected via the second linker;

(14) a combination of the first single-stranded oligoRNA molecule consisting of the nucleotide sequence set forth in SEQ ID NO: 23 in which ribonucleotide residues at positions 24 and 25 are connected via the first linker and the second single-stranded oligoRNA molecule consisting of the nucleotide sequence set forth in SEQ ID NO: 22 in which ribonucleotide residues at positions 18 and 19 are connected via the second linker;
(15) a combination of the first single-stranded oligoRNA molecule consisting of the nucleotide sequence set forth in SEQ ID NO: 25 in which ribonucleotide residues at positions 24 and 25 are connected via the first linker and the second single-stranded oligoRNA molecule consisting of the nucleotide sequence set forth in SEQ ID NO: 24 in which ribonucleotide residues at positions 19 and 20 are connected via the second linker;
(16) a combination of the first single-stranded oligoRNA molecule consisting of the nucleotide sequence set forth in SEQ ID NO: 35 in which ribonucleotide residues at positions 24 and 25 are connected via the first linker and the second single-stranded oligoRNA molecule consisting of the nucleotide sequence set forth in SEQ ID NO: 34 in which ribonucleotide residues at positions 20 and 21 are connected via the second linker;
(17) a combination of the first single-stranded oligoRNA molecule consisting of a nucleotide sequence set forth in SEQ ID NO: 37 in which ribonucleotide residues at positions 22 and 23 are connected via the first linker and the second single-stranded oligoRNA molecule consisting of the nucleotide sequence set forth in SEQ ID NO: 36 in which ribonucleotide residues at positions 20 and 21 are connected via the second linker;
(18) a combination of the first single-stranded oligoRNA molecule consisting of the nucleotide sequence set forth in SEQ ID NO: 39 in which ribonucleotide residues at positions 24 and 25 are connected via the first linker and the second single-stranded oligoRNA molecule consisting of the nucleotide sequence set forth in SEQ ID NO: 38 in which ribonucleotide residues at positions 16 and 17 are connected via the second linker;
(19) a combination of the first single-stranded oligoRNA molecule consisting of the nucleotide sequence set forth in SEQ ID NO: 41 in which ribonucleotide residues at positions 24 and 25 are connected via the first linker and the second single-stranded oligoRNA molecule consisting of the nucleotide sequence set forth in SEQ ID NO: 40 in which ribonucleotide residues at positions 22 and 23 are connected via the second linker;
(20) a combination of the first single-stranded oligoRNA molecule consisting of the nucleotide sequence set forth in SEQ ID NO: 47 in which ribonucleotide residues at positions 24 and 25 are connected via the first linker and the second single-stranded oligoRNA molecule consisting of the nucleotide sequence set forth in SEQ ID NO: 46 in which ribonucleotide residues at positions 21 and 22 are connected via the second linker; and
(21) a combination of the first single-stranded oligoRNA molecule consisting of the nucleotide sequence set forth in SEQ ID NO: 49 in which ribonucleotide residues at positions 24 and 25 are connected via the first linker and the second single-stranded oligoRNA molecule consisting of the nucleotide sequence set forth in SEQ ID NO: 48 in which ribonucleotide residues at positions 23 and 24 are connected via the second linker.

12. The method according to claim 1, wherein said ligation step comprises, after a first ligation reaction, performing once or repeating more than one time an additional reaction step of further adding the first single-stranded oligoRNA molecule and the second single-stranded oligoRNA molecule to perform further ligation reaction.

13. The method according to claim 1, wherein said Rnl2 family ligase is used in an amount of 10 unit or less per nmol of the first single-stranded oligoRNA molecule and/or second single-stranded oligoRNA molecule.

14. The method according to claim 2, wherein Xa consists of 2 to 20 nucleotides.

* * * * *

SEQUENCE LISTING

```
<160> NUMBER OF SEQ ID NOS: 57

<210> SEQ ID NO 1
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker
<220> FEATURE:
<221> NAME/KEY: modified_base
<222> LOCATION: (50)..(51)
<223> OTHER INFORMATION: nucleotides 50 and 51 are connected via a
      linker

<400> SEQUENCE: 1
agcagaguac acacagcaua uaccgguaua ugcugugugu acucugcuuc g         51

<210> SEQ ID NO 2
<211> LENGTH: 24
<212> TYPE: RNA
<213> ORGANISM: Artificial
<220> FEATURE:
<223> OTHER INFORMATION: synthetic

<400> SEQUENCE: 2
agcagaguac acacagcaua uacc                                        24

<210> SEQ ID NO 3
<211> LENGTH: 26
<212> TYPE: RNA
<213> ORGANISM: Artificial
<220> FEATURE:
<223> OTHER INFORMATION: synthetic

<400> SEQUENCE: 3
```

```
gguauaugcu guguguacuc ugcuuc                                            26

<210> SEQ ID NO 4
<211> LENGTH: 10
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (9)..(10)
<223> OTHER INFORMATION: nucleotides 9 and 10 are connected via a linker

<400> SEQUENCE: 4
cucugcuucg                                                              10

<210> SEQ ID NO 5
<211> LENGTH: 41
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 5
agcagaguac acacagcaua uaccgguaua ugcugugugu a                           41

<210> SEQ ID NO 6
<211> LENGTH: 11
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (10)..(11)
<223> OTHER INFORMATION: nucleotides 10 and 11 are connected via a
      linker

<400> SEQUENCE: 6
acucugcuuc g                                                            11

<210> SEQ ID NO 7
<211> LENGTH: 40
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 7
agcagaguac acacagcaua uaccgguaua ugcugugugu                             40

<210> SEQ ID NO 8
<211> LENGTH: 12
<212> TYPE: RNA
<213> ORGANISM: Artificial
<220> FEATURE:
<223> OTHER INFORMATION: synthetic
<220> FEATURE:
<221> NAME/KEY: modified_base
```

```
<222> LOCATION: (11)..(12)
<223> OTHER INFORMATION: nucleotides 11 and 12 are connected via a
      linker

<400> SEQUENCE: 8
uacucugcuu cg                                                          12

<210> SEQ ID NO 9
<211> LENGTH: 39
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 9
agcagaguac acacagcaua uaccgguaua ugcugugug                             39

<210> SEQ ID NO 10
<211> LENGTH: 13
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (12)..(13)
<223> OTHER INFORMATION: nucleotides 12 and 13 are connected via a
      linker

<400> SEQUENCE: 10
guacucugcu ucg                                                         13

<210> SEQ ID NO 11
<211> LENGTH: 38
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 11
agcagaguac acacagcaua uaccgguaua ugcugugu                              38

<210> SEQ ID NO 12
<211> LENGTH: 14
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (13)..(14)
<223> OTHER INFORMATION: nucleotides 13 and 14 are connected via a
      linker

<400> SEQUENCE: 12
uguacucugc uucg                                                        14

<210> SEQ ID NO 13
<211> LENGTH: 37
```

```
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 13
agcagaguac acacagcaua uaccgguaua ugcugug                                    37

<210> SEQ ID NO 14
<211> LENGTH: 15
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (14)..(15)
<223> OTHER INFORMATION: nucleotides 14 and 15 are connected via a
      linker

<400> SEQUENCE: 14
guguacucug cuucg                                                            15

<210> SEQ ID NO 15
<211> LENGTH: 36
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 15
agcagaguac acacagcaua uaccgguaua ugcugu                                     36

<210> SEQ ID NO 16
<211> LENGTH: 16
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (15)..(16)
<223> OTHER INFORMATION: nucleotides 15 and 16 are connected via a
      linker

<400> SEQUENCE: 16
uguguacucu gcuucg                                                           16

<210> SEQ ID NO 17
<211> LENGTH: 35
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 17
```
agcagaguac acacagcaua uaccgguaua ugcug                35

<210> SEQ ID NO 18
<211> LENGTH: 17
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (16)..(17)
<223> OTHER INFORMATION: nucleotides 16 and 17 are connected via a
      linker

<400> SEQUENCE: 18
guguguacuc ugcuucg                                    17

<210> SEQ ID NO 19
<211> LENGTH: 34
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 19
agcagaguac acacagcaua uaccgguaua ugcu                 34

<210> SEQ ID NO 20
<211> LENGTH: 18
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (17)..(18)
<223> OTHER INFORMATION: nucleotides 17 and 18 are connected via a
      linker

<400> SEQUENCE: 20
uguguguacu cugcuucg                                   18

<210> SEQ ID NO 21
<211> LENGTH: 33
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 21
agcagaguac acacagcaua uaccgguaua ugc                  33

<210> SEQ ID NO 22
<211> LENGTH: 19
<212> TYPE: RNA
<213> ORGANISM: Artificial
<220> FEATURE:
<223> OTHER INFORMATION: synthetic
<220> FEATURE:

```
<221> NAME/KEY: modified_base
<222> LOCATION: (18)..(19)
<223> OTHER INFORMATION: nucleotides 18 and 19 are connected via a
      linker

<400> SEQUENCE: 22
cuguguguac ucugcuucg                                                19

<210> SEQ ID NO 23
<211> LENGTH: 32
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 23
agcagaguac acacagcaua uaccgguaua ug                                 32

<210> SEQ ID NO 24
<211> LENGTH: 20
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (19)..(20)
<223> OTHER INFORMATION: nucleotides 19 and 20 are connected via a
      linker

<400> SEQUENCE: 24
gcugugugua cucugcuucg                                               20

<210> SEQ ID NO 25
<211> LENGTH: 31
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 25
agcagaguac acacagcaua uaccgguaua u                                  31

<210> SEQ ID NO 26
<211> LENGTH: 21
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (20)..(21)
<223> OTHER INFORMATION: nucleotides 20 and 21 are connected via a
      linker

<400> SEQUENCE: 26
ugcugugugu acucugcuuc g                                             21

<210> SEQ ID NO 27
```

```
<211> LENGTH: 30
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 27
agcagaguac acacagcaua uaccgguaua                                              30

<210> SEQ ID NO 28
<211> LENGTH: 22
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (21)..(22)
<223> OTHER INFORMATION: nucleotides 21 and 22 are connected via a
      linker

<400> SEQUENCE: 28
augcugugug uacucugcuu cg                                                      22

<210> SEQ ID NO 29
<211> LENGTH: 29
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 29
agcagaguac acacagcaua uaccgguau                                               29

<210> SEQ ID NO 30
<211> LENGTH: 23
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)..(23)
<223> OTHER INFORMATION: nucleotides 22 and 23 are connected via a
      linker

<400> SEQUENCE: 30
uaugcugugu guacucugcu ucg                                                     23

<210> SEQ ID NO 31
<211> LENGTH: 28
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker
```

```
<400> SEQUENCE: 31
agcagaguac acacagcaua uaccggua                                        28

<210> SEQ ID NO 32
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (23)..(24)
<223> OTHER INFORMATION: nucleotides 23 and 24 are connected via a
      linker

<400> SEQUENCE: 32
auaugcugug uguacucugc uucg                                            24

<210> SEQ ID NO 33
<211> LENGTH: 27
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 33
agcagaguac acacagcaua uaccggu                                         27

<210> SEQ ID NO 34
<211> LENGTH: 25
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 34
uauaugcugu guguacucug cuucg                                           25

<210> SEQ ID NO 35
<211> LENGTH: 26
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 35
agcagaguac acacagcaua uaccgg                                          26

<210> SEQ ID NO 36
<211> LENGTH: 23
<212> TYPE: RNA
<213> ORGANISM: Artificial
<220> FEATURE:
<223> OTHER INFORMATION: synthetic
```

-continued

```
<220> FEATURE:
<221> NAME/KEY: modified_base
<222> LOCATION: (20)..(21)
<223> OTHER INFORMATION: nucleotides 20 and 21 are connected via a
      linker

<400> SEQUENCE: 36 ugcauacuu cucaugguuc gaa                                              23

<210> SEQ ID NO 37
<211> LENGTH: 28
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)..(23)
<223> OTHER INFORMATION: nucleotides 22 and 23 are connected via a
      linker

<400> SEQUENCE: 37
caugagaagu augacaacag ccggcugu                                        28

<210> SEQ ID NO 38
<211> LENGTH: 17
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (16)..(17)
<223> OTHER INFORMATION: nucleotides 16 and 17 are connected via a
      linker

<400> SEQUENCE: 38
acgagacaaa cacuccg                                                    17

<210> SEQ ID NO 39
<211> LENGTH: 34
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 39
aguguuuguc ucguuacaau auccggauau ugua                                 34

<210> SEQ ID NO 40
<211> LENGTH: 23
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)..(23)
<223> OTHER INFORMATION: nucleotides 22 and 23 are connected via a
      linker

<400> SEQUENCE: 40
auuguaacga gacaaacacu ccg                                             23
```

```
<210> SEQ ID NO 41
<211> LENGTH: 28
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 41
aguguuuguc ucguuacaau auccggau                                            28

<210> SEQ ID NO 42
<211> LENGTH: 26
<212> TYPE: RNA
<213> ORGANISM: Artificial
<220> FEATURE:
<223> OTHER INFORMATION: synthetic

<400> SEQUENCE: 42
uuguaacgag acaaacacuc cuucgg                                              26

<210> SEQ ID NO 43
<211> LENGTH: 35
<212> TYPE: RNA
<213> ORGANISM: Artificial
<220> FEATURE:
<223> OTHER INFORMATION: synthetic

<400> SEQUENCE: 43
aguguuuguc ucguuacaau aucccacacc ggaua                                    35

<210> SEQ ID NO 44
<211> LENGTH: 27
<212> TYPE: RNA
<213> ORGANISM: Artificial
<220> FEATURE:
<223> OTHER INFORMATION: synthetic

<400> SEQUENCE: 44
auuguaacga gacaaacacu ccuucgg                                             27

<210> SEQ ID NO 45
<211> LENGTH: 34
<212> TYPE: RNA
<213> ORGANISM: Artificial
<220> FEATURE:
<223> OTHER INFORMATION: synthetic

<400> SEQUENCE: 45
aguguuuguc ucguuacaau aucccacacc ggau                                     34

<210> SEQ ID NO 46
<211> LENGTH: 22
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (21)..(22)
<223> OTHER INFORMATION: nucleotides 21 and 22 are connected via a
      linker

<400> SEQUENCE: 46
```
ugcgcuuuuu ggugacgcuu cg                                            22

<210> SEQ ID NO 47
<211> LENGTH: 29
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 47
agcgucacca aaaagcgcaa uuccggaau                                     29

<210> SEQ ID NO 48
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (23)..(24)
<223> OTHER INFORMATION: nucleotides 23 and 24 are connected via a
      linker

<400> SEQUENCE: 48
auugcgcuuu uuggugacgc uucg                                          24

<210> SEQ ID NO 49
<211> LENGTH: 27
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker

<400> SEQUENCE: 49
agcgucacca aaaagcgcaa uuccgga                                       27

<210> SEQ ID NO 50
<211> LENGTH: 19
<212> TYPE: RNA
<213> ORGANISM: Artificial
<220> FEATURE:
<223> OTHER INFORMATION: synthetic

<400> SEQUENCE: 50
uaugcugugu guacucugc                                                19

<210> SEQ ID NO 51
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)..(23)
<223> OTHER INFORMATION: nucleotides 22 and 23 are connected via a
      linker
<220> FEATURE:
<221> NAME/KEY: modified_base

```
<222> LOCATION: (48)..(49)
<223> OTHER INFORMATION: nucleotides 48 and 49 are connected via a
      linker

<400> SEQUENCE: 51
caugagaagu augacaacag ccggcuguug ucauacuucu cauggUucga a              51

<210> SEQ ID NO 52
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker
<220> FEATURE:
<221> NAME/KEY: modified_base
<222> LOCATION: (50)..(51)
<223> OTHER INFORMATION: nucleotides 50 and 51 are connected via a
      linker

<400> SEQUENCE: 52
aguguuuguc ucguuacaau auccggauau uguaacgaga caaacacucc g              51

<210> SEQ ID NO 53
<211> LENGTH: 61
<212> TYPE: RNA
<213> ORGANISM: Artificial
<220> FEATURE:
<223> OTHER INFORMATION: synthetic

<400> SEQUENCE: 53
aguguuuguc ucguuacaau aucccacacc ggauauugua acgagacaaa cacuccuucg     60
g                                                                    61

<210> SEQ ID NO 54
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker
<220> FEATURE:
<221> NAME/KEY: modified_base
<222> LOCATION: (50)..(51)
<223> OTHER INFORMATION: nucleotides 50 and 51 are connected via a
      linker

<400> SEQUENCE: 54
agcgucacca aaaagcgcaa uuccggaauu gcgcuuuuug gugacgcuuc g              51

<210> SEQ ID NO 55
<211> LENGTH: 19
<212> TYPE: RNA
<213> ORGANISM: Artificial
<220> FEATURE:
<223> OTHER INFORMATION: synthetic

<400> SEQUENCE: 55
guugucauac uucucaugg                                                  19
```

```
<210> SEQ ID NO 56
<211> LENGTH: 19
<212> TYPE: RNA
<213> ORGANISM: Artificial
<220> FEATURE:
<223> OTHER INFORMATION: synthetic

<400> SEQUENCE: 56
auuguaacga gacaaacac                                              19

<210> SEQ ID NO 57
<211> LENGTH: 19
<212> TYPE: RNA
<213> ORGANISM: Artificial
<220> FEATURE:
<223> OTHER INFORMATION: synthetic

<400> SEQUENCE: 57
uugcgcuuuu uggugacgc                                              19
```